US006288234B1

(12) United States Patent
Griffin

(10) Patent No.: US 6,288,234 B1
(45) Date of Patent: Sep. 11, 2001

(54) MULTIBINDING INHIBITORS OF MICROSOMAL TRIGLYCERIDE TRANSFERASE PROTEIN

(75) Inventor: John H. Griffin, Atherton, CA (US)

(73) Assignee: Advanced Medicine, Inc., South San Francisco, CA (US)

( * ) Notice: Subject to any disclaimer, the term of this patent is extended or adjusted under 35 U.S.C. 154(b) by 0 days.

(21) Appl. No.: 09/325,662

(22) Filed: Jun. 4, 1999

Related U.S. Application Data

(60) Provisional application No. 60/088,448, filed on Jun. 8, 1998, and provisional application No. 60/093,072, filed on Jul. 16, 1998.

(51) Int. Cl.$^7$ .................. C07D 211/30; C07D 211/32; C07D 413/00; A01N 43/40; A61K 31/455

(52) U.S. Cl. .................. 546/190; 546/193; 546/194; 546/195; 546/196; 546/197; 546/198; 546/199; 546/200; 546/201; 546/202; 546/203; 546/204; 546/205; 546/206; 546/207; 546/208; 514/252; 514/325; 514/326; 514/424; 514/426; 530/345; 530/389.1; 530/402; 530/807; 549/16; 549/388; 564/172; 564/174

(58) Field of Search .................. 435/7.1, 7.2; 436/501, 436/518; 514/252, 422, 424, 426, 325, 326; 530/345, 389.1, 402, 807; 546/193–208, 190–192; 548/518, 528, 550; 564/172, 174; 549/16, 388

(56) References Cited

U.S. PATENT DOCUMENTS

| H1729 | 5/1998 | Biller et al. . |
| 4,358,525 | 11/1982 | Moobery et al. . |
| 5,712,279 | 1/1998 | Biller et al. . |
| 5,739,135 | 4/1998 | Biller et al. . |
| 5,760,246 | 6/1998 | Biller et al. . |
| 5,827,875 | 10/1998 | Dickenson, Jr. et al. . |

FOREIGN PATENT DOCUMENTS

| 0 643 057 A1 | 3/1995 | (EP) . |
| 96/40640 | 12/1996 | (WO) . |
| 97/26240 | 7/1997 | (WO) . |
| 97/43255 | 11/1997 | (WO) . |
| 98/03069 | 1/1998 | (WO) . |
| 98/03174 | 1/1998 | (WO) . |
| 98/23593 | 6/1998 | (WO) . |
| 98/27979 | 7/1998 | (WO) . |
| 98/31225 | 7/1998 | (WO) . |
| 98/31366 | 7/1998 | (WO) . |
| 98/31367 | 7/1998 | (WO) . |

OTHER PUBLICATIONS

Portoghese, P.S. The Role of Concepts in Structure–Activity Relationship Studies of Opioid Ligands. J. Med. Chem. vol. 35, No. 11, pp. 1927–1937, May 1992.*
S. B. Shuker et al., Science 1996, 274, 1531–1534.
A. Atzel et al., Biochemistry 1993, 32, 10444–10450.
A. Atzel et al., Biochemistry 1994, 33, 15382–15388.
F. Benoist et al., Eur. J. Biochem. 1996, 240, 713–720.
D.A. Gordon et al., Trends Cell Biol. 1995, 5, 317–321.
M. Haghpassand et al., J. Lipid Res. 1996, 37, 1468–1480.
H. Jamil et al., J. Biol. Chem. 1995, 270, 6549–6554.
H. Jamil et al., Proc. Natl. Acad. Sci. U.S.A. 1996, 93, 11991–11995.
J. P. Kane et al., The Metabolic Basis of Inherited Disease, Scriver et al., Eds.; McGraw–Hill, NY, Ed. 7, 1995, pp. 1853–1885.
M. F. Linton et al., J. Lipid Res. 1993, 34, 521–541.
S. L. Ohringer et al., Acta Crystallogr., Sect. D: Biol. Crystallogr. 1996, D52(1), 224–225.
R. Raag et al., J. Mol. Biol. 1988, 200, 553–569.
Robbins Pathological Basis of Disease, 5$^{th}$ Edition (1994), pp. 473–484.
C.C. Shoulders et al., J. Hum. Mol. Genet. 1993, 2, 2109–2116.
P. A. Timmins et al., Science 1992, 257, 652–655.
J. R. Wetterau et al., Biochemistry 1991, 30, 4406–4412.
J. R. Wetterau et al., Biochem. Biophys. Acta 1997, 1345, 136–150.
J. R. Wetterau et al., J. Biol. Chem. 1990, 265, 9800–9807.
J. R. Wetterau et al., Science 1998, 282, 751–754.

* cited by examiner

Primary Examiner—Jyothsna Venkat
Assistant Examiner—Maurie E. Garcia
(74) Attorney, Agent, or Firm—Burns, Doane, Swecker & Mathis L.L.P.

(57) ABSTRACT

Disclosed are multibinding compounds which inhibit microsomal triglyceride transferase protein (MTP), a protein which mediates the transfer of lipids during the assembly of lipoproteins and related biomolecules. The multibinding compounds contain from 2 to 10 ligands covalently attached to one or more linkers. The multibinding compounds of this invention are useful for lowering serum lipid, cholesterol and/or triglyceride levels, and for preventing and treating disorders associated with hyperlipemia, hyperlipidemia, hyperlipoproteinemia, hypercholestrolemia, hypertriglyceridemia and the like, such atherosclerosis.

10 Claims, 10 Drawing Sheets

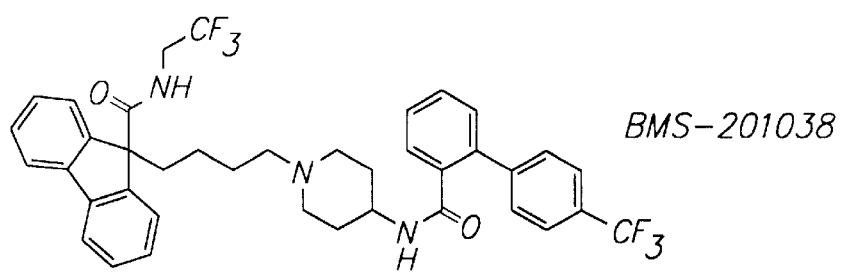
FIG. 1A
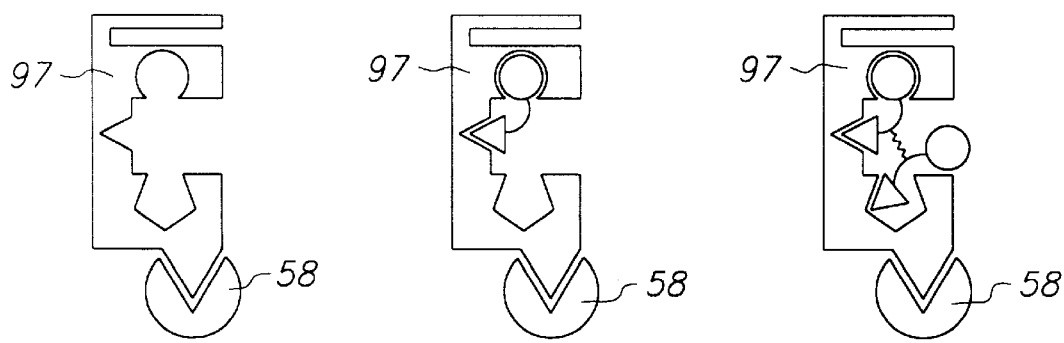
MTP        MTP:BMS-201038        Homodimer
Complex
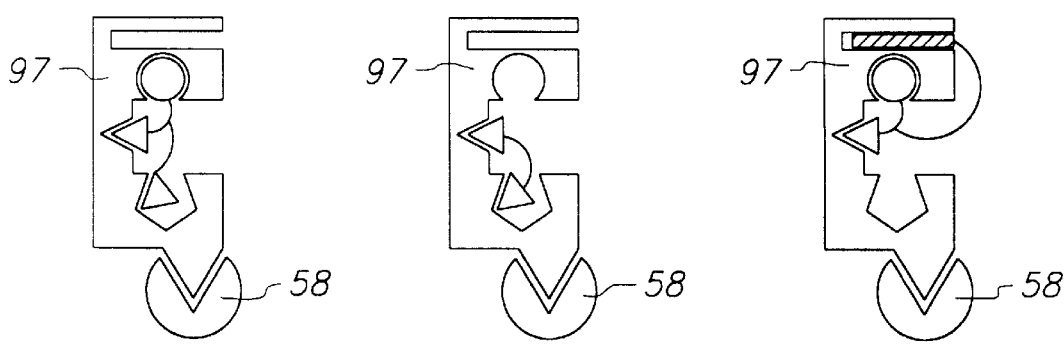
Sesquimer      Dimer of      Conjugate with
Half-substructure    Phospholipid
FIG. 1B

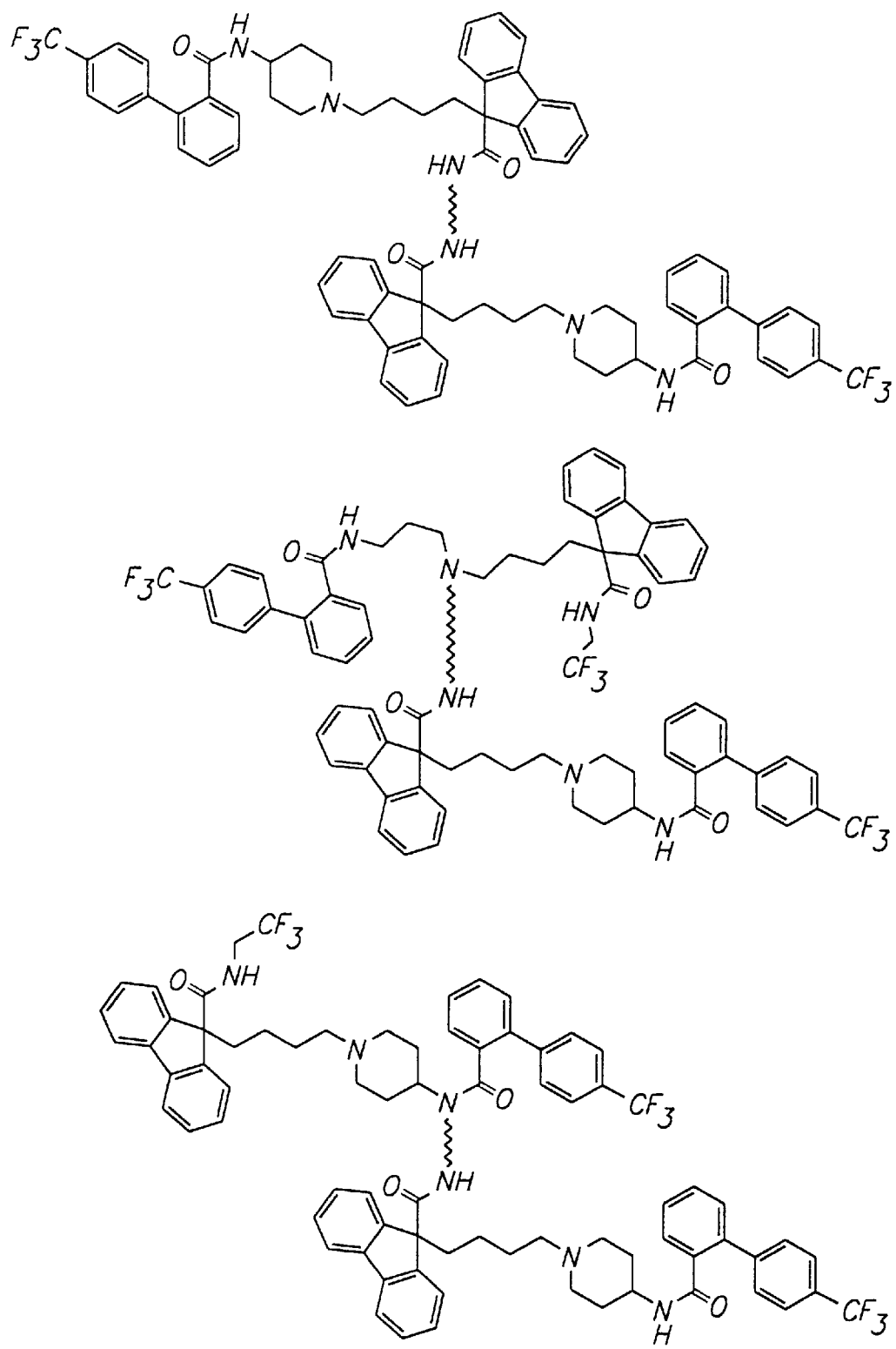
FIG. 6-A

FIG. 6-B
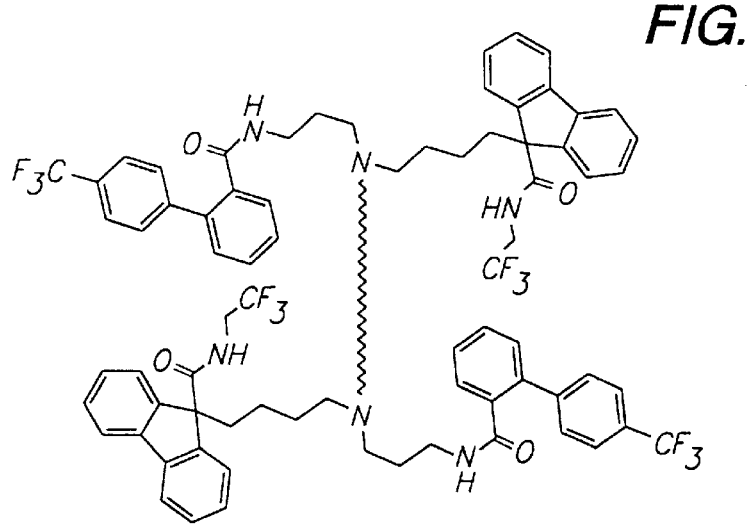
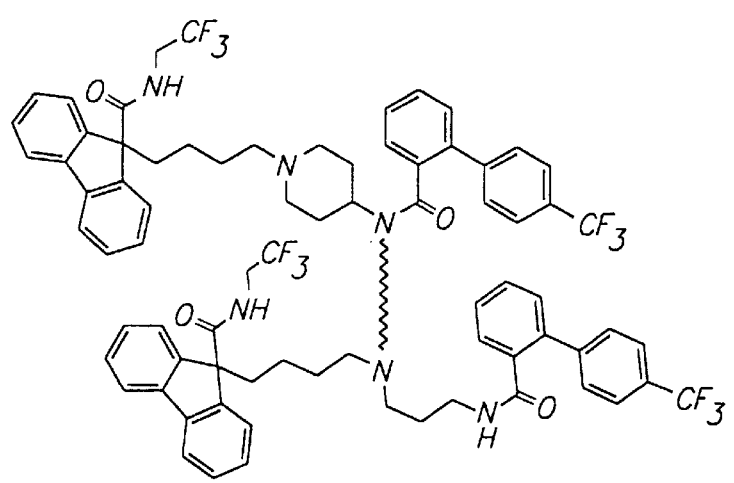
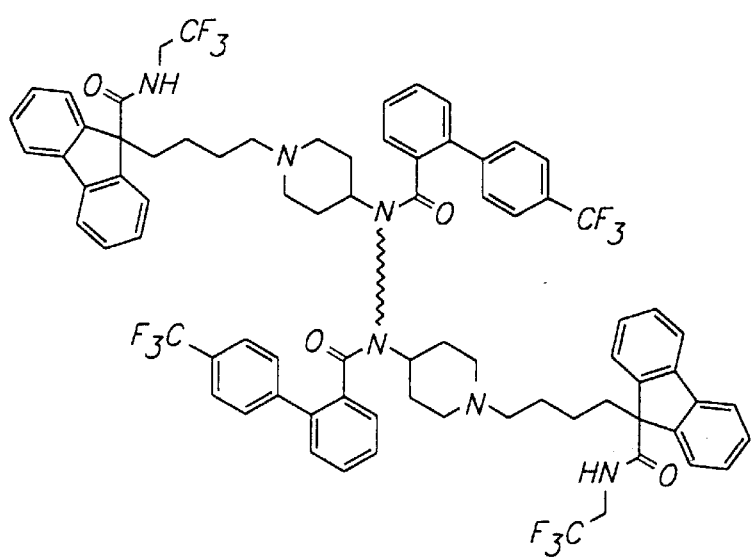

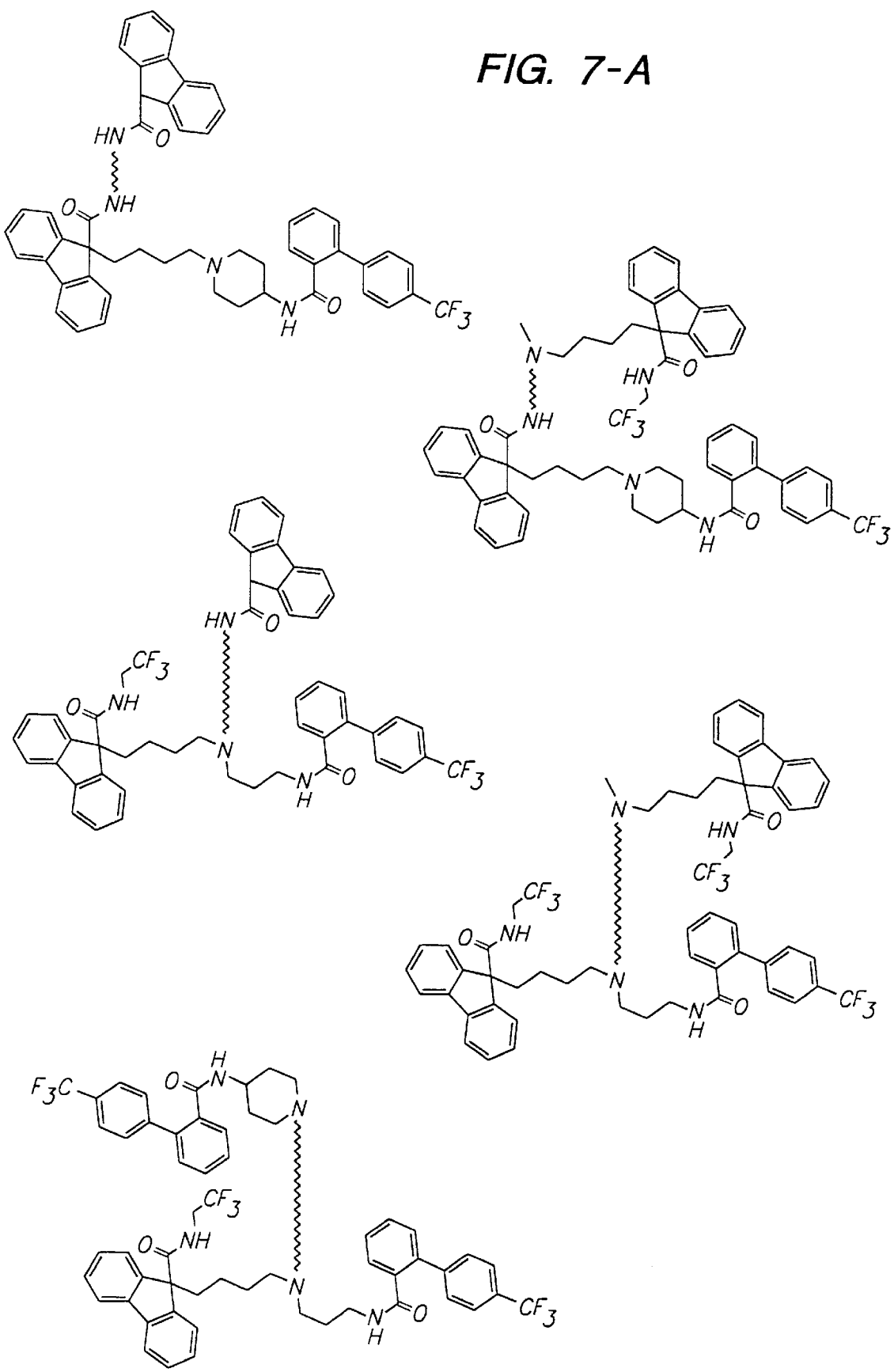
FIG. 7-A

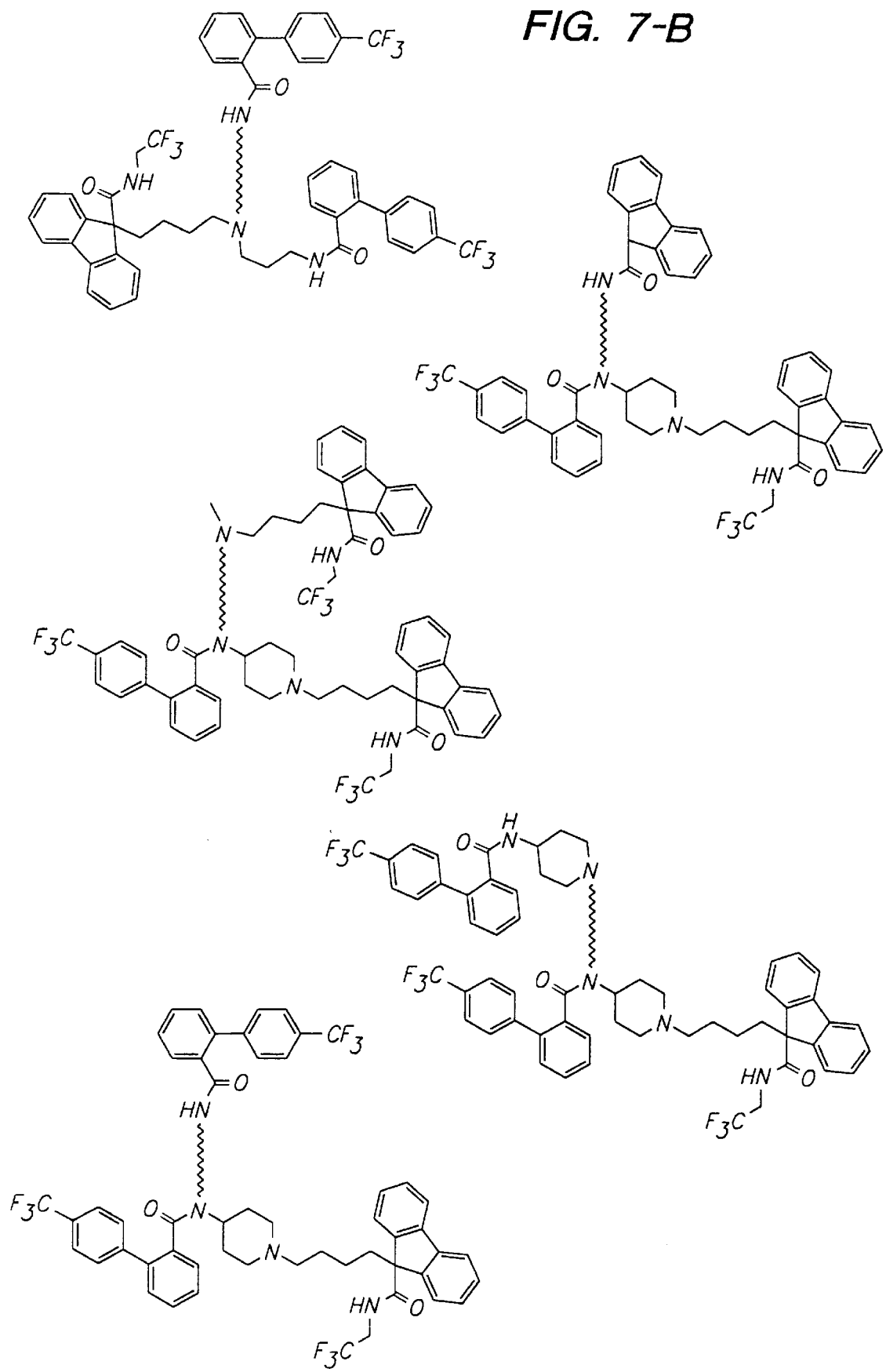
FIG. 7-B

MULTIBINDING INHIBITORS OF MICROSOMAL TRIGLYCERIDE TRANSFERASE PROTEIN

CROSS-REFERENCE TO RELATED APPLICATIONS

This application claims the benefit of U.S. patent application Ser. No. 60/088,448, filed Jun. 8, 1998; and U.S. patent application Ser. No. 60/093,072, filed Jul. 16, 1998; the disclosures of which are incorporated herein by reference in their entirety.

BACKGROUND OF THE INVENTION

1. Field of the Invention

This invention relates to novel multibinding compounds (agents) that inhibit microsomal triglyceride transferase protein (MTP) and to pharmaceutical compositions comprising such compounds. Accordingly, the multibinding compounds and pharmaceutical compositions of this invention are useful in preventing and treating various disorders associated with hyperlipidemia and related disorders, such as atherosclerosis.

References

The following publications are cited in this application as superscript numbers:

[1] J. R. Wetterau et al., *Biochim. Biophys. Acta* 1997, 1345, 136–150.

[2] D. A. Gordon et al., *Trends Cell Biol.* 1995, 5, 317–321.

[3] Robbins *Pathological Basis of Disease*, 5th Edition (1994), pp. 473–484.

[4] S. L. Ohringer et al., *Acta Crystallogr., Sect. D: Biol. Crystallogr.* 1996, D52(1), 224–225.

[5] J. R. Wetterau et al., *J. Biol. Chem.* 1990, 265, 9800–9807.

[6] J. R. Wetterau et al., *Biochemistry* 1991, 30, 4406–4412.

[7] C. C. Shoulders et al., *J. Hum. Mol. Genet.* 1993, 2, 2109–2116.

[8] R. Raag et al., *J. Mol. Biol.* 1988, 200, 553–569.

[9] P. A. Timmins et al., *Science* 1992, 257, 652–655.

[10] A. Atzel et al., *Biochemistry* 1993, 32, 10444–10450.

[11] A. Atzel et al., *Biochemistry* 1994, 33, 15382–15388.

[12] H. Jamil et al., *J. Biol. Chem.* 1995, 270, 6549–6554.

[13] H. Jamil et al., *Proc. Natl. Acad. Sci. U.S.A.* 1996, 93, 11991–11995.

[14] J. P. Kane et al., *The Metabolic Basis of Inherited Disease*, Scriver et al., Eds.; McGraw-Hill, N.Y., Ed. 7, 1995, pp. 1853–1885.

[15] M. F. Linton et al., *J. Lipid Res.* 1993, 34, 521–541.

[16] U.S. Pat. No. 5,712,279, issued Jan. 27, 1998 to Biller et al.

[17] U.S. Pat. No. 5,739,135, issued Apr. 14, 1998 to Biller et al.

[18] U.S. Pat. No. 5,760,246, issued Jun. 2, 1998 to Biller et al.

[19] U.S. Pat. No. 5,827,875, issued Oct. 27, 1998 to Dickson Jr. et al.

[20] U.S. Statutory Invention Registration No. H1729, published May 5, 1998 by Biller et al.

[21] WO 96/40640, published Dec. 19, 1996.

[22] WO 97/26240, published Jul. 24, 1997.

[23] WO 97/43255, published Nov. 20, 1997.

[24] WO 98/03069, published Jan. 29, 1998.

[25] WO 98/03174, published Jan. 29, 1998.

[26] WO 98/23593, published Jun. 4, 1998.

[27] WO 98/27979, published Jul. 2, 1998.

[28] WO 98/31225, published Jul. 23, 1998.

[29] WO 98/31366, published Jul. 23, 1998.

[30] WO 98/31367, published Jul. 23, 1998.

[31] EP 0 643 057 A1, published Mar. 15, 1995.

[32] M. Haghpassand et al., *J. Lipid Res.* 1996, 37, 1468–1480.

[33] F. Benoist et al., *Eur. J. Biochem.* 1996, 240, 713–720.

[34] J. R. Wetterau et al., *Science* 1998, 282, 751–754.

All of the above publications are herein incorporated by reference in their entirety to the same extent as if each individual publication was specifically and individually indicated to be incorporated by reference in its entirety.

2. State of the Art

Microsomal triglyceride transferase protein (MTP) is a lipid transfer protein which mediates the transport of lipids, such as triglycerides, cholesterol esters, and phosphatidylcholine, between membranes.[1,2] Accordingly, MTP is believed to play a role in the assembly of lipoproteins and related biomolecules. In this regard, MTP has been implicated as a probable agent in the assembly of apolipoprotein B (Apo B)-containing lipoproteins which are known to contribute to the formation of atherosclerotic lesions. Thus, effective inhibitors of MTP would be useful in preventing the onset and progression of atherosclerosis, including myocardial infarction, stroke, peripheral vascular disease and the like, which accounts for one-half of deaths in the United States.[3]

MTP was originally isolated from the microsomal fraction of bovine liver and has subsequently been found within the lumen of microsomes isolated from both the liver and intestine.[1] Since its initial isolation, MTP has been extensively characterized.[4,5,6] MTP is a soluble, heterodimeric protein composed of 58 and 97 kDa subunits, both of which are required for activity. The protein is localized within the lumen of the endoplasmic reticulum. The 58 kDa subunit is identical to protein disulfide isomerase (PDI), though the complex exhibits no PDI activity and isolated PDI does not exhibit MTP activity. The noncovalent MTP heterodimer does not display significant dissociation/reassociation and is either asymmetric and/or highly hydrated. The unique 97 kDa subunit bears homology to other lipid-transporting proteins, including the lipovitillin-phosvitin complex (LPC) and, to a lesser extent, plasma cholesteryl ester transfer protein (CETP).[7] Structural characterization of LPC reveals that it comprises a large cavity that complexes multiple copies of phospholipid.[8,9]

Kinetic analysis of the MTP-mediated lipid transport processes have revealed ping pong bi bi kinetics which is consistent with a mechanism of action in which MTP binds and shuttles lipid molecules between membranes.[10] This suggests that stable MTP-lipid complexes are formed during the transfer process, which is further supported by the observation that incubation of MTP with donor vesicles containing a variety of radio-labeled lipids followed by re-isolation affords MTP containing up to three molecules of lipid.[11,12] The ability of lipid molecules to occupy distinct binding sites on MTP is suggested by the observation of biphasic kinetics for transfer of phosphatidyl choline, which binds with a 2:1 stoichiometry to the enzyme.[12] Moreover, an MTP inhibitor has been hown to fully ablate the MTP-mediated transfer of triglycerides and cholesterol sters but not that of phosphatidyl choline.[13]

The ability of MTP inhibitors to prevent the onset and progression of therosclerosis and related disorders is supported by the observation that utations in MTP are the only known bases for abetalipoproteinemia, an autosomal recessive disorder characterized by the virtual absence of apoB-containing plasma lipoproteins.[1,2,14] Abetalipoproteinemia sub atherosclerosis, but they suffer from a variety of side effects as a result of the extreme nature of their condition. This suggests that non-complete inhibition of MTP would be requisite in an agent designed for human therapy. In this regard, hypobetalipoproteinemia is a relevant model for MTP inhibition. This condition is displayed by individuals who are heterozygous for mutations in apolipoproteinB.[15] These subjects have levels of apoB-containing lipoproteins half that of normal subjects and, as a result, they enjoy extended lifespans.

Inhibitors of MTP have been described in the patent and technical literature. See, by way of example, U.S. Pat. No. 5,712,279;[16] U.S. Pat. No. 5,739,135;[17] U.S. Pat. No. 5,760,246;[18] U.S. Pat. No. 5,827,875;[19] U.S. Statutory Invention Registration No. H1729;[20] WO 96/40640;[21] WO 97/26240;[22] WO 97/43255;[23] WO 98/03069;[24] WO 98/03174;[25] WO 98/23593;[26] WO 98/27979;[27] WO 98/31225;[28] WO 98/31366;[29] WO 98/31367;[3] EP 0 643 057 A1;[31] M. Haghpassand et al.;[32] F. Benoist et al.;[33] and J. R. Wetterau et al.[34] Notwithstanding such inhibitors, a need exists for effective MTP inhibitors having improved biological and/or therapeutic effects.

It has now been discovered that MTP inhibitors having surprising and unexpected properties can be prepared by linking from 2 to 10 ligands capable of binding to MTP to one or more linkers. The chemical structure of one known inhibitor of MTP, i.e. BMS-201038, is illustrated in FIG. 1A.[16,34] Without being limited to theory, a potential complex of this compound with MTP is illustrated in FIG. 1B. Based on the distinct multiple binding sites believed to be present in MTP, various multibinding compounds are illustrated in FIG. 1B. Such multibinding compounds provide greater biological and/or therapeutic effects than the aggregate of the unlinked ligands due to their multibinding properties.

SUMMARY OF THE INVENTION

This invention is directed to novel multibinding compounds (agents) that inhibit microsomal triglyceride transferase protein (MTP). The multibinding compounds of this invention are useful in the prevention and treatment of diseases associated with hyperlipemia, hyperlipidemia, hyperlipoproteinemia, hypercholestrolemia, hypertriglyceridemia and the like, such as atherosclerosis.

Accordingly, in one of its composition aspects, this invention provides a multibinding compound of formula I:

$(L)_p(X)_q$      I wherein each X is independently a linker; p is an integer of from 2 to 10; and q is an integer of from 1 to 20; and each L is independently a ligand selected from the group consisting of:

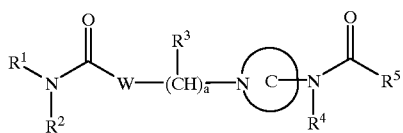

IA

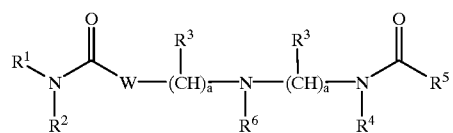

IB

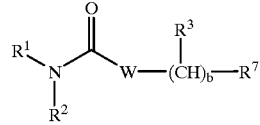

IC

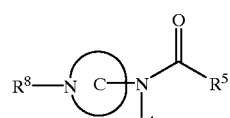

ID

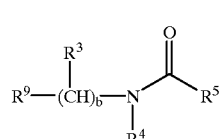

IE wherein
each W is a divalent radical independently selected from the group consisting of:

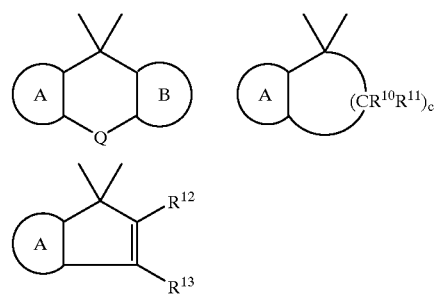

each $R^1$ is independently selected from the group consisting of hydrogen, akyl, substituted alkyl, alkenyl, substituted alkenyl, cycloalkyl, substituted cycloalkyl, cycloalkenyl, substituted cycloalkenyl, aryl, heteroaryl and a covalent bond linking the ligand to a linker;
each $R^2$ is independently selected from the group consisting of hydrogen, alkyl, substituted alkyl, alkenyl, substituted alkenyl, cycloalkyl, substituted cycloalkyl, cycloalkenyl, substituted cycloalkenyl, aryl, heteroaryl and a covalent bond linking the ligand to a linker;
each $R^3$ is independently selected from the group consisting of hydrogen, alkyl and halo;
each $R^4$ is independently selected from the group consisting of hydrogen, alkyl, substituted alkyl, alkenyl, substituted alkenyl and a covalent bond linking the ligand to a linker;
each $R^5$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, alkoxy, substituted alkoxy, cycloalkoxy, substituted cycloalkoxy, aryl, aryloxy, heteroaryl, heteroaryloxy, amino, substituted amino and a covalent bond linking the ligand to a linker; or $R^4$ and $R^5$ may be joined, together with the >NC(O)— group to which they are attached, to form a heterocyclic ring;

each $R^6$ is independently selected from the group consisting of hydrogen, alkyl, substituted alkyl, alkenyl, substituted alkenyl, cycloalkyl, substituted cycloalkyl, cycloalkenyl, substituted cycloalkenyl, aryl, heteroaryl and a covalent bond linking the ligand to a linker;

each $R^7$ is independently selected from the group consisting of hydrogen, alkyl, substituted alkyl, alkenyl, substituted alkenyl, cycloalkyl, substituted cycloalkyl, cycloalkenyl, substituted cycloalkenyl, aryl, heteroaryl, heterocyclic, a covalent bond linking the ligand to a linker and —$NR^{14}R^{15}$, where $R^{14}$ is selected from the group consisting of hydrogen, alkyl, substituted alkyl, alkenyl, substituted alkenyl, cycloalkyl, substituted cycloalkyl, cycloalkenyl, substituted cycloalkenyl, aryl and heteroaryl; and $R^{15}$ is a covalent bond linking the ligand to a linker;

each $R^8$ is independently selected from the group consisting of hydrogen, acyl, alkyl, substituted alkyl, alkenyl, substituted alkenyl, cycloalkyl, substituted cycloalkyl, cycloalkenyl, substituted cycloalkenyl, aryl, heteroaryl, heterocyclic, a covalent bond linking the ligand to a linker each $R^9$ is independently selected from the group consisting of hydrogen, alkyl, substituted alkyl, alkenyl, substituted alkenyl, cycloalkyl, substituted cycloalkyl, cycloalkenyl, substituted cycloalkenyl, aryl, heteroaryl, heterocyclic, a covalent bond linking the ligand to a linker and —$NR^{14}R^{15}$, where $R^{14}$ is selected from the group consisting of hydrogen, alkyl, substituted alkyl, alkenyl, substituted alkenyl, cycloalkyl, substituted cycloalkyl, cycloalkenyl, substituted cycloalkenyl, aryl and heteroaryl; and $R^{15}$ is a covalent bond linking the ligand to a linker;

each $R^{10}$, $R^{11}$, $R^{12}$ and $R^{13}$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, alkoxy, substituted alkoxy, cycloalkoxy, substituted cycloalkoxy, aryl, aryloxy, halo, heteroaryl, heteroaryloxy, thioalkoxy, substituted thioalkoxy, thioaryloxy, thioheteroaryloxy, acyloxy, aminoacyl, aminocarbonyl, —$S(O)R^{16}$ and —$SO_2R^{16}$, where each $R^{16}$ is independently selected from the group consisting of alkyl, substituted alkyl, alkenyl, substituted alkenyl, cycloalkyl, substituted cycloalkyl, aryl and heteroaryl;

each ring A, together with the atoms to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;

each ring B, together with the atoms to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;

each ring C, together with the nitrogen atom to which it is attached, forms heterocyclic ring;

each Q is independently selected from the group consisting of a covalent bond, —O—, —S—, —S(O)—, —$SO_2$—, alkylene, substituted alkylene, alkenylene, substituted alkenylene and —$NR^{17}$—, where $R^{17}$ is selected from the group consisting of alkyl, substituted alkyl, alkenyl, substituted alkenyl, cycloalkyl, substituted cycloalkyl, cycloalkenyl, substituted cycloalkenyl, aryl and heteroaryl;

each a is independently an integer of from 2 to 6;

each b is independently an integer of from 0 to 6;

each c is independently an integer of from 2 to 4;

and pharmaceutically-acceptable salts or pro-drugs thereof;

provided that when p is 2, q is 1 and a first ligand has formula IA or IB, where $R^1$ or $R^2$ is a covalent bond linking the first ligand to the linker, then a second ligand does not have formula ID or IE, where $R^8$ or $R^9$ are a covalent bond linking the second ligand to the linker.

Preferably q is less than p in the multibinding compounds of this invention.

Preferably, W in formulae IA, IB and IC is a divalent radical having the formula:

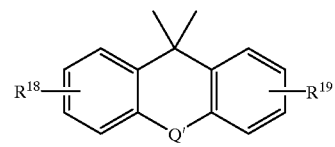

wherein each $R^{18}$ and $R^{19}$ are independently selected from the group consisting of hydrogen or halo; and Q' is a covalent bond, —O— or —S—.

Preferably, each $R^5$ group is independently selected from the group consisting of aryl, heteroaryl, heterocyclic, cycloalkyl and substituted cycloalkyl. Additionally, each $R^5$ group is preferably substituted with from 1 to 4 substituents and one of the substituents is attached to the ring atom in the position adjacent to the atom attached to the —C(O)— group. Still more preferably, each $R^5$ is a 2-(4'-trifluoromethylphenyl)phenyl group.

Preferably, ring C in formulae IA and ID forms a piperidine or a 1,2,3,4-tetrahydroisoquinoline ring.

In another of its composition aspects, this invention provides a multibinding compound of formula II:

   II wherein X' is a linker; and each L' is a ligand independently selected from the group consisting of:

IIA

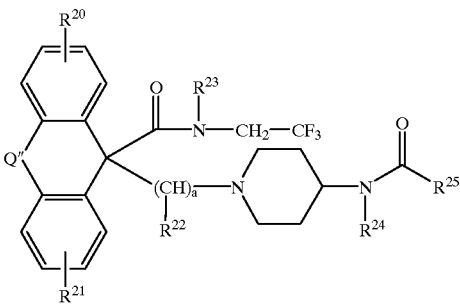

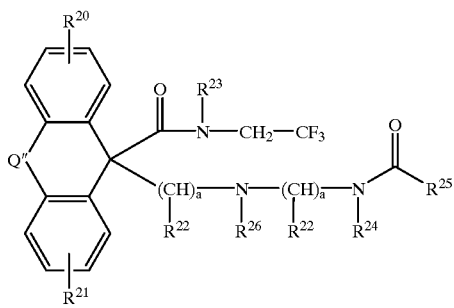

IIB

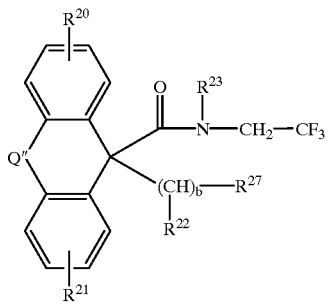

IIC

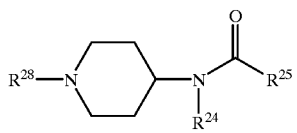

IID

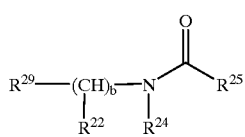

IIE wherein
each $R^{22}$ and $R^{21}$ is independently selected from the group consisting of hydrogen and halo;
each $R^{22}$ is independently selected from the group consisting of hydrogen, alkyl and halo;
each $R^{23}$ is independently selected from the group consisting of hydrogen and a covalent bond linking the ligand to the linker;
each $R^{24}$ is independently selected from the group consisting of hydrogen and a covalent bond linking the ligand to the linker;
each $R^{25}$ is independently selected from the group consisting of aryl, heteroaryl, heterocyclic, cycloalkyl, substituted cycloalkyl and a covalent bond linking the ligand to the linker;
each $R^{26}$ is independently selected from the group consisting of hydrogen, alkyl and a covalent bond linking the ligand to the linker;
each $R^{27}$ is independently selected from the group consisting of hydrogen, a covalent bond linking the ligand to a linker and —$NR^{30}R^{31}$, where $R^{30}$ is selected from the group consisting of hydrogen and alkyl; and $R^{31}$ is a covalent bond linking the ligand to a linker;
each $R^{28}$ is a covalent bond linking the ligand to a linker;
each $R^{29}$ is independently selected from the group consisting of a covalent bond linking the ligand to a linker and —$NR^{30}R^{31}$, where $R^{30}$ is selected from the group consisting of hydrogen and alkyl; and $R^{31}$ is a covalent bond linking the ligand to a linker;

each Q" is independently selected from the group consisting of a covalent bond, —O— and —S—
each a is independently an integer of from 2 to 6;
each b is independently an integer of from 0 to 6;
and pharmaceutically-acceptable salts or pro-drugs thereof;
provided that in each ligand only one of $R^{23}$, $R^{24}$, $R^{25}$, $R^{26}$, $R^{27}$, $R^{28}$ and $R^{29}$ is a covalent bond linking the ligand to the linker;
and further provided that when a first ligand has formula IIA or IIB, where $R^{23}$ is a covalent bond linking the first ligand to the linker, then a second ligand does not have formula IID or IIE, where $R^{28}$ or $R^{29}$ are a covalent bond linking the second ligand to the linker.

Preferably, each $R^{25}$ group is independently selected from the group consisting of aryl, heteroaryl, heterocyclic, cycloalkyl and substituted cycloalkyl. Additionally, each $R^{25}$ group is preferably substituted with from 1 to 4 substituents and one of the substituents is attached to the ring atom in the position adjacent to the atom attached to the —C(O)— group. More preferably, each $R^1$ is a 2-(4'-trifluoromethylphenyl)phenyl group.

Preferably, in the multibinding compounds of this invention, each linker (i.e., X or X') independently has the formula:

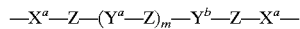

wherein
m is an integer of from 0 to 20;
$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;
$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —N=C($X^a$)—NR'—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting hydrogen, alkyl, substituted alkyl, cycloalkyl, substituted cycloalkyl, alkenyl, bstituted alkenyl, cycloalkenyl, substituted cycloalkenyl, alkynyl, substituted kynyl, aryl, heteroaryl and heterocyclic.

In yet another of its composition aspects, this invention provides a harmaceutical composition comprising a pharmaceutically acceptable carrier and an effective amount of a multibinding compound of formula I or II.

The multibinding compounds of this invention are effective inhibitors of microsomal triglyceride transferase protein (MTP), a protein which mediates the transfer of lipids during the assembly of lipoproteins and related biomolecules. Thus, the multibinding compounds of this invention are useful for treating disorders associated with hyperlipidemia and other lipid-related conditions or disorders. Accordingly, in one of its method aspects, this invention provides a method for preventing or treating atherosclerosis in a patient, the method comprising administering to a patient with atherosclerosis or at risk for developing atherosclerosis a pharmaceutical composition comprising a pharmaceutically-acceptable carrier and a therapeutically-effective amount of a multibinding compound of formulae I or II.

In another of its method aspects, this invention provides a method for lowering serum lipid, cholesterol and/or triglyceride levels in a patient, the method comprising administering to a patient a pharmaceutical composition comprising a pharmaceutically-acceptable carrier and a therapeutically-effective amount of a multibinding compound of formulae I or II.

And, in yet another of its method aspects, this invention provides a method for preventing or treating hyperlipemia, hyperlipidemia, hyperlipoproteinemia, hypercholestrolemia, hypertriglyceridemia, pancreatitis, diabetes and/or obsesity in a patient, the method comprising administering to a patient in need of such treatment a pharmaceutical composition comprising a pharmaceutically-acceptable carrier and a therapeutically-effective amount of a multibinding compound of formulae I or II.

This invention is also directed to general synthetic methods for generating large libraries of diverse multimeric compounds which multimeric compounds are candidates for possessing multibinding properties for microsomal triglyceride transferase protein. The diverse multimeric compound libraries provided by this invention are synthesized by combining a library of linkers with a library of ligands each having complementary functional groups permitting covalent linkage. The library of linkers is preferably selected to have diverse properties such as valency, linker length, linker geometry and rigidity, hydrophilicity or hydrophobicity, amphiphilicity, acidity, basicity, polarizability and polarization. The library of ligands is preferably selected to have diverse attachment points on the same ligand, different functional groups at the same site of otherwise the same ligand, and the like.

Additionally, this invention is directed to libraries of diverse multimeric compounds which multimeric compounds are candidates for possessing multibinding properties for microsomal triglyceride transferase protein. These libraries are prepared via the methods described above and permit the rapid and efficient evaluation of what molecular constraints impart multibinding properties to a ligand or a class of ligands for microsomal triglyceride transferase protein.

Accordingly, in one of its method aspects, this invention is directed to a method for identifying multimeric ligand compounds possessing multibinding properties for microsomal triglyceride transferase protein, which method comprises:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand;

(c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands; and (d) assaying the multimeric ligand compounds produced in the library prepared in (c) above to identify multimeric ligand compounds possessing multibinding properties for microsomal triglyceride transferase protein.

In another of its method aspects, this invention is directed to a method for identifying multimeric ligand compounds possessing multibinding properties for microsomal triglyceride transferase protein, which method comprises:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand;

(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and (d) assaying the multimeric ligand compounds produced in the library prepared in (c) above to identify multimeric ligand compounds possessing multibinding properties for microsomal triglyceride transferase protein.

Preferably, in these methods, the preparation of the multimeric ligand compound library is achieved by either the sequential or concurrent combination of the two or more stoichiometric equivalents of the ligands identified in (a) with the linkers identified in (b).

Additionally, the multimeric ligand compounds comprising the multimeric ligand compound library are preferably dimeric. More preferably, the dimeric ligand compounds comprising the dimeric ligand compound library are heterodimeric. The heterodimeric ligand compound library is preferably prepared by sequential addition of a first and second ligand.

In a preferably embodiment of the above methods, prior to procedure (d), each member of the multimeric ligand compound library is isolated from the library. More preferably, each member of the library is isolated by preparative liquid chromatography mass spectrometry (LCMS).

In the above methods, the linker or linkers employed are preferably selected from the group comprising flexible linkers, rigid linkers, hydrophobic linkers, hydrophilic linkers, linkers of different geometry, acidic linkers, basic linkers, linkers of different polarization and/or polarizability and amphiphilic linkers. More preferably, the linkers comprise linkers of different chain length and/or having different complementary reactive groups. Still more preferably, the linkers are selected to have different linker lengths ranging from about 2 to 100 Å.

The ligand or mixture of ligands employed in the above methods is preferably selected to have reactive functionality at different sites on said ligands. More preferably, the reactive functionality is selected from the group consisting of carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof wherein the reactive functionality on the ligand is selected to be complementary to at least one of the reactive groups on the linker so that a covalent linkage can be formed between the linker and the ligand.

In one preferred embodiment of the above methods, the multimeric ligand compound library comprises homomeric ligand compounds. In another preferred embodiment, the multimeric ligand compound library comprises heteromeric ligand compounds.

In one of its composition aspects, this invention is directed to a library of multimeric ligand compounds which may possess multivalent properties for microsomal triglyceride transferase protein, which library is prepared by the method comprising:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand; and (c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands.

In another of its composition aspects, this invention is directed to a library of multimeric ligand compounds which may possess multivalent properties for microsomal triglyceride transferase protein, which library is prepared by the method comprising:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand; and (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the linker or linkers employed are preferably selected from the group comprising flexible linkers, rigid linkers, hydrophobic linkers, hydrophilic linkers, linkers of different geometry, acidic linkers, basic linkers, linkers of different polarization and/or polarizability and amphiphilic linkers. More preferably, the linkers comprise linkers of different chain length and/or having different complementary reactive groups. Still more preferably, the linkers are selected to have different linker lengths ranging from about 2 to 100 Å.

In the above libraries, the ligand or mixture of ligands is preferably selected to have reactive functionality at different sites on said ligands. Preferably, the reactive functionality is selected from the group consisting of carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof wherein the reactive functionality on the ligand is selected to be complementary to at least one of the reactive groups on the linker so that a covalent linkage can be formed between the linker and the ligand.

In one embodiment, the multimeric ligand compound library comprises homomeric ligand compounds (i.e., each of the ligands is the same, although it may be attached at different points). In another embodiment, the multimeric ligand compound library comprises heteromeric ligand compounds (i.e., at least one of the ligands is different from the other ligands).

In another of its method aspects, this invention is directed to an iterative method for identifying multimeric ligand compounds possessing multibinding properties for microsomal triglyceride transferase protein, which method comprises:

(a) preparing a first collection or iteration of multimeric compounds which is prepared by contacting at least two stoichiometric equivalents of the ligand or mixture of ligands which target a receptor with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;

(b) assaying said first collection or iteration of multimeric compounds to assess which if any of said multimeric compounds possess multibinding properties for microsomal triglyceride transferase protein;

(c) repeating the process of (a) and (b) above until at least one multimeric compound is found to possess multibinding properties for microsomal triglyceride transferase protein;

(d) evaluating what molecular constraints imparted or are consistent with imparting multibinding properties to the multimeric compound or compounds found in the first iteration recited in (a)–(c) above;

(e) creating a second collection or iteration of multimeric compounds which elaborates upon the particular molecular constraints imparting multibinding properties to the multimeric compound or compounds found in said first iteration;

(f) evaluating what molecular constraints imparted or are consistent with imparting enhanced multibinding properties to the multimeric compound or compounds found in the second collection or iteration recited in (e) above;

(g) optionally repeating steps (e) and (f) to further elaborate upon said molecular constraints.

Preferably, steps (e) and (f) are repeated from 2–50 times. More preferably, steps (e) and (f) are repeated from 5–50 times.

Preferably, the ligands employed in the above methods and library compositions are selected from ligands of formula IA–IE, more preferably, from ligands of formula IIA–IIE.

BRIEF DESCRIPTION OF THE DRAWINGS

FIG. 1A illustrates a known inhibitor of microsomal triglyceride transferase protein (MTP).

FIG. 1B illustrates a various binding complexes of MTP with a known inhibitor of MTP and various multibinding compounds.

FIGS. 6A and 6B (collectively referred to herein as FIG. 6), 7A and 7B (collecitively referred to herein as FIG. 7), and 8 illustrate multibinding compounds of this invention where~represents the linker.

DETAILED DESCRIPTION OF THE INVENTION

Figure 2:
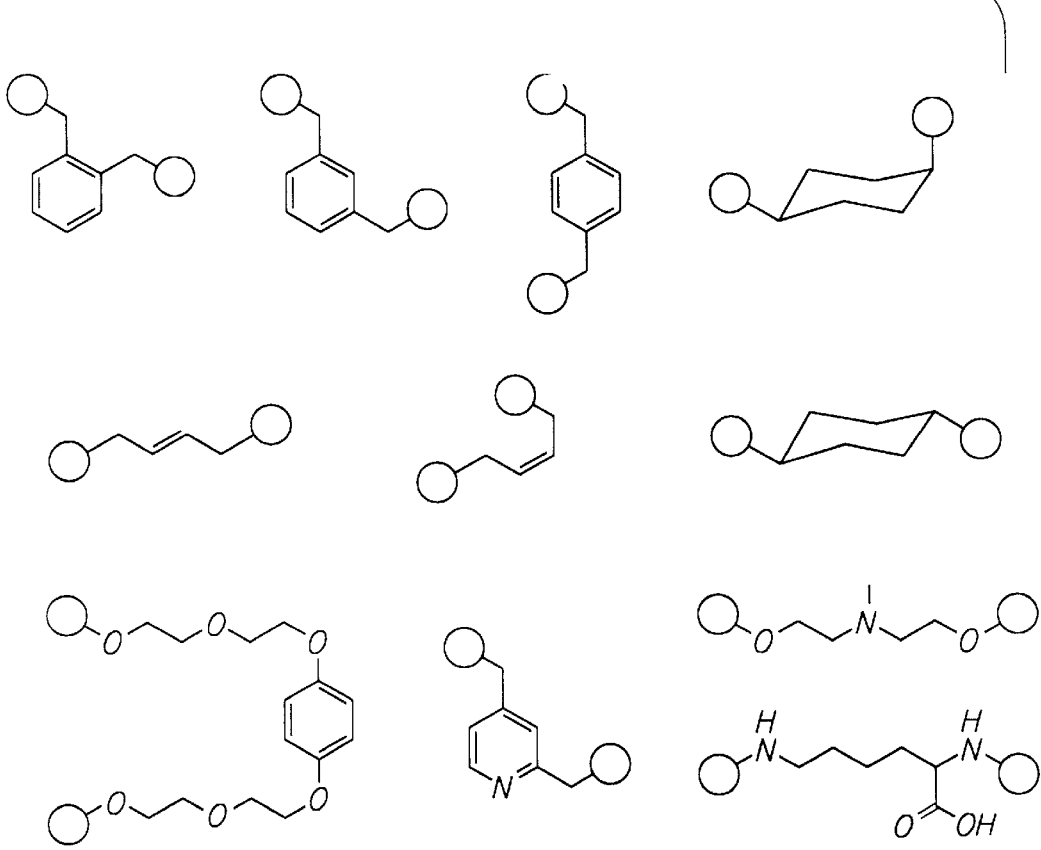
FIG. 2 illustrates examples of multibinding compounds comprising 2 ligands attached in different formats to a linker.

This invention is directed to multibinding compounds which inhibit microsomal triglyceride transferase protein (MTP), pharmaceutical compositions containing such multibinding compounds and methods for treating disorders associated with hyperlipidemia and other lipid-related conditions or disorders. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably I to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocylooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocylooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocylooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡—C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalk cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, alkyl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chioro, bromo and jodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 sub stituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—. The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically-acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable thiol blocking groups include disulfide groups, acyl groups, benzyl groups, and the like.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC), and the like which can be removed by conventional conditions compatible with the nature of the product.

Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "ligand" as used herein denotes a compound that is capable of binding to microsomal triglyceride transferase protein. The specific region or regions of the ligand that is (are) recognized by the protein is designated as the "ligand domain". A ligand may be either capable of binding to the protein by itself, or may require the presence of one or more non-ligand components for binding (e.g., $Ca^{+2}$, $Mg^{+2}$ or a water molecule is required for the binding of a ligand to various ligand binding sites).

Examples of ligands useful in this invention are described herein. Those skilled in the art will appreciate that portions of the ligand structure that are not essential for specific molecular recognition and binding activity may be varied substantially, replaced or substituted with unrelated structures (for example, with ancillary groups as defined below) and, in some cases, omitted entirely without affecting the binding interaction. The primary requirement for a ligand is that it has a ligand domain as defined above. It is understood that the term ligand is not intended to be limited to compounds known to be useful in binding to microsomal triglyceride transferase protein (e.g., known drugs). Those skilled in the art will understand that the term ligand can equally apply to a molecule that is not normally associated with binding properties. In addition, it should be noted that ligands that exhibit marginal activity or lack useful activity as monomers can be highly active as multivalent compounds because of the benefits conferred by multivalency.

The term "multibinding compound or agent" refers to a compound that is capable of multivalency, as defined below, and which has 2–10 ligands covalently bound to one or more linkers which may be the same or different. Multibinding compounds provide a biological and/or therapeutic effect greater than the aggregate of unlinked ligands equivalent thereto which are made available for binding. That is to say that the biological and/or therapeutic effect of the ligands attached to the multibinding compound is greater than that achieved by the same amount of unlinked ligands made available for binding to the ligand binding sites (receptors). The phrase "increased biological or therapeutic effect" includes, for example: increased affinity, increased selectivity for target, increased specificity for target, increased potency, increased efficacy, decreased toxicity, improved duration of activity or action, decreased side effects, increased therapeutic index, improved bioavailibity, improved pharmacokinetics, improved activity spectrum, and the like. The multibinding compounds of this invention will exhibit at least one and preferably more than one of the above-mentioned affects.

The term "mulimeric compound" refers to a compound containing 2 to 10 ligands covalently connected through at least one linker which compound may or may not possess multibinding properties.

The term "potency" refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model). The finding that the multbinding agent produces an equivalent biological or therapeutic effect at a lower concentration than the aggregate unlinked ligand is indicative of enhanced potency.

The term "univalency" as used herein refers to a single binding interaction between one ligand as defined herein with one ligand binding site as defined herein. It should be noted that a compound having multiple copies of a ligand (or ligands) exhibit univalency when only one ligand is interacting with a ligand binding site. Examples of univalent interactions are depicted below.

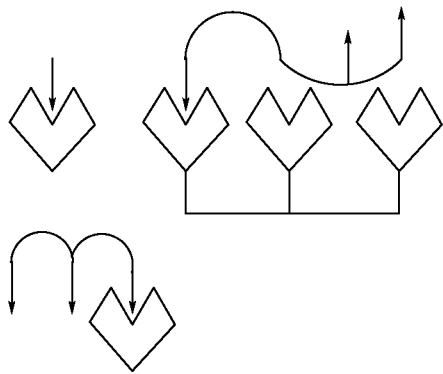

The term "multivalency" as used herein refers to the concurrent binding of from 2 to 10 linked ligands (which may be the same or different) and two or more corresponding receptors (ligand binding sites) on one or more biomolecules i.e., proteins or enzymes, which may be the same or different.

For example, two ligands connected through a linker that bind concurrently to two ligand binding sites would be considered as bivalency; three ligands thus connected would be an example of trivalency. An example of trivalent binding, illustrating a multibinding compound bearing three ligands versus a monovalent binding interaction, is shown below:

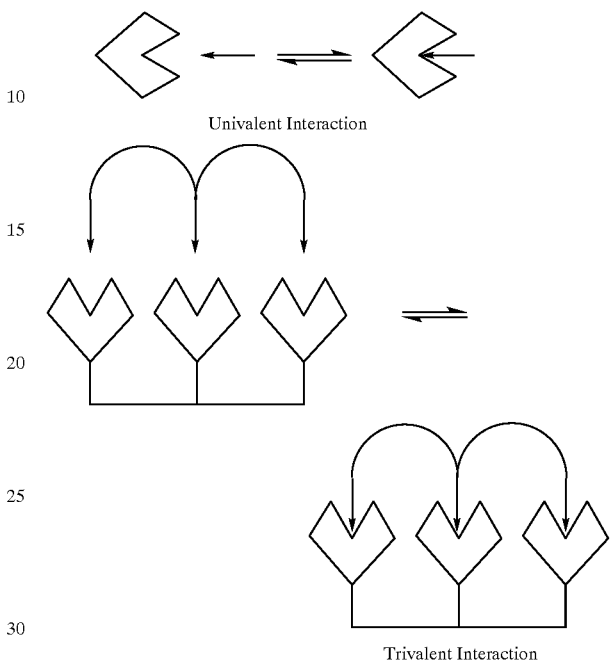

It should be understood that all compounds that contain multiple copies of a ligand attached to a linker or to linkers do not necessarily exhibit the phenomena of multivalency, i.e., that the biological and/or therapeutic effect of the multibinding agent is greater than the sum of the aggregate of unlinked ligands made available for binding to the ligand binding site (receptor). For multivalency to occur, the ligands that are connected by a linker or linkers have to be presented to their ligand binding sites by the linker(s) in a specific manner in order to bring about the desired ligand-orienting result, and thus produce a multibinding event.

The term "selectivity" or "specificity" is a measure of the binding preferences of a ligand for different ligand binding sites (receptors). The selectivity of a ligand with respect to its target ligand binding site relative to another ligand binding site is given by the ratio of the respective values of $K_d$ (i.e., the dissociation constants for each ligand-receptor complex) or, in cases where a biological effect is observed below the $K_d$, the ratio of the respective $EC_{50}$'s (i.e., the concentrations that produce 50% of the maximum response for the ligand interacting with the two distinct ligand binding sites (receptors)).

The term "ligand binding site" denotes the site(s) on the microsomal triglyceride transferase protein that recognizes a ligand domain and provides a binding partner for the ligand. The ligand binding site may be defined by monomeric or multimeric structures. This interaction may be capable of producing a unique biological effect, for example, agonism, antagonism, modulatory effects, may maintain an ongoing biological event, and the like.

The terms "agonism" and "antagonism" are well known in the art. The term "modulatory effect" refers to the ability of the ligand to change the activity of an agonist or antagonist through binding to a ligand binding site.

It should be recognized that the ligand binding sites of the enzyme that participate in biological multivalent binding interactions are constrained to varying degrees by their intra- and inter-molecular associations (e.g., such macromolecular structures may be covalently joined to a single structure, noncovalently associated in a multimeric structure, embedded in a membrane or polymeric matrix, and so on) and therefore have less translational and rotational freedom than if the same structures were present as monomers in solution.

The term "inert organic solvent" or "inert solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition which is modulated by treatment with a ligand" covers all disease states (i.e., pathologic conditions) which are generally acknowledged in the art to be usefully treated with a ligand for microsomal triglyceride transferase protein in general, and those disease states which have been found to be usefully treated by a specific multibinding compound of our invention. Such disease states include, by way of example only, the treatment of a mammal afflicted with atherosclerosis, hyperlipemia, hyperlipidemia, hyperlipoproteinemia, hypercholestrolemia, hypertriglyceridemia, pancreatitis, diabetes, obesity and the like.

The term "therapeutically effective amount" refers to that amount of multibinding compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker" identified where appropriate by the symbol X or X', refers to a group or groups that covalently links from 2 to 10 ligands (as identified above) in a manner that provides for a compound capable of multivalency. Each linker may be chiral or achiral. Among other features, the linker is a ligand-orienting entity that permits attachment of multiple copies of a ligand (which may be the same or different) thereto. In some cases, the linker may itself be biologically active. The term "linker" does not, however, extend to cover solid inert supports such as beads, glass particles, fibers, and the like. But it is understood that the multibinding compounds of this invention can be attached to a solid support if desired. For example, such attachment to solid supports can be made for use in separation and purification processes and similar applications.

The extent to which multivalent binding is realized depends upon the efficiency with which the linker or linkers that joins the ligands presents these ligands to the array of available ligand binding sites. Beyond presenting these ligands for multivalent interactions with ligand binding sites, the linker or linkers spatially constrains these interactions to occur within dimensions defined by the linker or linkers. Thus, the structural features of the linker (valency, geometry, orientation, size, flexibility, chemical composition, etc.) are features of multibinding agents that play an important role in determining their activities.

The linkers used in this invention are selected to allow multivalent binding of ligands to the ligand binding sites of microsomal triglyceride transferase protein, whether such sites are located interiorly, both interiorly and on the periphery of the protein structure, or at any intermediate position thereof.

The ligands are covalently attached to the linker or linkers using conventional chemical techniques providing for covalent linkage of the ligand to the linker or linkers. Reaction chemistries resulting in such linkages are well known in the art and involve the use of complementary functional groups on the linker and ligand. Preferably, the complementary functional groups on the linker are selected relative to the functional groups available on the ligand for bonding or which can be introduced onto the ligand for bonding. Again, such complementary functional groups are well known in the art. For example, reaction between a carboxylic acid of either the linker or the ligand and a primary or secondary amine of the ligand or the linker in the presence of suitable, well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker.

Table I below illustrates numerous complementary reactive groups and the resulting bonds formed by reaction there between.

TABLE I

Representative Complementary Binding Chemistries

| First Reactive Group | Second Reactive Group | Linkage |
|---|---|---|
| hydroxyl | isocyanate | urethane |
| amine | epoxide | b-hydroxyamine |
| sulfonyl halide | amine | sulfonamide |
| carboxyl | amine | amide |
| hydroxyl | alkyl/aryl halide | ether |

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

Suitable linkers are discussed more fully below.

At present, it is preferred that the multibinding agent is a bivalent compound, e.g., two ligands which are covalently linked to linker X.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits the facile synthesis thereof. In one embodiment, the library of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members; preferably from 2 to $10^9$ members and still more preferably from 10 to $10^4$ members.

The term "pseudohalide" refers to a functional group which react in a displacement reaction in a manner similar to a halogen, e.g., functions as a leaving group is a displacement reaction. Such functional groups include, by way of example, mesyl, tosyl, azido, cyano and the like.

Methodology

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines".

The intersection of the framework (linker) and the ligand group, and indeed, the framework (linker) itself can have many different bonding patterns. Examples of acceptable patterns of three contiguous atom arrangements are shown in the following diagram:

```
CCC NCC OCC SCC PCC
CCN NCN OCN SCN PCN
CCO NCO OCO SCO PCO
CCS NCS OCS SCS PCS
CCP NCP OCP SCP PCP

CNC NNC ONC SNC PNC
CNN NNN ONN SNN PNN
CNO NNO ONO SNO PNO
CNS NNS ONS SNS PNS
CNP NNP ONP SNP PNP

COC NOC OOC SOC POC
CON NON OON SON PON
 COO  NOO  OOO  SOO  POO
COS NOS OOS SOS POS
COP NOP OOP SOP POP

CSC NSC OSC SSC PSC
CSN NSN OSN SSN PSN
CSO NSO OSO SSO PSO
CSS NSS OSS SSS PSS
CSP NSP OSP SSP PSP

CPC NPC OPC SPC PPC
CPN NPN OPN SPN PPN
CPO NPO OPO SPO PPO
CPS NPS OPS SPS PPS
 CPP  NPP  OPP  SPP  PPP
```

One skilled in the art would be able to identify bonding patterns that would produce multivalent compounds. Methods for producing these bonding arrangements are described in March, "Advanced Organic Chemistry" 4th Edition, Wiley-Interscience, New York, N.Y. (1992). All of the possible arrangements for the five most preferred atoms are shown. Each atom has a variety of acceptable oxidation states. The bonding arrangements underlined are less acceptable and are not preferred.

Examples of molecular structures in which the above bonding patterns could be employed as components of the linker are shown below.

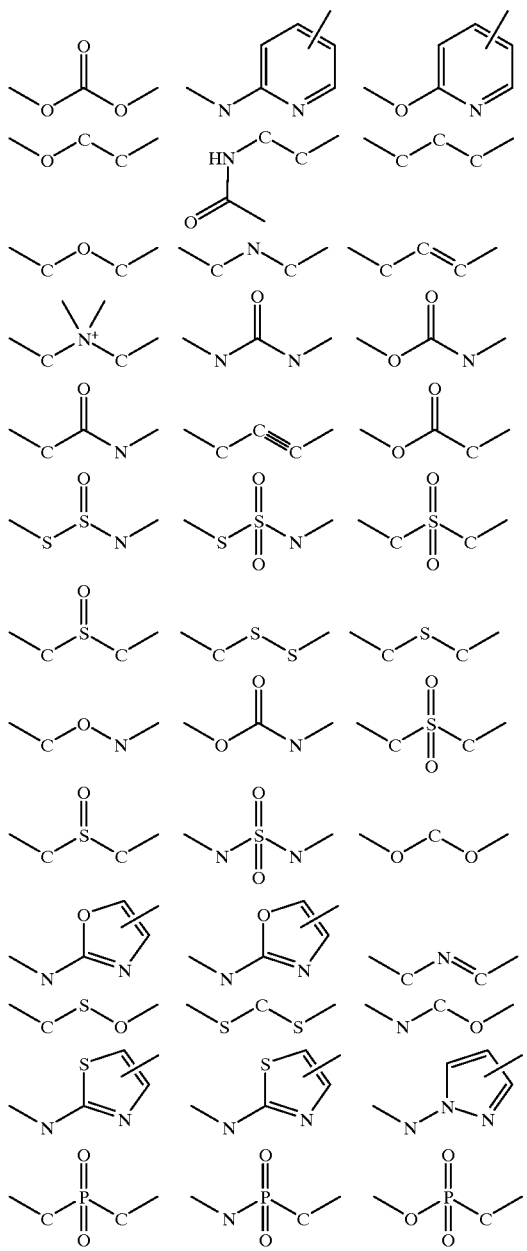

The identification of an appropriate framework geometry and size for ligand domain presentation are important steps in the construction of a multibinding compound with enhanced activity. Systematic spatial searching strategies can be used to aid in the identification of preferred frameworks through an iterative process. FIG. 2 illustrates a useful strategy for determining an optimal framework display orientation for ligand domains. Various other strategies are known to those skilled in the art of molecular design and can be used for preparing compounds of this invention.

As shown in FIG. 2, display vectors around similar central core structures such as a phenyl structure and a cyclohexane structure can be varied, as can the spacing of the ligand domain from the core structure (i.e., the length of the attaching moiety). It is to be noted that core structures other than those shown here can be used for determining the optimal framework display orientation of the ligands. The process may require the use of multiple copies of the same central core structure or combinations of different types of display cores.

Figure 3:
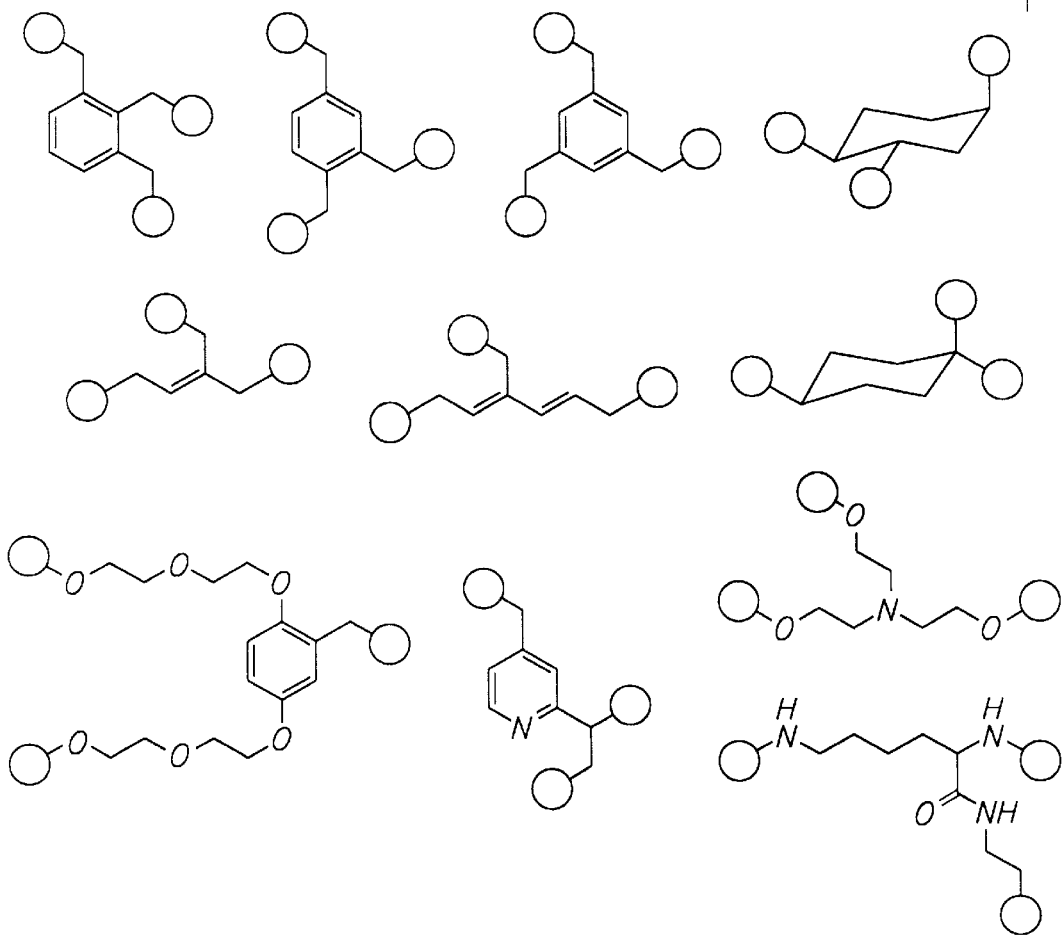
FIG. 3 illustrates examples of multibinding compounds comprising 3 ligands attached in different formats to a linker.

The above-described process can be extended to trimers (FIG. 3) and compound of higher valency.

Assays of each of the individual compounds of a collection generated as described above will lead to a subset of compounds with the desired enhanced activities (e.g., potency, selectivity, etc.). The analysis of this subset using a technique such as Ensemble Molecular Dynamics will provide a framework orientation that favors the properties desired. A wide diversity of linkers is commercially available (see, e.g., Available Chemical Directory (ACD)). Many of the linkers that are suitable for use in this invention fall into this category. Other can be readily synthesized by methods well known in the art and/or are described below.

Having selected a preferred framework geometry, the physical properties of the linker can be optimized by varying the chemical composition thereof. The composition of the linker can be varied in numerous ways to achieve the desired physical properties for the multibinding compound.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof.

Examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/ hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/ hydrophilicity will be a polyether.

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphate, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoylphosphatidylcholine, dioleoylphosphatidylcholine, distearoylphosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (e.g., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, include deprotectation of a carboxyl, hydroxyl, thiol or amino group by a change in pH, oxidation, reduction or other mechanisms known to those skilled in the art which result in removal of the protecting group, is within the scope of this invention.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that links the ligands in such a manner that they are presented to the target receptor for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

Figure 4:
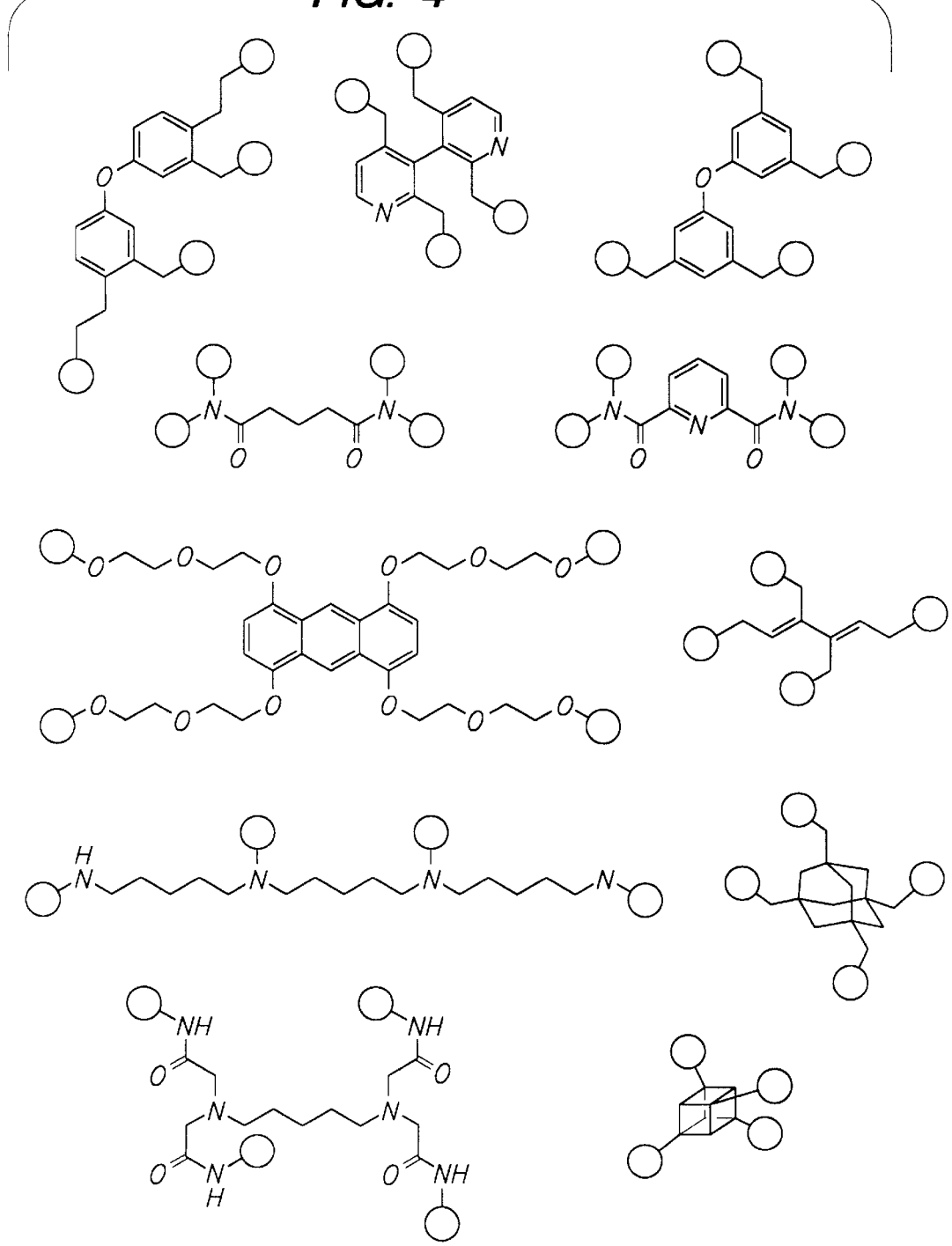
FIG. 4 illustrates examples of multibinding compounds comprising 4 ligands attached in different formats to a linker.

The simplest and most preferred multibinding compound is a bivalent compound which can be represented as L—X—L, where each L is independently a ligand which may be the same or different and each X is independently the linker. Examples of such bivalent compounds are provided in FIG. 2 where each shaded circle represents a ligand. A trivalent compound could also be represented in a linear fashion, i.e., as a sequence of repeated units L—X—L—X—L, in which L is a ligand and is the same or different at each occurrence, as can X. However, a trimer can also be a radial multibinding compound comprising three ligands attached to a central core, and thus represented as $(L)_3X$, where the linker X could include, for example, an aryl or cycloalkyl group. Illustrations of trivalent and tetravalent compounds of this invention are found in FIGS. 3 and 4 respectively where, again, the shaded circles represent ligands. Tetravalent compounds can be represented in a linear array, e.g.,

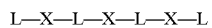

in a branched array, e.g.,

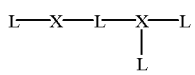

(a branched construct analogous to the isomers of butane—n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker.

Figure 5:
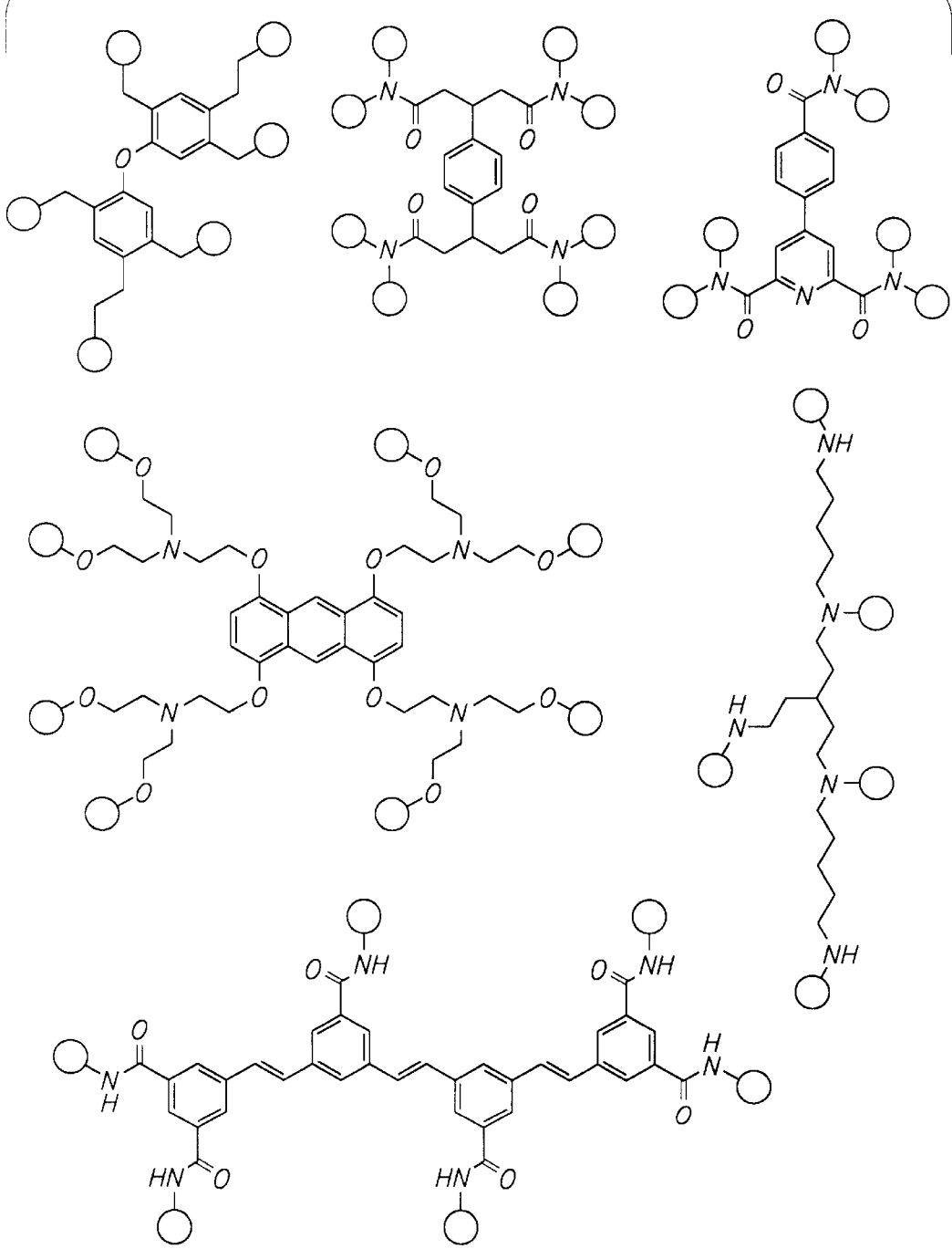
FIG. 5 illustrates examples of multibinding compounds comprising >4 ligands attached in different formats to a linker.

The same considerations apply to higher multibinding compounds of this invention containing 5–10 ligands as illustrated in FIG. 5 where, as before, the shaded circles represent ligands. However, for multibinding agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

Certain of the above described compounds may alternatively be represented as cyclic chains of the form:

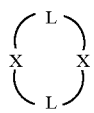

and variants thereof.

All of the above variations are intended to be within the scope of the invention defined by the formula $(L)_p(X)_q$.

With the foregoing in mind, a preferred linker may be represented by the following formula:

$$-X^a-Z-(Y^a-Z)_m-Y^b-Z-X^a-$$

in which:

m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of:

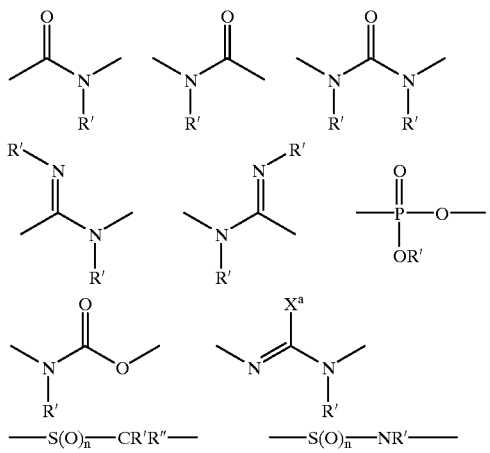

—S—S— or a covalent bond;

in which:

n is 0, 1 or 2; and

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, the linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In one embodiment of this invention, the linker (i.e., X or X') is selected from those shown in Table II:

TABLE II

Representative Linkers

Linker

—HN—(CH$_2$)$_2$—NH—C(O)—(CH$_2$)—C(O)—NH—(CH$_2$)$_2$—NH—
—HN—(CH$_2$)$_2$—NH—C(O)—(CH$_2$)$_2$—C(O)—NH—(CH$_2$)$_2$—NH—
—HN—(CH$_2$)$_2$—NH—C(O)—(CH$_2$)$_3$—C(O)—NH—(CH$_2$)$_2$—NH—
—HN—(CH$_2$)$_2$—NH—C(O)—(CH$_2$)$_4$—C(O)—NH—(CH$_2$)$_2$—NH—
—HN—(CH$_2$)$_2$—NH—C(O)—(CH$_2$)$_5$—C(O)—NH—(CH$_2$)$_2$—NH—
—HN—(CH$_2$)$_2$—NH—C(O)—(CH$_2$)$_6$—C(O)—NH—(CH$_2$)$_2$—NH—
—HN—(CH$_2$)$_2$—NH—C(O)—(CH$_2$)$_7$—C(O)—NH—(CH$_2$)$_2$—NH—
—HN—(CH$_2$)$_2$—NH—C(O)—(CH$_2$)$_8$—C(O)—NH—(CH$_2$)$_2$—NH—
—HN—(CH$_2$)$_2$—NH—C(O)—(CH$_2$)$_9$—C(O)—NH—(CH$_2$)$_2$—NH—

TABLE II-continued

Representative Linkers

Linker

—HN—(CH$_2$)$_2$—NH—C(O)—(CH$_2$)$_{10}$—C(O)—NH—(CH$_2$)$_2$—NH—
—HN—(CH$_2$)$_2$—NH—C(O)—(CH$_2$)$_{11}$—C(O)—NH—(CH$_2$)$_2$—NH—
—HN—(CH$_2$)$_2$—NH—C(O)—(CH$_2$)$_{12}$—C(O)—NH—(CH$_2$)$_2$—NH—
—HN—(CH$_2$)$_2$—NH—C(O)—Z—C(O)—NH—(CH$_2$)$_2$—NH—where Z is 1,2-phenyl
—HN—(CH$_2$)$_2$—NH—C(O)—Z—C(O)—NH—(CH$_2$)$_2$—NH—where Z is 1,3-phenyl
—HN—(CH$_2$)$_2$—NH—C(O)—Z—C(O)—NH—(CH$_2$)$_2$—NH—where Z is 1,4-phenyl
—HN—(CH$_2$)$_2$—NH—C(O)—Z—O—Z—C(O)—NH—(CH$_2$)$_2$—NH—where Z is 1,4-phenyl
—HN—(CH$_2$)$_2$—NH—C(O)—(CH$_2$)$_2$—CH(NH—C(O)—(CH$_2$)$_8$—CH$_3$)—C(O)—NH—(CH$_2$)$_2$—NH—
—HN—(CH$_2$)$_2$—NH—C(O)—(CH$_2$)—O—(CH$_2$)—C(O)—NH—(CH$_2$)$_2$—NH—
—HN—(CH$_2$)$_2$—NH—C(O)—Z—C(O)—NH—(CH$_2$)$_2$—NH—
where Z is 5-(n-octadecyloxy)-1,3-phenyl
—HN—(CH$_2$)$_2$—NH—C(O)—(CH$_2$)$_2$—CH(NH—C(O)—Z)—C(O)—NH—(CH$_2$)$_2$—NH—
where Z is 4-biphenyl
—HN—(CH$_2$)$_2$—NH—C(O)—Z—C(O)—NH—(CH$_2$)$_2$—NH—
where Z is 5-(n-butyloxy)-1,3-phenyl
—HN—(CH$_2$)$_2$—NH—C(O)—(CH$_2$)$_8$-trans-(CH=CH)—C(O)—NH—(CH$_2$)$_2$—NH—
—HN—(CH$_2$)$_2$—NH—C(O)—(CH$_2$)$_2$—CH(NH—C(O)—(CH$_2$)12—CH$_3$)—C(O)—NH—(CH$_2$)$_2$—NH—
—HN—(CH$_2$)$_2$—NH—C(O)—(CH$_2$)$_2$—CH(NH—C(O)—Z)—C(O)—NH—(CH$_2$)$_2$—NH—
where Z is 4-(n-octyl)-phenyl
—HN—(CH$_2$)—Z—O—(CH$_2$)$_6$—O—Z—(CH$_2$)—NH— where Z is 1,4-phenyl
—HN—(CH$_2$)$_2$—NH—C(O)—(CH$_2$)$_2$—NH—C(O)—(CH$_2$)$_3$—C(O)—NH—(CH$_2$)$_2$—C(O)—NH—(CH$_2$)$_2$—NH—
—HN—(CH$_2$)$_2$—NH—C(O)—(CH$_2$)$_2$—CH(NH—C(O)—Ph)—C(O)—NH—(CH$_2$)$_2$—NH—
—HN—(CH$_2$)$_2$—NH—C(O)—(CH$_2$)—N+((CH$_2$)$_9$—CH$_3$)(CH$_2$—C(O)—NH—(CH$_2$)$_2$—NH$_2$)—(CH$_2$)—C(O)—NH—(CH$_2$)$_2$—NH—
—HN—(CH$_2$)$_2$—NH—C(O)—(CH$_2$)—N((CH$_2$)$_9$—CH$_3$)—(CH$_2$)—C(O)—NH—(CH$_2$)$_2$—NH—
—HN—(CH$_2$)$_2$—NH—C(O)—(CH$_2$)—NH—C(O)—(CH$_2$)$_2$—NH—C(O)—(CH$_2$)$_3$—C(O)—NH—(CH$_2$)$_2$—C(O)—NH—(CH$_2$)$_2$—C(O)—NH—(CH$_2$)$_2$—NH—
—HN—(CH$_2$)$_2$—NH—C(O)—Z—C(O)—NH—(CH$_2$)$_2$—NH—
where Z is 5—hydroxy—1,3-phenyl In another embodiment of this invention, the linker (i.e., X, X' or X") has the formula:

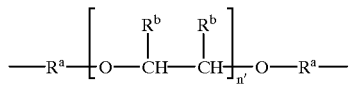

wherein
each $R^a$ is independently selected from the group consisting of a covalent bond, alkylene, substituted alkylene and arylene;
each $R^b$ is independently selected from the group consisting of hydrogen, alkyl and substituted alkyl; and
n' is an integer ranging from 1 to about 20.
In yet another embodiment, the linker (i.e., X or X') has the formula: —(CH$_2$)$_n$—, where n' is an integer ranging from 1 to about 20, preferably from 2 to 6.
In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

Preparation of Multibinding Compounds

The multibinding compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

Any compound which inhibits or binds to microsomal triglyceride transferase protein can be used as a ligand in this invention. As discussed in further detail below, numerous such compounds are known in the art and any of these known compounds or derivatives thereof may be employed as ligands in this invention. Typically, a compound selected for use as a ligand will have at least one functional group, such as an amino, amido, hydroxyl, thiol or carboxyl group and the like, which allows the compound to be readily coupled to the linker. Compounds having such functionality are either known in the art or can be prepared by routine modification of known compounds using conventional reagents and procedures. The patents and publications set forth below provide numerous examples of suitably functionalized compounds with inhibit or bind to microsomal triglyceride transferase protein and intermediates thereof which may be used as ligands in this invention.

The ligand can be covalently attached to the linker through any available position on the ligand, provided that when the ligand is attached to the linker, the ligand retains its ability to inhibit or bind to microsomal triglyceride transferase protein.

Figure 8:
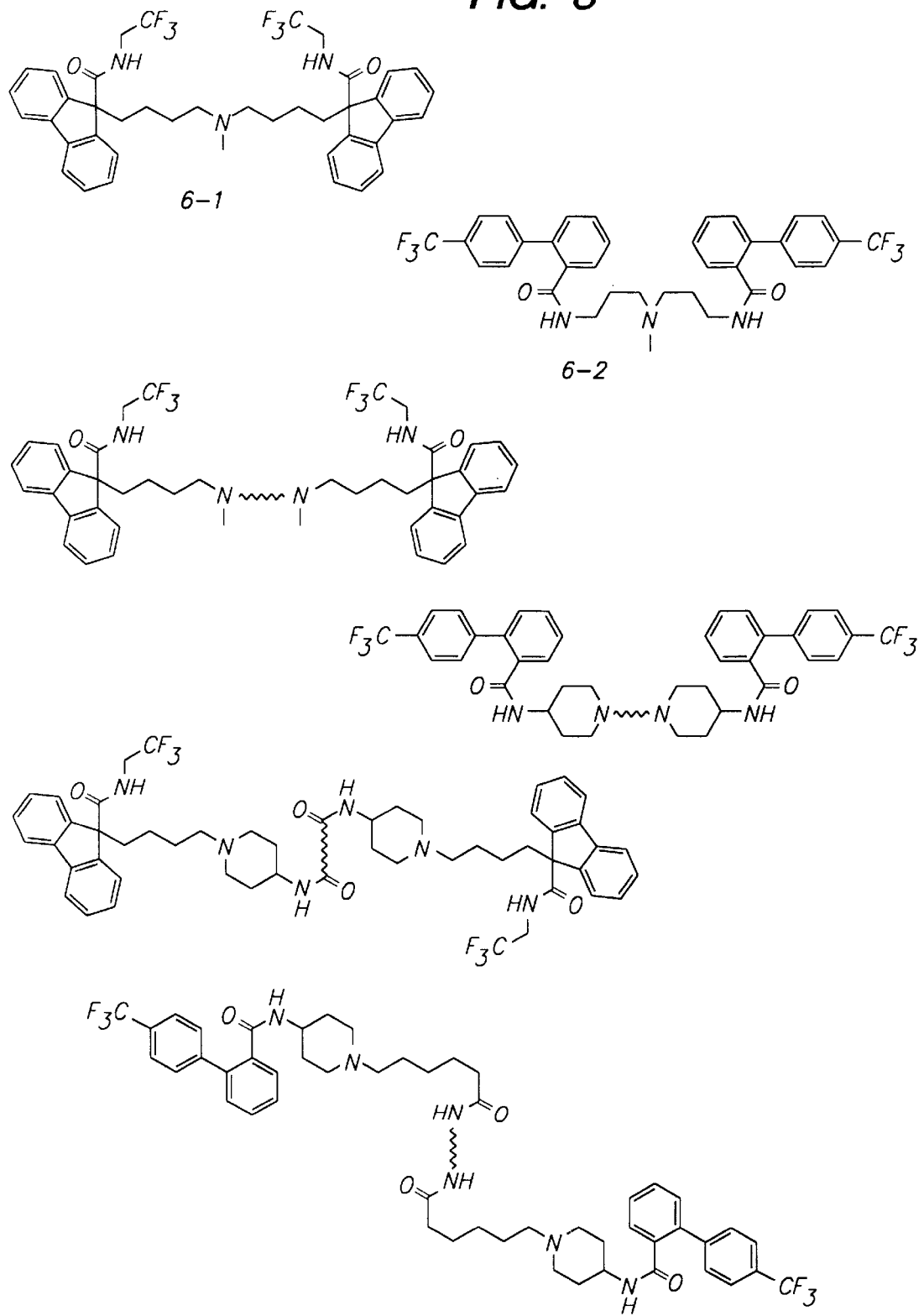

A preferred group of ligands for use in this invention are those ligands having formulae IA–IE. A more preferred group of ligands are those having formulae IIA–IIE. Examples of multibinding compounds of this invention having specific ligands are illustrated in FIGS. 6–8, wherein ~ represents the linker.

Ligands of formula IA–IE and IIA–IIE are either known in the art or can be readily prepared using art-recognized starting materials, reagents and reaction conditions. By way of illustration, the following patents and publications disclose compounds, intermediates and procedures useful in the preparation of ligands of formulae IA–IE and IIA–IIE or related compounds suitable for use in this invention: U.S. Pat. No. 5,712,279, issued Jan. 27, 1998 to Biller et al.; U.S. Pat. No. 5,739,135, issued Apr. 14, 1998 to Biller et al.; U.S. Pat. No. 5,760,246, issued Jun. 2, 1998 to Biller et al.; U.S. Pat. No. 5,827,875, issued Oct. 27, 1998 to Dickson Jr. et al.; U.S. Statutory Invention Registration No. H1729, published May 5, 1998 by Biller et al.; WO 96/40640, published Dec. 19, 1996; WO 97/26240, published Jul. 24, 1997; WO 97/43255, published Nov. 20, 1997; WO 98/03069, published Jan. 29, 1998; WO 98/03174, published Jan. 29, 1998; WO 98/23593, published Jun. 4, 1998; WO 98/27979, published Jul. 2, 1998; WO 98/31225, published Jul. 23, 1998; WO 98/31366, published Jul. 23, 1998; WO 98/31367, published Jul. 23, 1998; and EP 0 643 057 A1, published Mar. 15, 1995. Each of these patents and publications is incorporated herein by reference in its entirety to the same extent as if each individual patent or publication was specifically and individually indicated to be incorporated by reference in its entirety. The syntheses of specific ligands or ligand precursors (i.e., Synthons A–I) are described in further detail in the Examples set forth below.

The compounds of formula I are typically prepared by coupling two or more ligands to a linker using conventional coupling procedures. Such coupling reactions are typically conducted by reacting to complimentary functional groups, such as carboxylic acid and an amine, to form a stable covalent bond, e.g. an amide. Suitable complimentary functional groups are described herein above.

By way of example, two or more ligands containing a carboxylic acid functional group can be coupled with a polyamine to form a polyamide as illustrated in Scheme 1 (where for purposes of illustration, R represents the ligand and R' represents the linking group).

Scheme 1

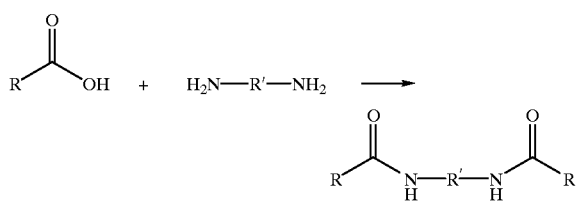

Typically, this reaction is conducted by first activating the carboxylic acid, i.e., by conversion to a carboxylic acid anhydride or acid halide, and then coupling the activated carboxylic acid with a polyamine. For example, a carboxylic acid may be converted into a mixed trifluoroacetic anhydride by contacting the carboxylic acid with one molar equivalent of trifluoroacetic anhydride in an inert diluent, such as THF, at ambient temperature for about 0.5 to 6 hours. The resulting mixed anhydride intermediate is typically not isolated, but is contacted in situ with a polyamine having one molar equivalent of amine groups. This reaction is typically conducted in an inert diluent, such as THF, at a temperature ranging from about 0° C. to about 100° C. for about 1 to 48 hours. Upon completion of the reaction, the compound of formula I is typically isolated and purified using conventional techniques, extraction, precipitation, chromatography, filtration, and the like.

Additionally, if desired, the carboxylic acid can be converted into an acid halide and the acid halide coupled with a polyamine to provide compounds of formula I. Acid halides can be prepared by contacting the carboxylic acid with an inorganic acid halide, such as thionyl chloride, phosphorous trichloride, phosphorous tribromide or phosphorous penta-chloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide is then contacted with a polyamine containing one molar equivalent of amino groups in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of formula I is recovered by conventional methods including neutralization, extraction, precipitation, chromatography, filtration, and the like.

Alternatively, the carboxylic acid may be directed coupled with the polyamine using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethylamino-propyl)-3-ethylcarbodiimide (EDC) and the like. If desired, polymer supported forms of carbodiimide coupling reagents may also be used including, for example, those described in Tetrahedron Letters, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the carboxylic acid with about 1 to about 2 equivalents of the coupling reagent and with a polyamine containing one molar equivalent of amino groups in an inert diluent, such as dichloromethane, chloroform, acetonitrile, tetrahydrofuran, N,N-dimethylformamide and the like. Generally, this reaction is conducted at a temperature ranging from about 0°C. to about 37° C. for about 12 to about 24 hours. Upon completion of the reaction, the compound of formula I is recovered by conventional methods including neutralization, extraction, precipitation, chromatography, filtration, and the like.

Compounds of formula I can also be prepared by reacting two or more ligands containing a primary or secondary amine functional group with an alkyl poly(halide) to form a polyamine as shown in Scheme 2 (where for purposes of illustration, R represents a portion of the ligand or hydrogen and R' represents the linking group).

Scheme 2

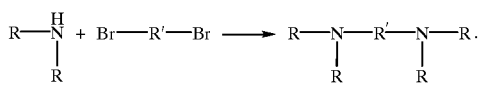

This coupling reaction is typically conducted by contacting the amine compound with a suitable alkali or alkaline earth metal base, such as potassium carbonate, in an inert diluent, such as DMF and the like, in the presence of a alkyl poly(halide) having one molar equivalent halide groups. Generally, this reaction is conducted at a temperature ranging from about 25° C. to about 100° C. for about 24 to about 72 hours. Optionally, a catalytic amount of sodium or potassium iodide may be added to the reaction mixture when an alkyl poly(chloride) or poly(bromide) is employed in the reaction. Upon completion of the reaction, the compound of formula I is recovered by conventional methods including neutralization, extraction, precipitation, chromatography, filtration, and the like.

Other methods and reaction conditions for preparing compounds of formula I are described in further detail in the Examples set forth below. As will be readily apparent to those of ordinary skill in the art, the synthetic procedures described herein or those known in the art may be readily modified to afford a wide variety of compounds within the scope of this invention.

Combinatorial Libraries

The methods described herein lend themselves to combinatorial approaches for identifying multimeric compounds which possess multibinding properties.

Specifically, factors such as the proper juxtaposition of the individual ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of Ligand(s)

A single ligand or set of ligands is (are) selected for incorporation into the libraries of candidate multibinding compounds which library is directed against a particular biological target or targets, i.e., inhibition of MTP. The only requirement for the ligands chosen is that they are capable of interacting with the selected target(s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, logP, etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of Ligand Attachment Points and Linking Chemistry

Several points are chosen on each ligand at which to attach the ligand to the linker. The selected points on the ligand/linker for attachment are functionalized to contain complementary reactive functional groups. This permits probing the effects of presenting the ligands to their target binding site(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a ligand bound to its target allows one to identify one or more sites where linker attachment will not preclude the ligand/target interaction. Alternatively, evaluation of ligand/target binding by nuclear magnetic resonance will permit the identification of sites non-essential for ligand/target binding. See, for example, Fesik, et al., U.S. Pat. No. 5,891,643, the disclosure of which is incorporated herein by reference in its entirety. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a ligand bound to its target, and then consider modifying this ligand by attaching to it a second copy of the same ligand with a linker which allows the second ligand to interact with the same target at sites proximal to the first binding site, which include elements of the target that are not part of the formal ligand binding site and/or elements of the matrix surrounding the formal binding site, such as the membrane. Here, the most favorable orientation for interaction of the second ligand molecule may be achieved by attaching it to the linker at a position which abrogates activity of the ligand at the first binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heterodimeric constructs bearing two different ligands that bind to common or different targets.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically innocuous under typical chemical and physiological conditions, and compatible with a large number of available linkers. Amide bonds, ethers, amines, carbamates, ureas, and sulfonamides are but a few examples of preferred linkages.

Linker Selection

In the library of linkers employed to generate the library of candidate multibinding compounds, the selection of linkers employed in this library of linkers takes into consideration the following factors:

Valency: In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length: Linkers are chosen in a range of lengths to allow the spanning of a range of inter-ligand distances that encompass the distance preferable for a given divalent interaction. In some instances the preferred distance can be estimated rather precisely from high-resolution structural information of targets. In other instances where high-resolution structural information is not available, one can make use of simple models to estimate the maximum distance between binding sites either on adjacent receptors or at different locations on the same receptor. In situations where two binding sites are present on the same target (or target subunit for multisubunit targets), preferred linker distances are 2–20 Å, with more preferred linker distances of 3–12 Å. In situations where two binding sites reside on separate target sites, preferred linker distances are 20–100 Å, with more preferred distances of 30–70 Å.

Linker Geometry and Rigidity: The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties: The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups: Linker chemical functional groups are selected to be compatible with the chemistry chosen to connect linkers to the ligands and to impart the range of physical properties sufficient to span initial examination of this parameter.

Combinatorial Synthesis

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters for a particular target. For example, an array generated from two ligands, one which has two attachment points (A1, A2) and one which has three attachment points (B1, B2, B3) joined in all possible combinations provide for at least 15 possible combinations of multibinding compounds:

| A1-A1 | A1-A2 | A1-B1 | A1-B2 | A1-B3 | A2-A2 | A2-B1 | A2-B2 |
| A2-B3 | B1-B1 | B1-B2 | B1-B3 | B2-B2 | B2-B3 | B3-B3 | |

When each of these combinations is joined by 10 different linkers, a library of 150 candidate multibinding compounds results.

Given the combinatorial nature of the library, common chemistries are preferably used to join the reactive functionalities on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of the Library

Various methods are used to characterize the properties and activities of the candidate multibinding compounds in the library to determine which compounds possess multibinding properties. Physical constants such as solubility under various solvent conditions and logD/clogD values are determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, are also determined. Pharmacological data, including oral absorption, everted gut penetration, other pharmacokinetic parameters and efficacy data are determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libaries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up Synthesis and Analysis of Additional Libraries

Based on the information obtained through analysis of the initial library, an optional component of the process is to ascertain one or more promising multibinding "lead" compounds as defined by particular relative ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| Representative Complementary Binding Chemistries | | |
|---|---|---|
| First Reactive Group | Second Reactive Group | Linkage |
| hydroxyl | isocyanate | carbamate |
| amine | epoxide | β-hydroxyamine |
| sulfonyl halide | amine | sulfonamide |
| carboxyl acid | amine | amide |
| hydroxyl | alkyl/aryl halide | ether |
| aldehyde | amine(+ reducing agent) | amine |
| ketone | amine(+ reducing agent) | amine |
| amine | isocyanate | urea |

Exemplary linkers are derived by reaction of the following compounds identified as X-1 though X-418 as set forth below with a complementary reactive group as set forth above:

Diacids

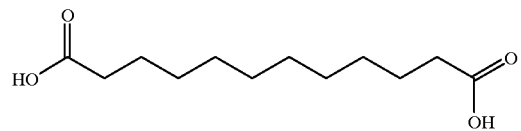

X-1

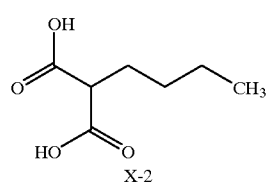

X-2

-continued
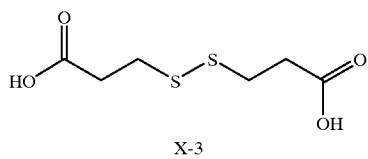
X-3
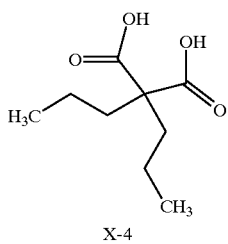
X-4
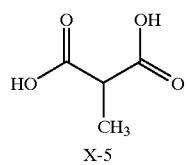
X-5
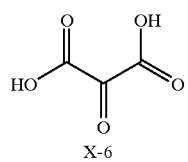
X-6
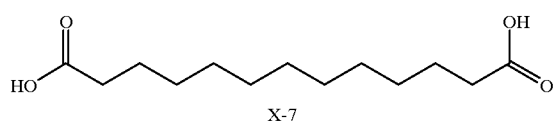
X-7
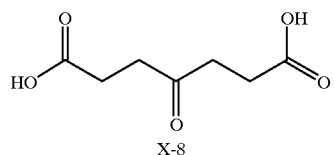
X-8
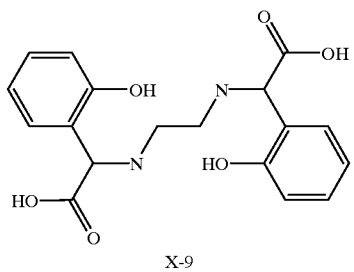
X-9
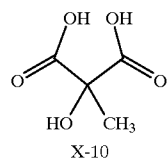
X-10

-continued
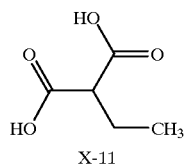
X-11
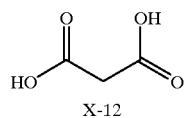
X-12
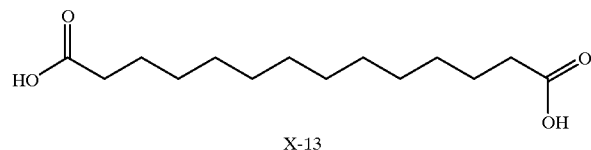
X-13
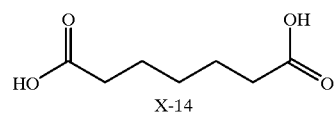
X-14
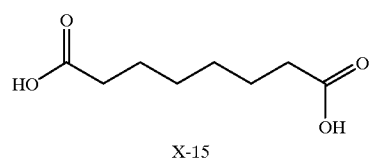
X-15
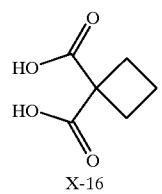
X-16
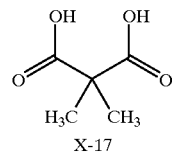
X-17
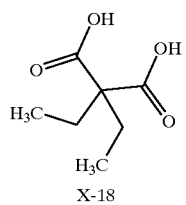
X-18
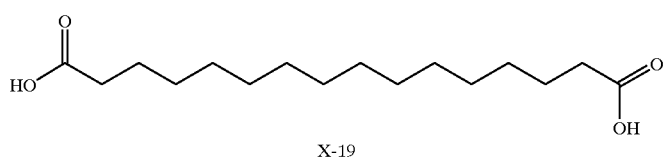
X-19

-continued
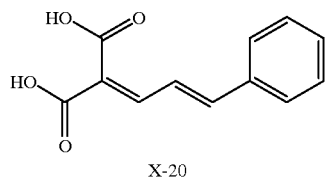
X-20
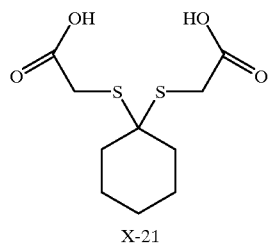
X-21
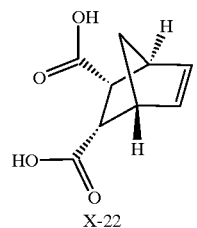
X-22
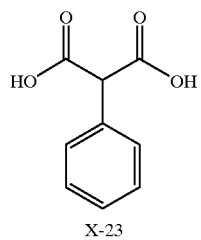
X-23
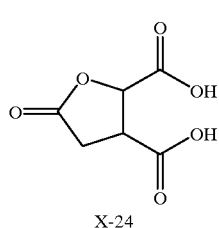
X-24
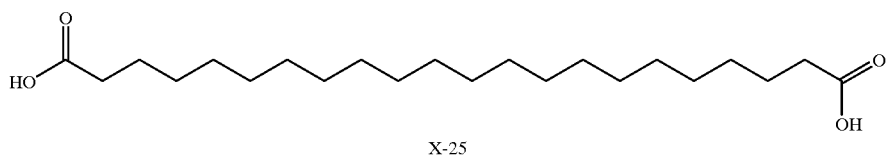
X-25
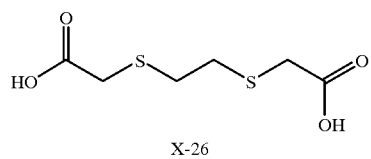
X-26

-continued
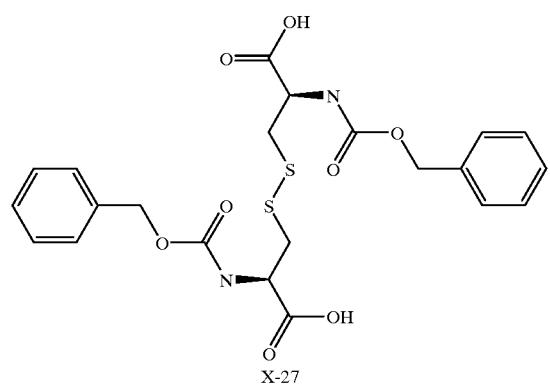
X-27
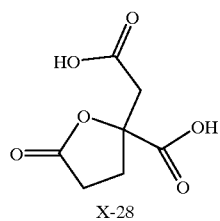
X-28
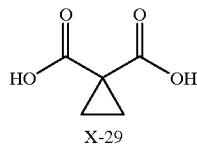
X-29
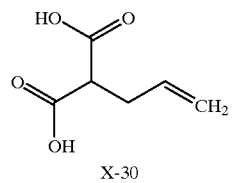
X-30
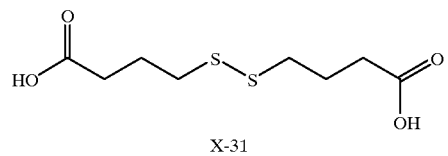
X-31
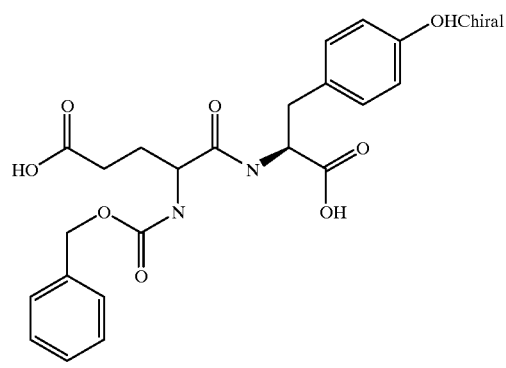
X-32

-continued
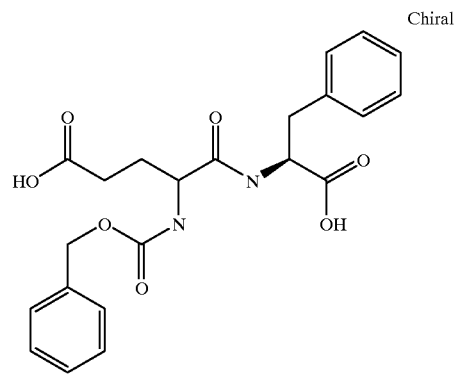
X-33
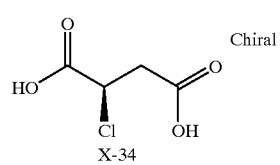
X-34
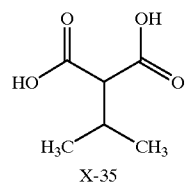
X-35
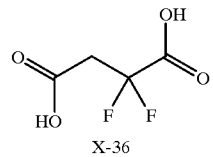
X-36
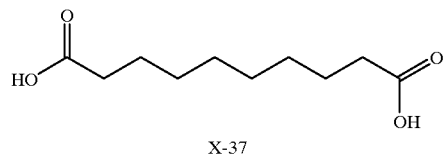
X-37
X-38

-continued
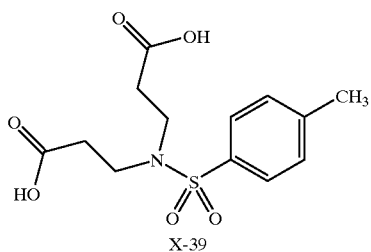
X-39
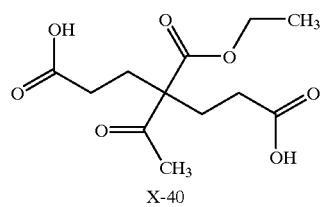
X-40
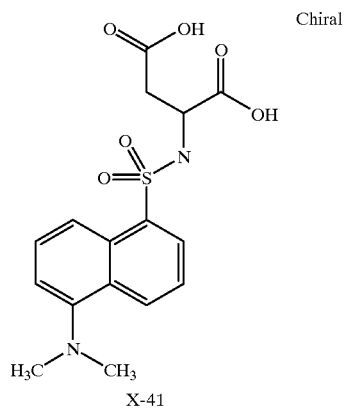
X-41
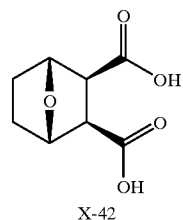
X-42
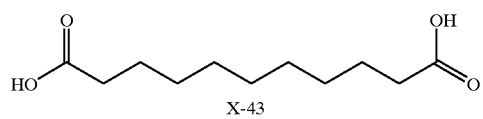
X-43
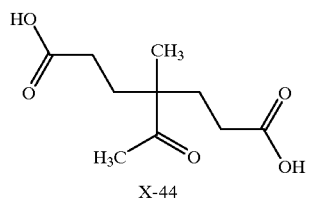
X-44

-continued
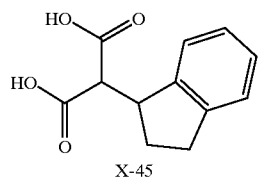
X-45
Chiral
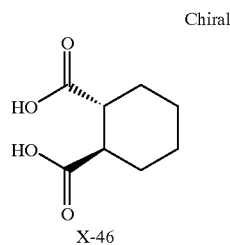
X-46
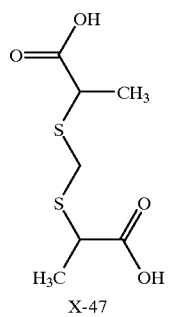
X-47
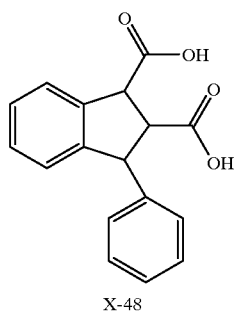
X-48
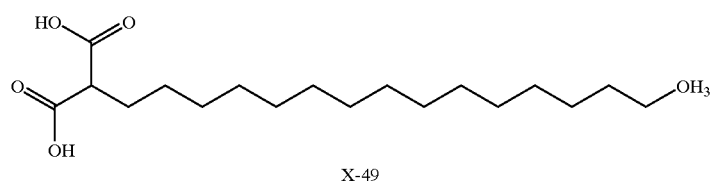
X-49
Chiral
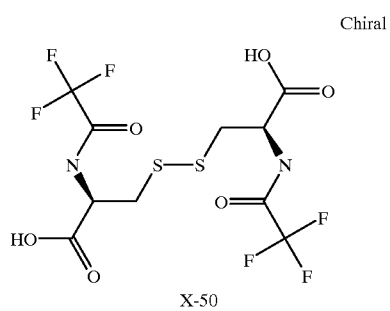
X-50

-continued
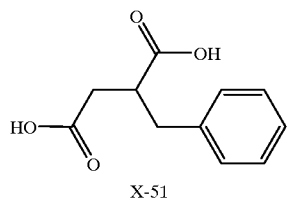
X-51
Chiral
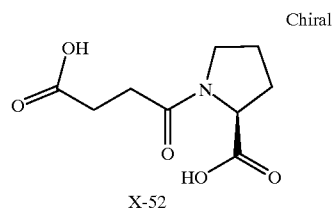
X-52
Chiral
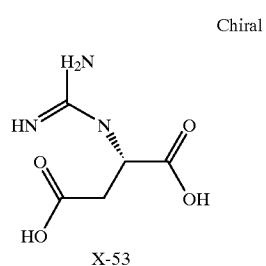
X-53
Chiral
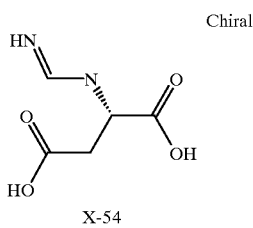
X-54
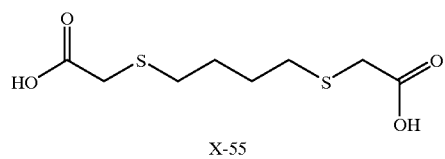
X-55
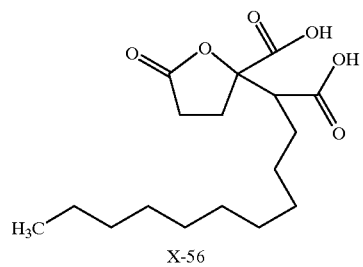
X-56
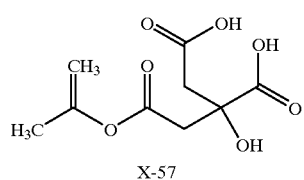
X-57

-continued
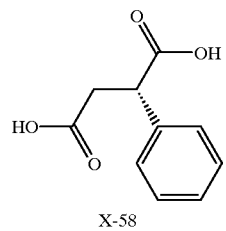
X-58
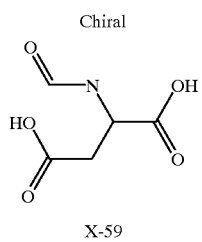
X-59
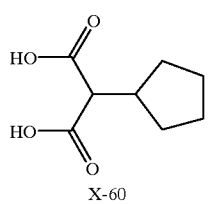
X-60
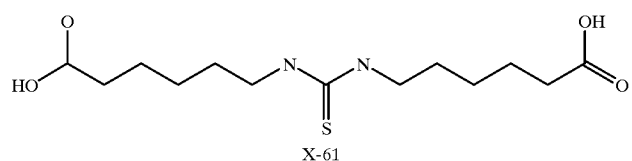
X-61
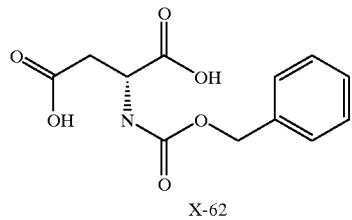
X-62
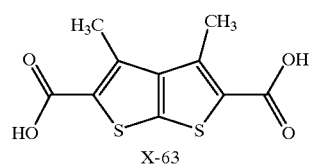
X-63
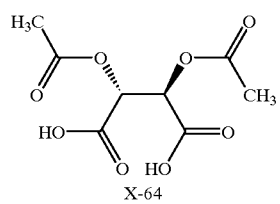
X-64

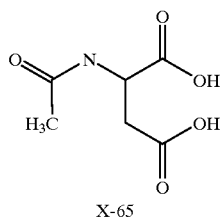
X-65
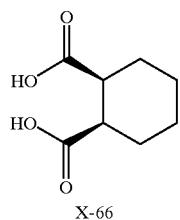
X-66
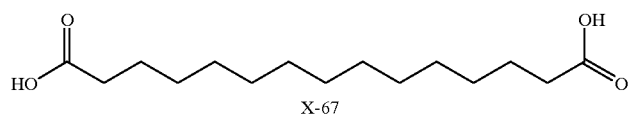
X-67
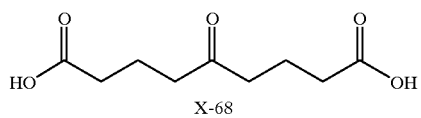
X-68
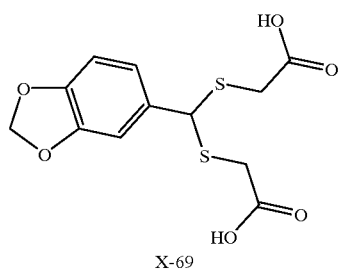
X-69
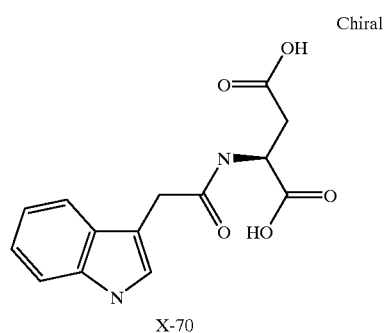
X-70
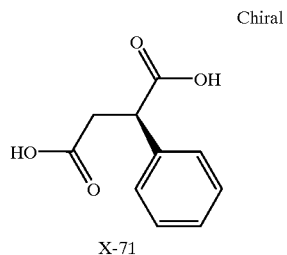
X-71

-continued
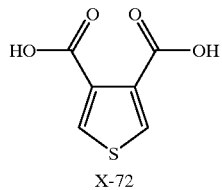
X-72
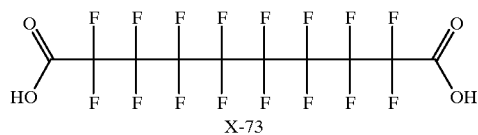
X-73
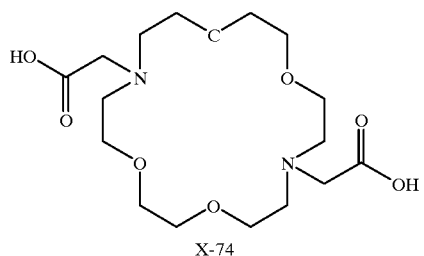
X-74
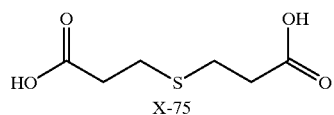
X-75
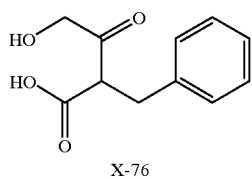
X-76
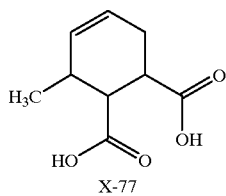
X-77
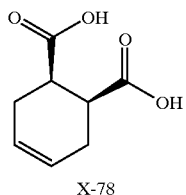
X-78
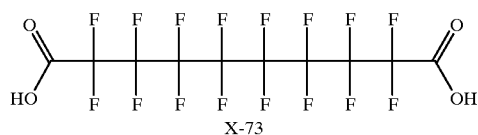
X-73

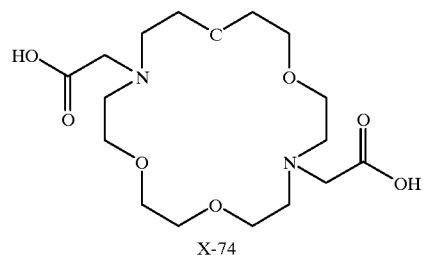
X-74
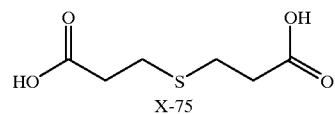
X-75
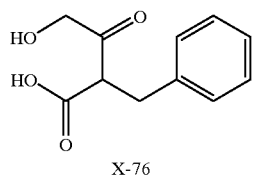
X-76
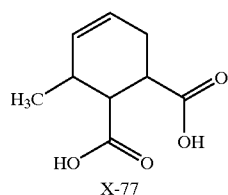
X-77
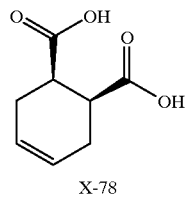
X-78
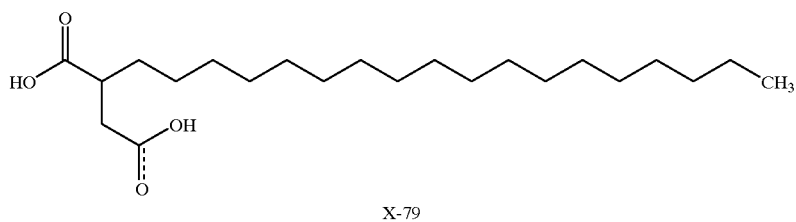
X-79
Chiral
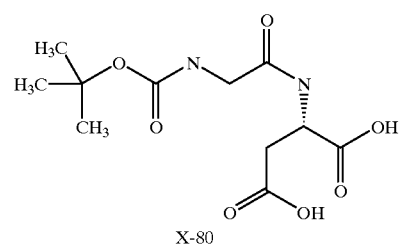
X-80

-continued
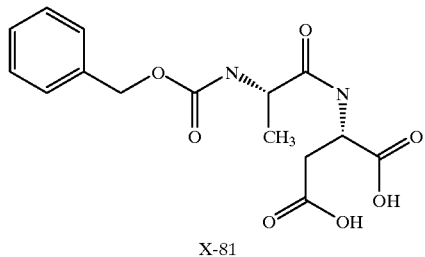
X-81
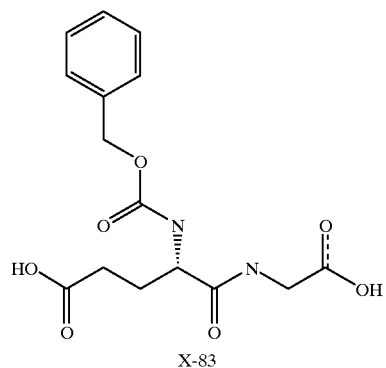
X-83
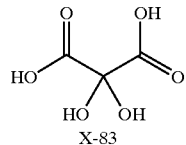
X-83
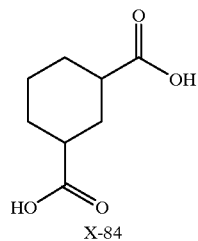
X-84
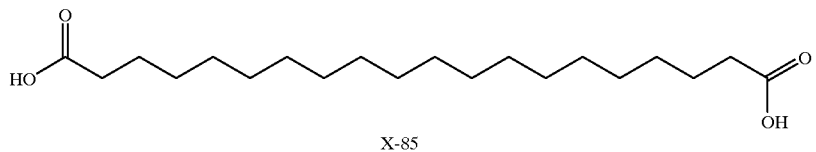
X-85

-continued
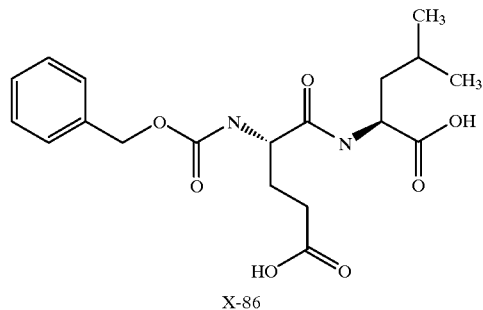
X-86
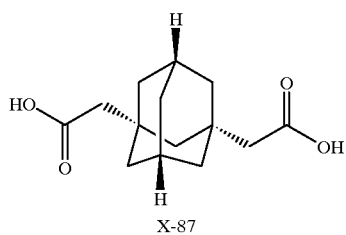
X-87
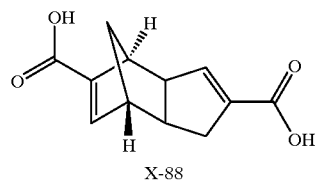
X-88
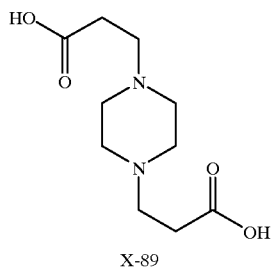
X-89
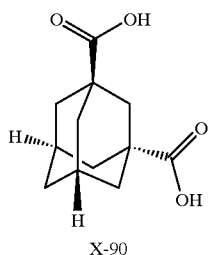
X-90

-continued
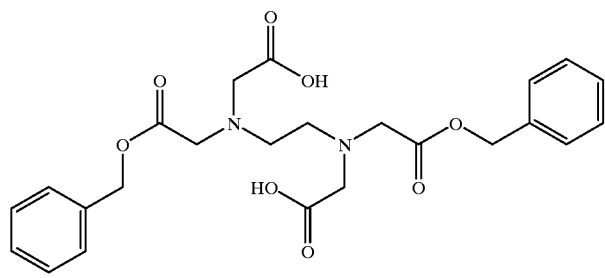
X-91
Chiral
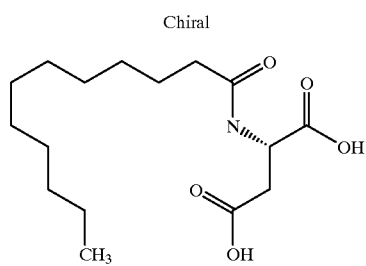
X-92
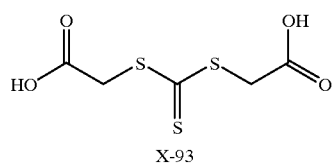
X-93
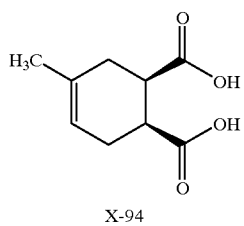
X-94
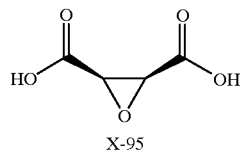
X-95
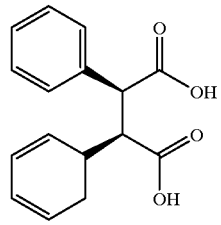
X-96

-continued
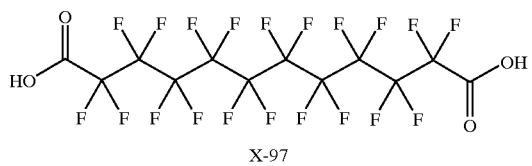
X-97
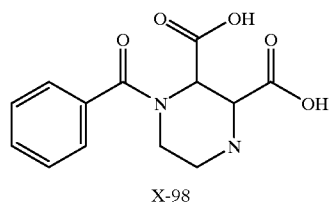
X-98
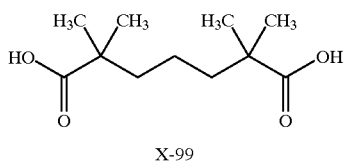
X-99
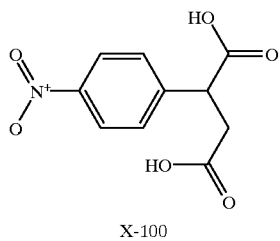
X-100
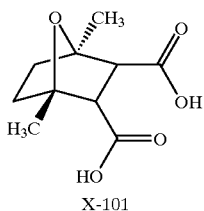
X-101
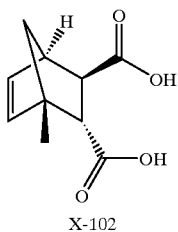
X-102
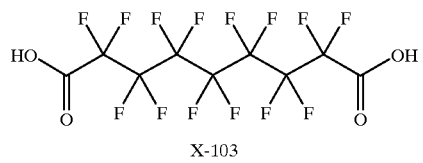
X-103

-continued
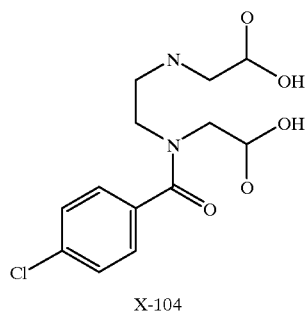
X-104
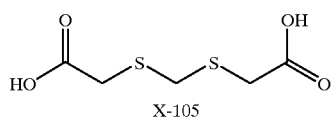
X-105
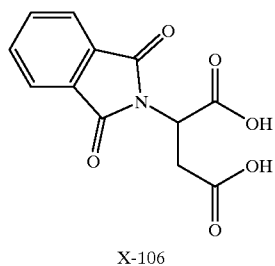
X-106
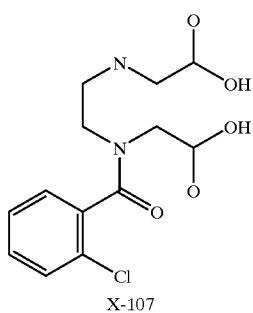
X-107
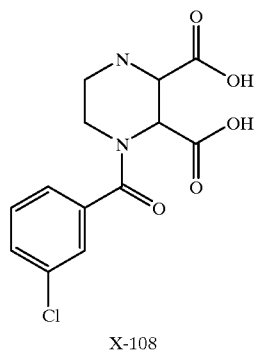
X-108
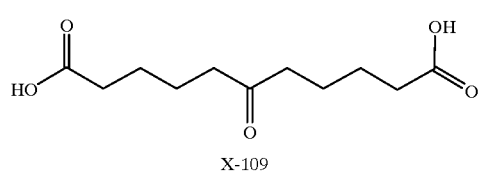
X-109

-continued
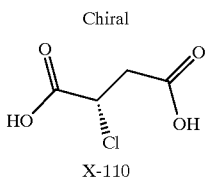
X-110
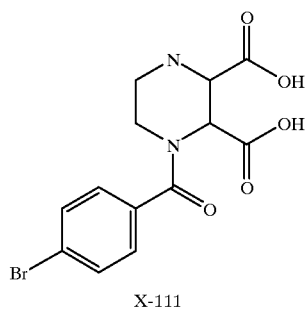
X-111
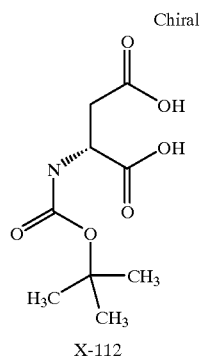
X-112
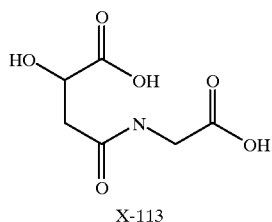
X-113
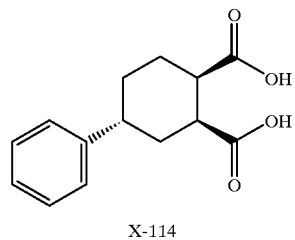
X-114

-continued
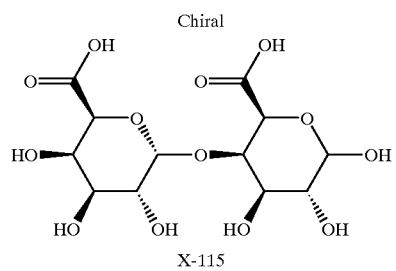
X-115
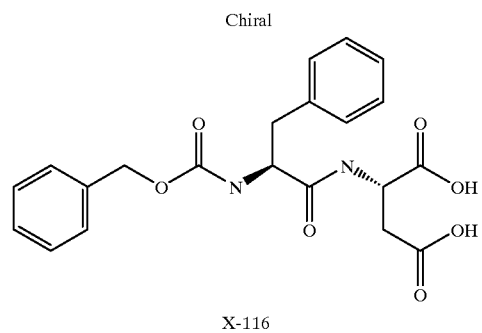
X-116
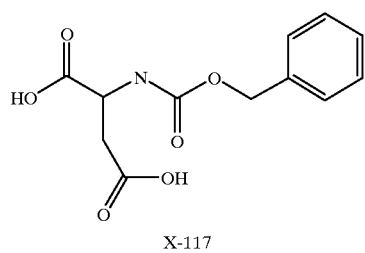
X-117
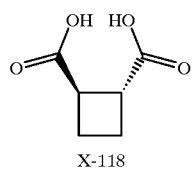
X-118
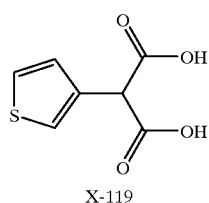
X-119
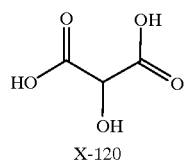
X-120
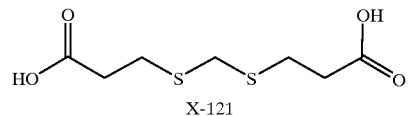
X-121

-continued
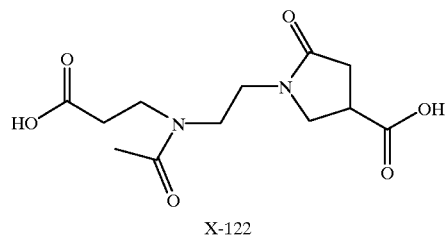
X-122
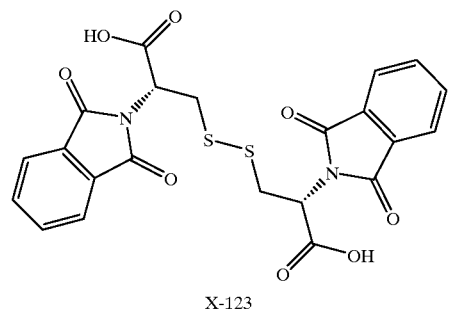
X-123
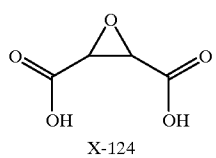
X-124
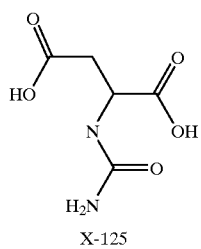
X-125
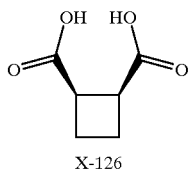
X-126
Chiral
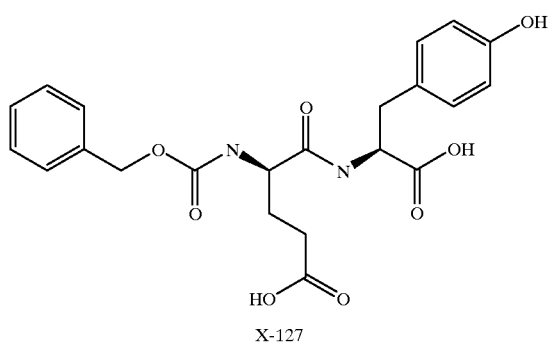
X-127

-continued
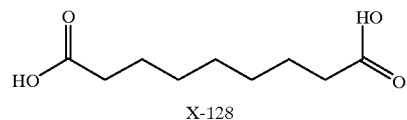
X-128
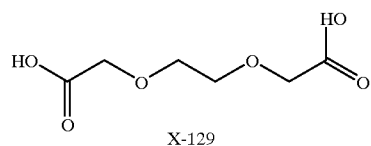
X-129
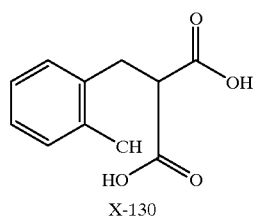
X-130
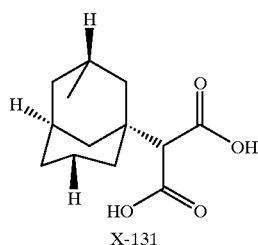
X-131
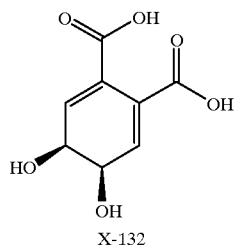
X-132
Disulfonyl Halides
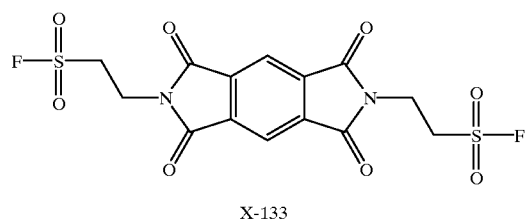
X-133
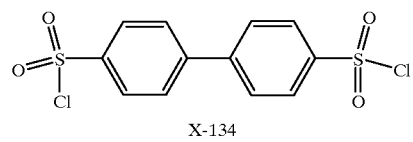
X-134

-continued
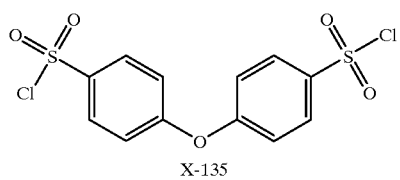
X-135
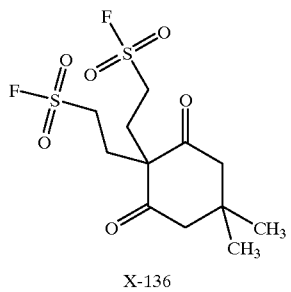
X-136
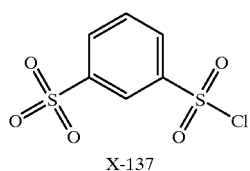
X-137
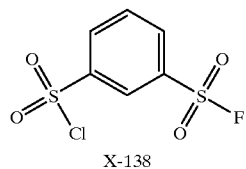
X-138
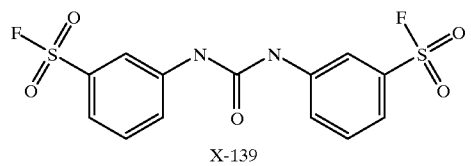
X-139
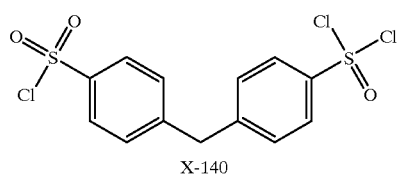
X-140
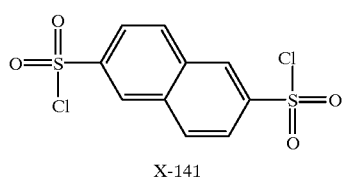
X-141

-continued
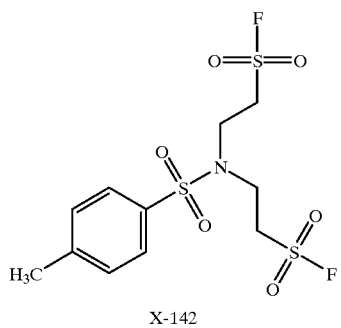
X-142
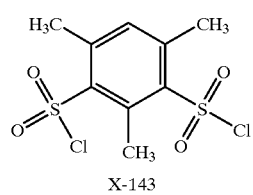
X-143
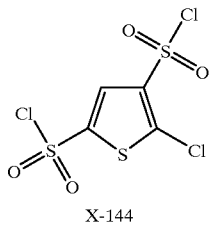
X-144
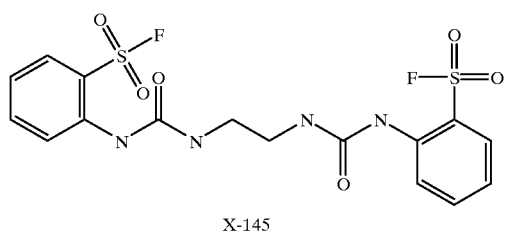
X-145
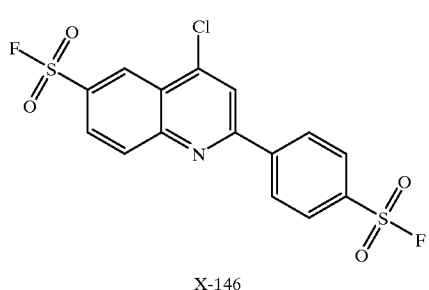
X-146
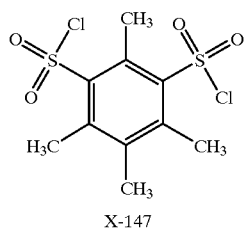
X-147

-continued
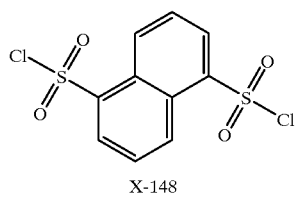
X-148
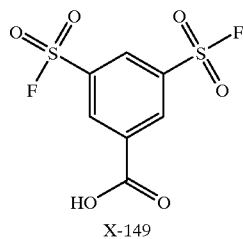
X-149
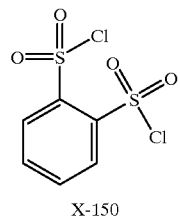
X-150
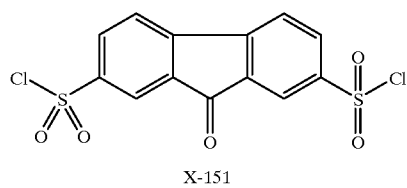
X-151
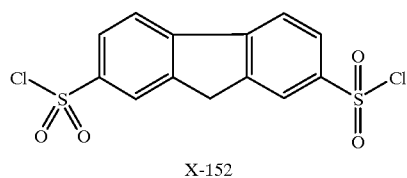
X-152
Dialdehydes
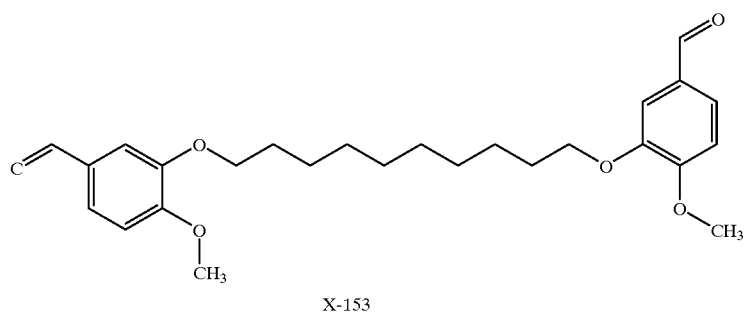
X-153
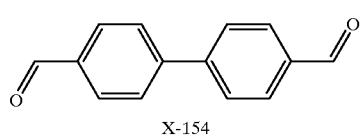
X-154

-continued
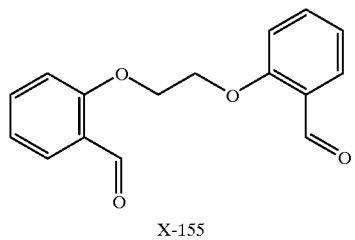
X-155
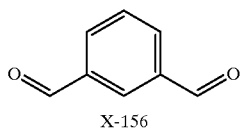
X-156
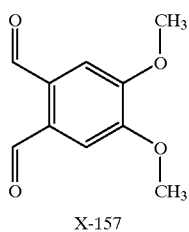
X-157
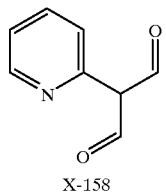
X-158
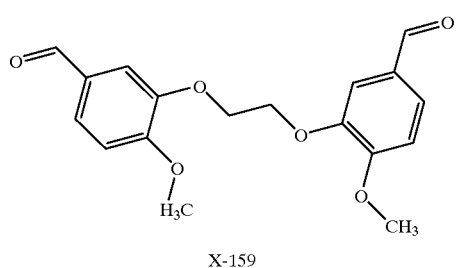
X-159
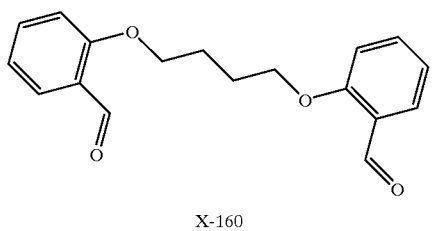
X-160
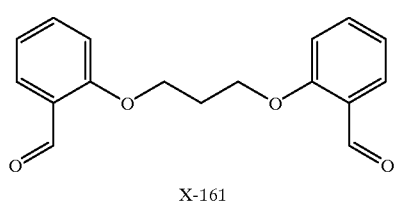
X-161

-continued
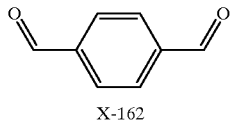
X-162
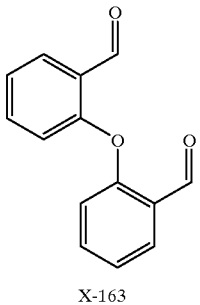
X-163
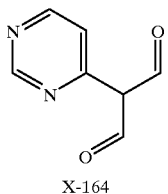
X-164
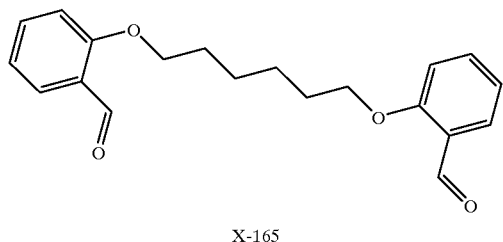
X-165
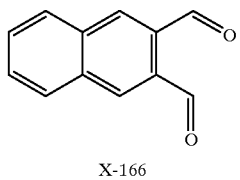
X-166
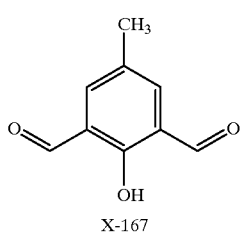
X-167
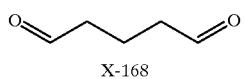
X-168

-continued
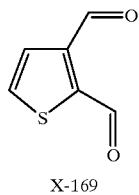
X-169
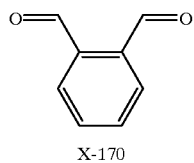
X-170
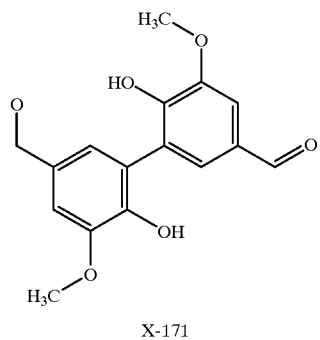
X-171
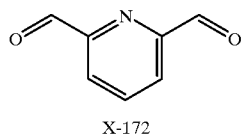
X-172
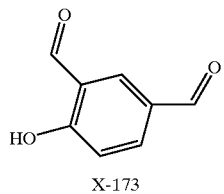
X-173
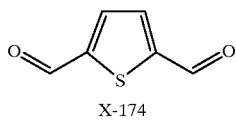
X-174
Dihalides
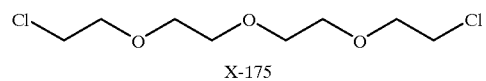
X-175

-continued
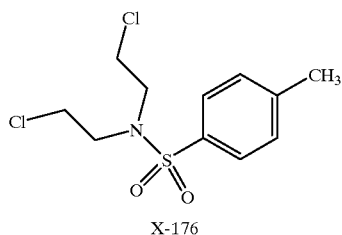
X-176
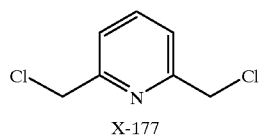
X-177
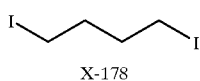
X-178
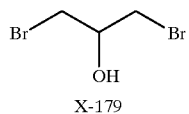
X-179
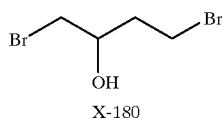
X-180
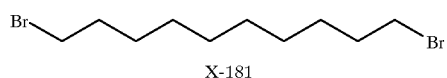
X-181
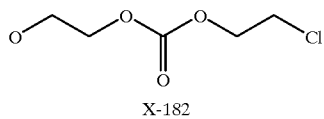
X-182
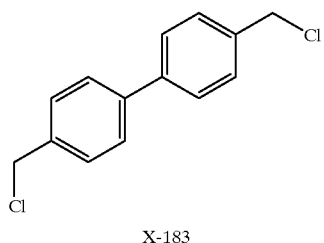
X-183
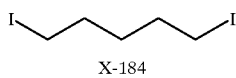
X-184
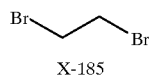
X-185
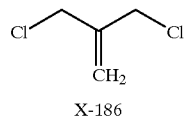
X-186

-continued
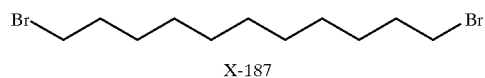
X-187
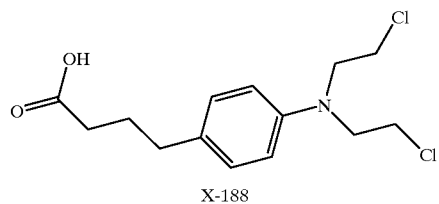
X-188
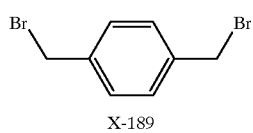
X-189
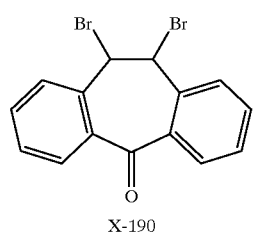
X-190
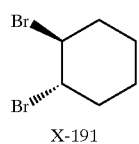
X-191
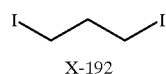
X-192
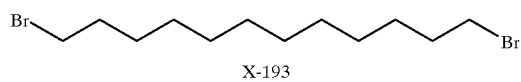
X-193
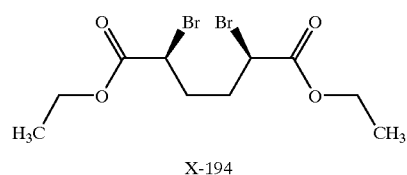
X-194
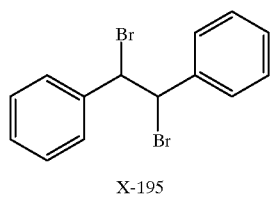
X-195
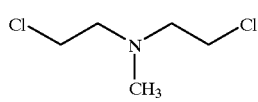
X-196

-continued
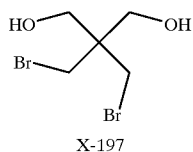
X-197
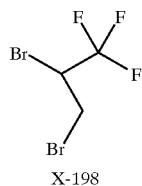
X-198
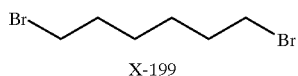
X-199
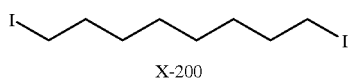
X-200
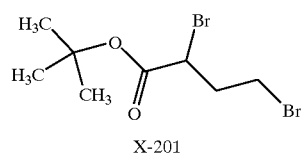
X-201
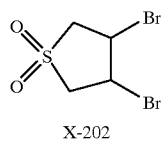
X-202
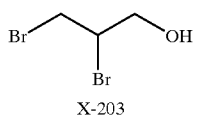
X-203
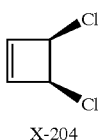
X-204
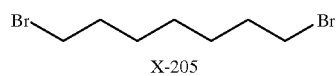
X-205
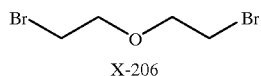
X-206
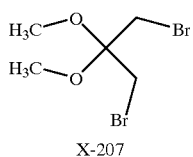
X-207

-continued
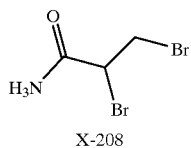
X-208
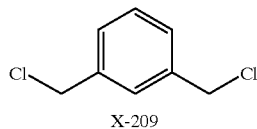
X-209
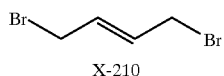
X-210
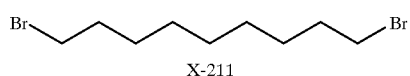
X-211
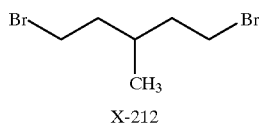
X-212
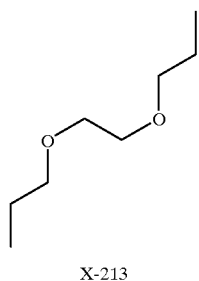
X-213
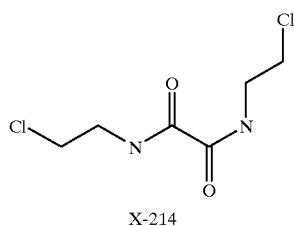
X-214
Diisocyanates
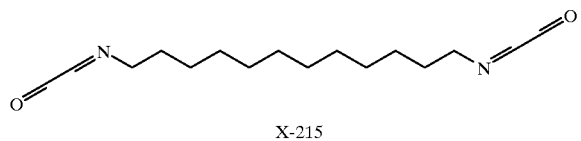
X-215
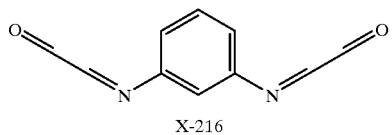
X-216

-continued
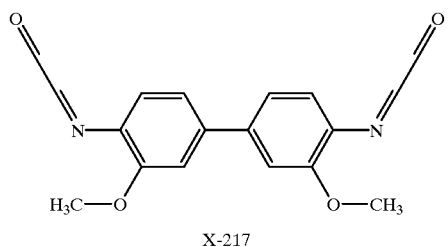
X-217
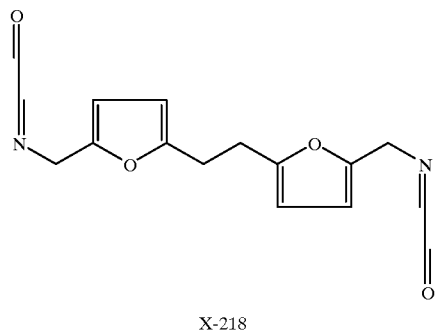
X-218
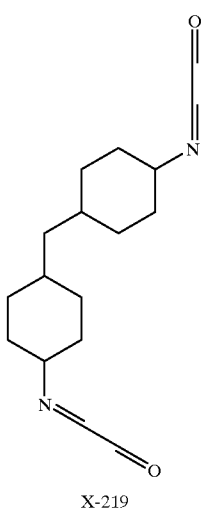
X-219
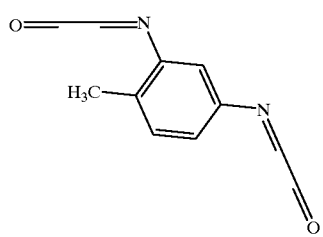
X-220
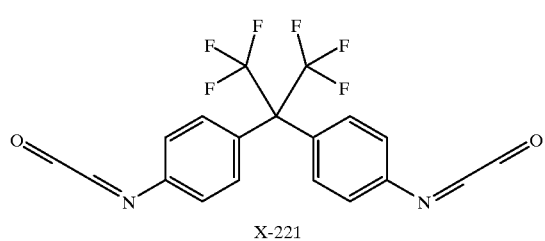
X-221

-continued
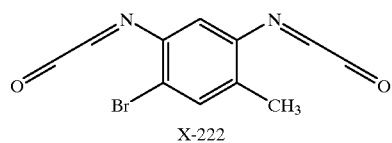
X-222
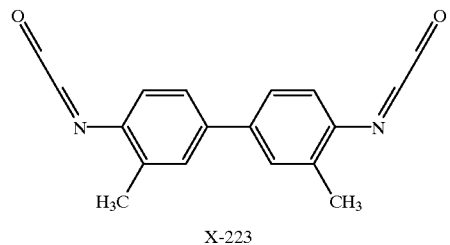
X-223
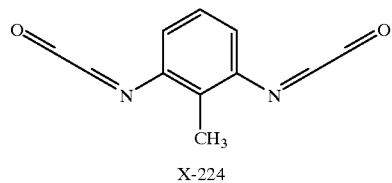
X-224
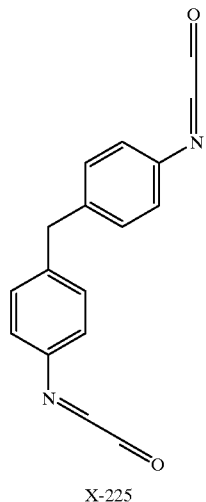
X-225
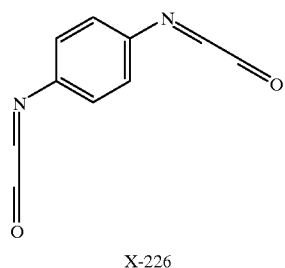
X-226

-continued
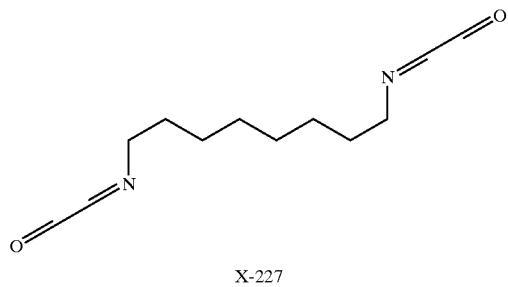
X-227
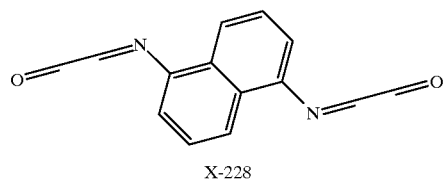
X-228
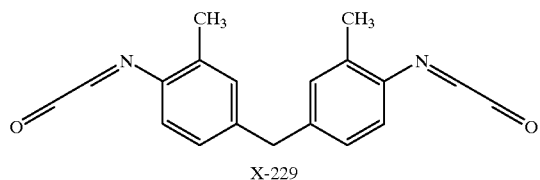
X-229
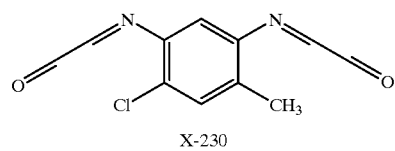
X-230
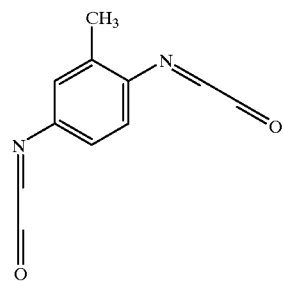
X-231
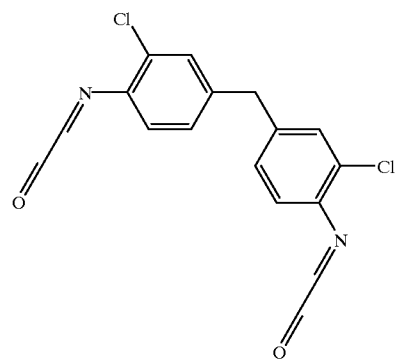
X-232

-continued
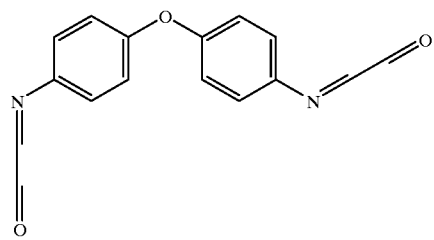
X-233
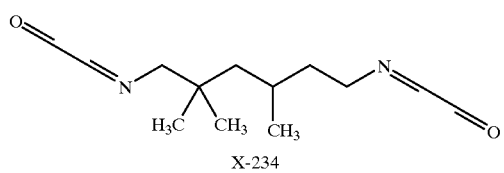
X-234
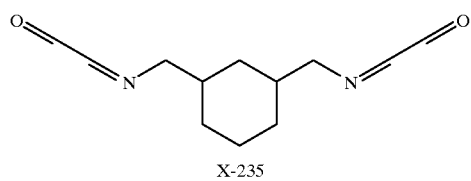
X-235
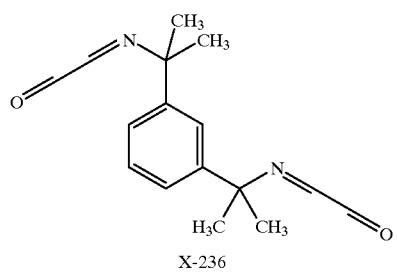
X-236
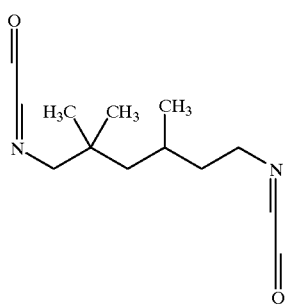
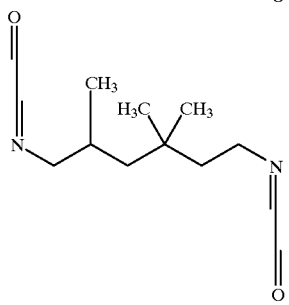
X-237

-continued
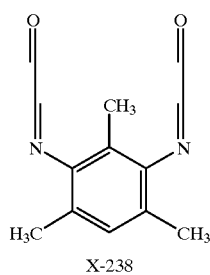
X-238
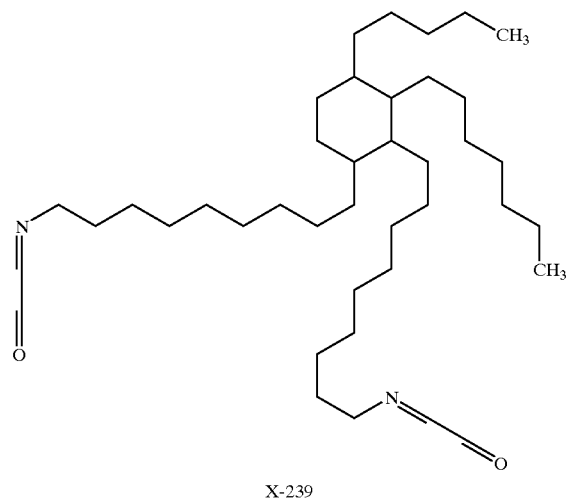
X-239
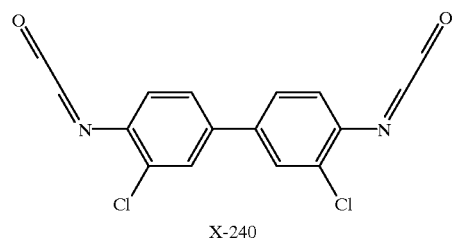
X-240
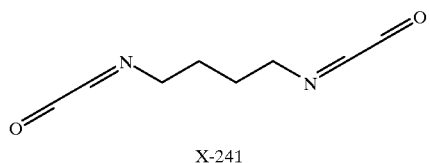
X-241
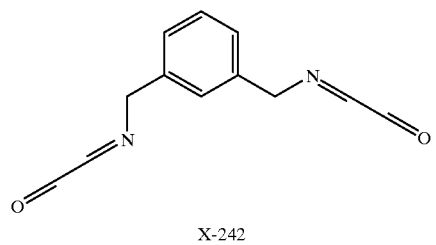
X-242

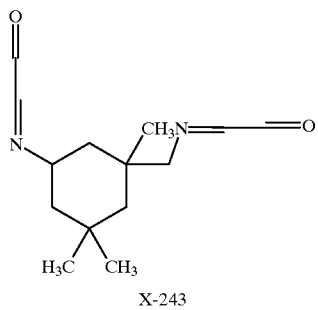
X-243
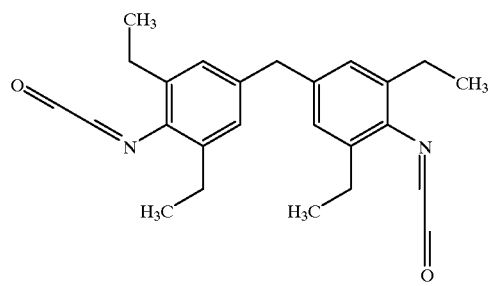
X-244
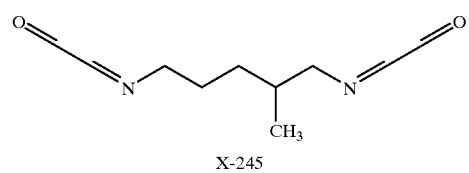
X-245
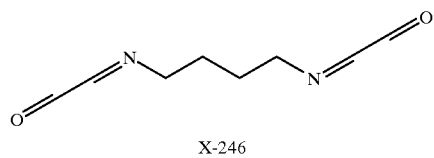
X-246
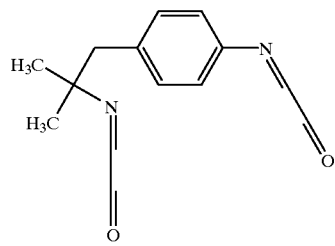
X-247
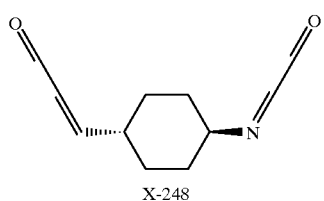
X-248
Diamines -continued
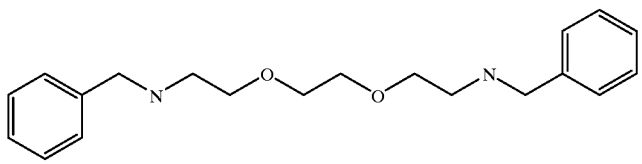
X-249
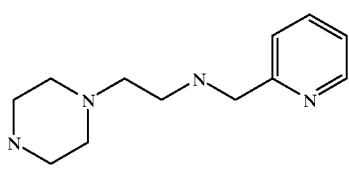
X-250
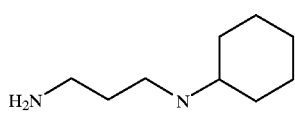
X-251
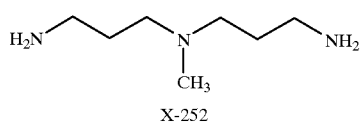
X-252
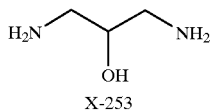
X-253
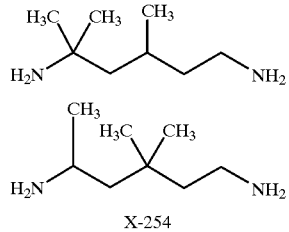
X-254
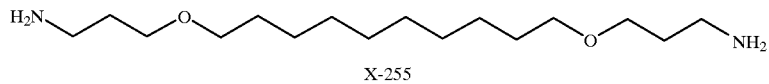
X-255
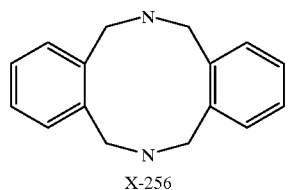
X-256
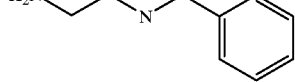
X-257

-continued
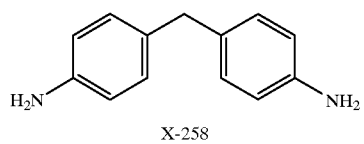
X-258
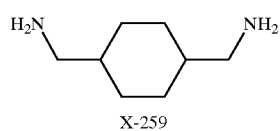
X-259
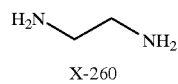
X-260
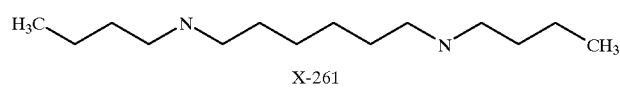
X-261
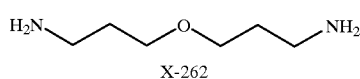
X-262
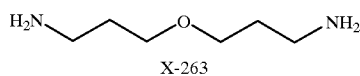
X-263
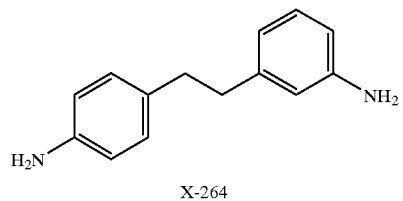
X-264
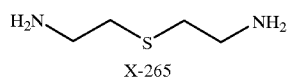
X-265
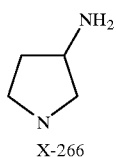
X-266
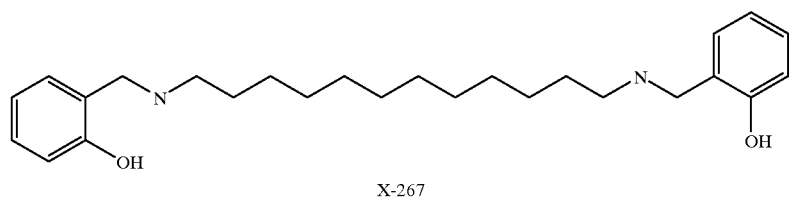
X-267
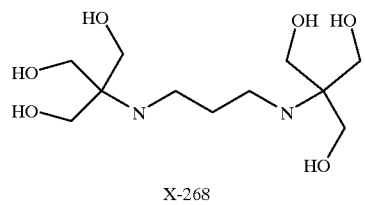
X-268

-continued
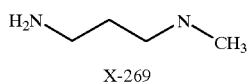
X-269
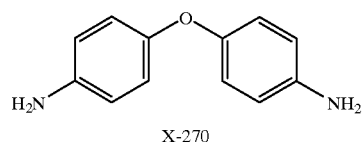
X-270
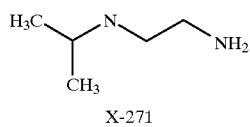
X-271
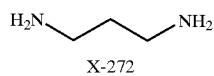
X-272
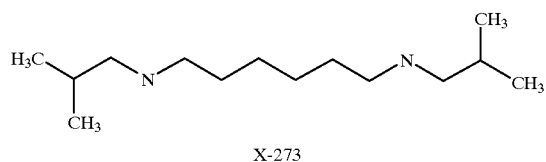
X-273
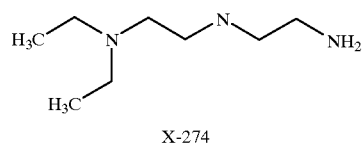
X-274
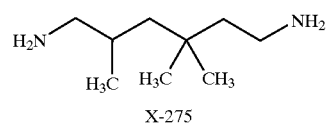
X-275
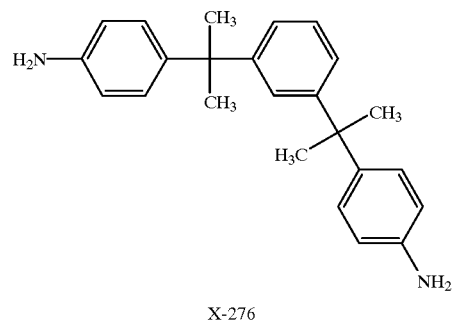
X-276
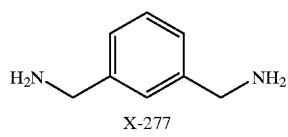
X-277

-continued
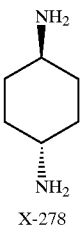
X-278
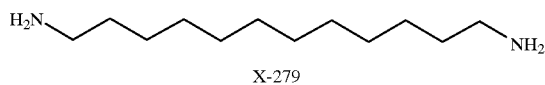
X-279
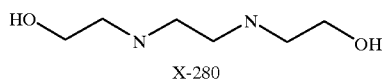
X-280
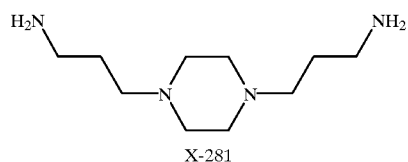
X-281
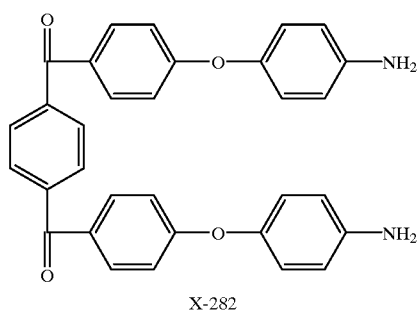
X-282
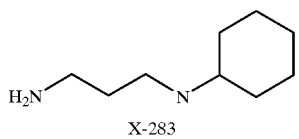
X-283
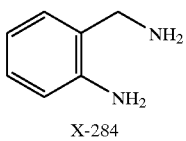
X-284
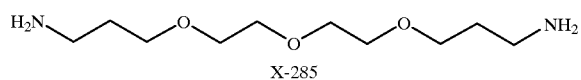
X-285
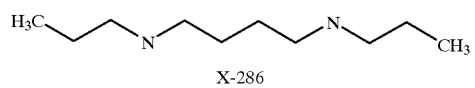
X-286
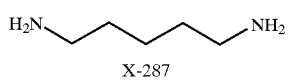
X-287

-continued
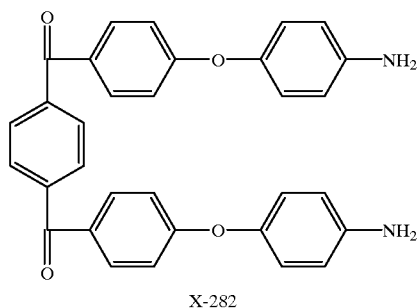
X-282
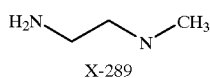
X-289
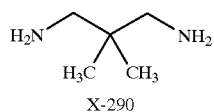
X-290
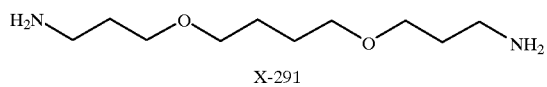
X-291
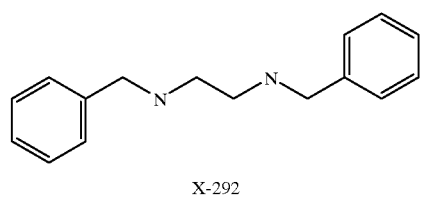
X-292
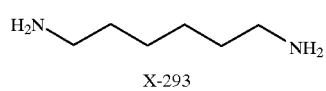
X-293
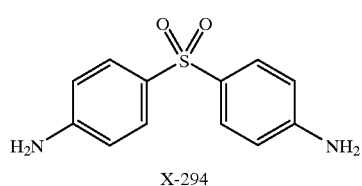
X-294
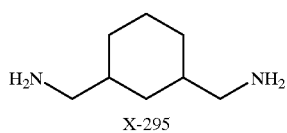
X-295
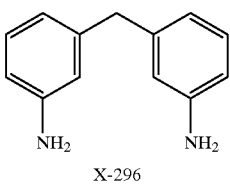
X-296

-continued
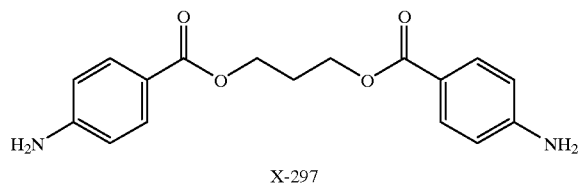
X-297
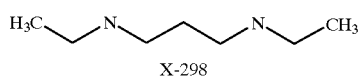
X-298
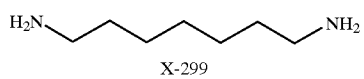
X-299
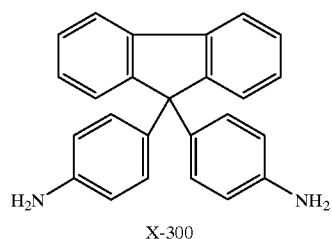
X-300
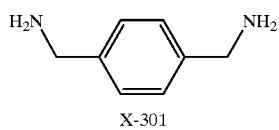
X-301
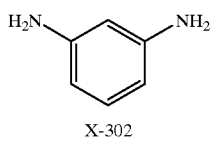
X-302
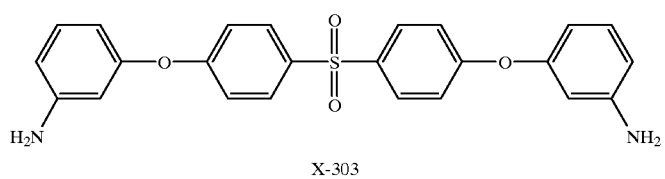
X-303
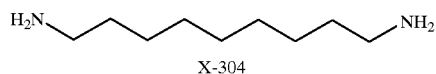
X-304
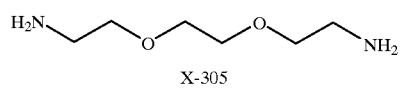
X-305
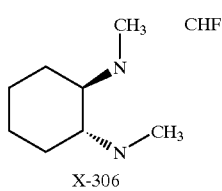
X-306
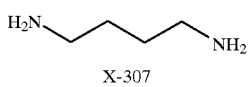
X-307

-continued
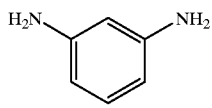
X-302
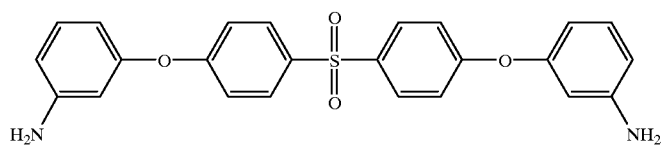
X-303
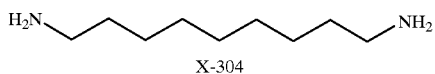
X-304
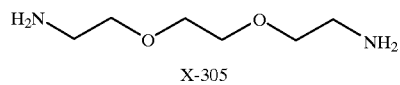
X-305
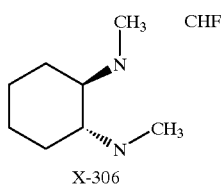
X-306
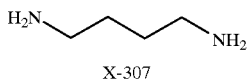
X-307
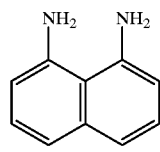
X-308
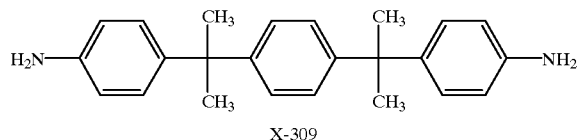
X-309
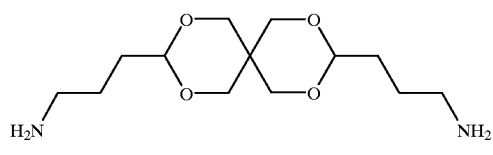
X-310
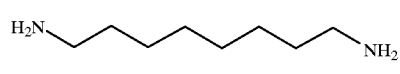
X-311

-continued
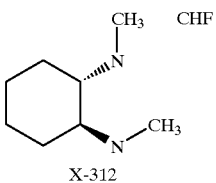
X-312
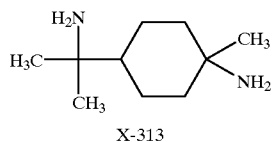
X-313
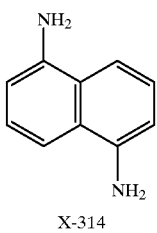
X-314
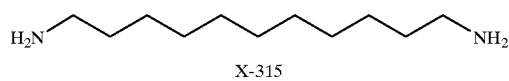
X-315
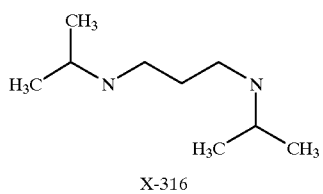
X-316
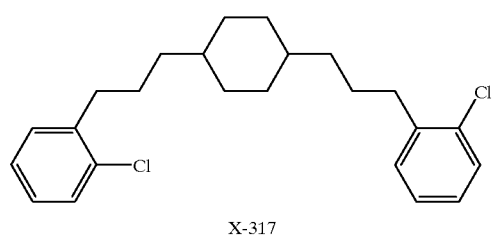
X-317
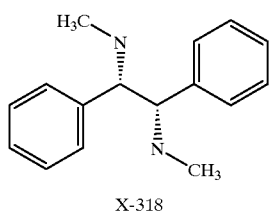
X-318
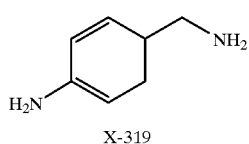
X-319

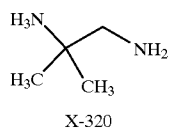
X-320
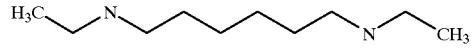
X-321
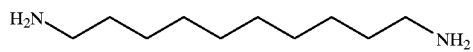
X-322
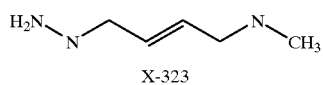
X-323
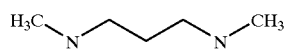
X-324
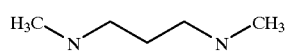
X-325
Diols
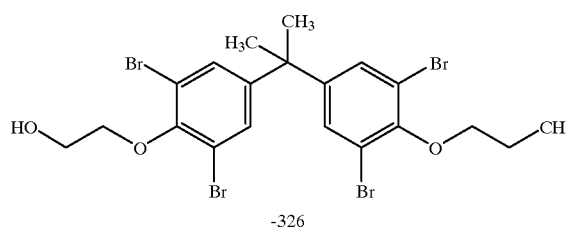
-326
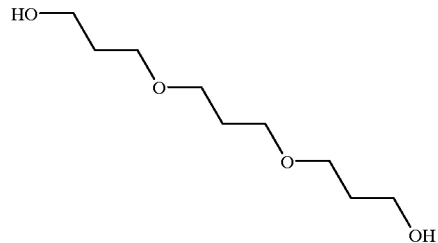
X-327
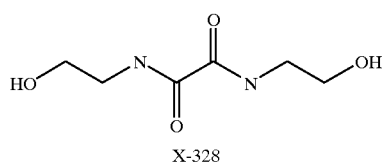
X-328

-continued
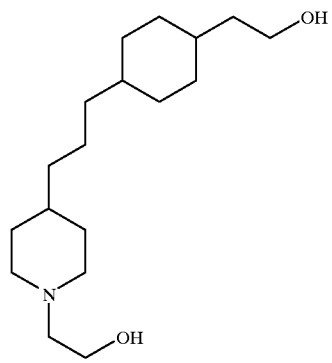
X-329
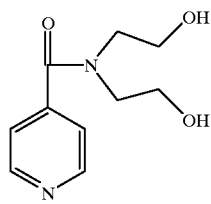
X-330
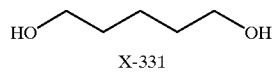
X-331
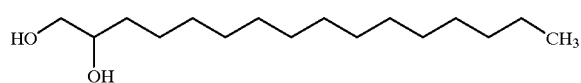
X-332
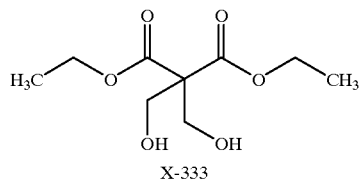
X-333
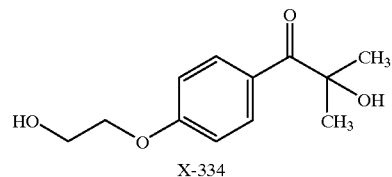
X-334
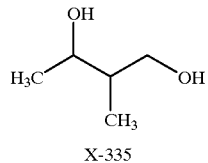
X-335

-continued
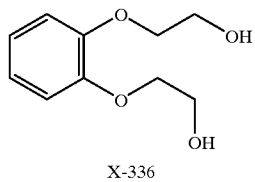
X-336
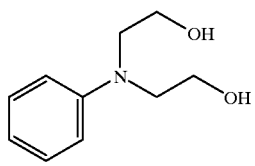
X-337
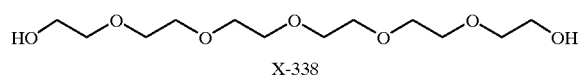
X-338
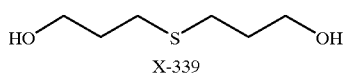
X-339
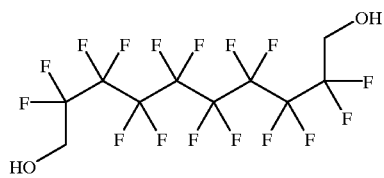
X-340
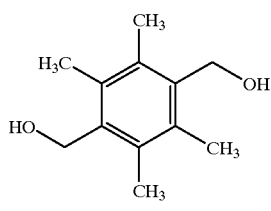
X-341
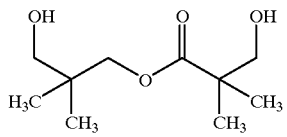
X-342
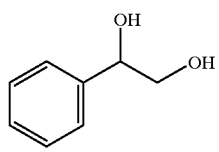
X-343
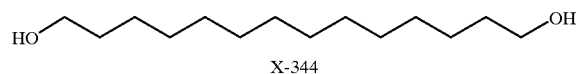
X-344
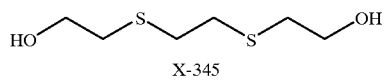
X-345

-continued
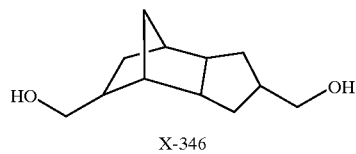
X-346
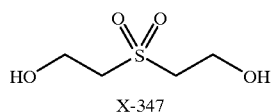
X-347
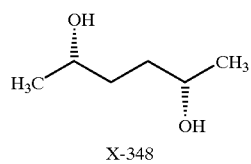
X-348
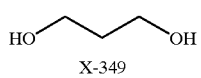
X-349
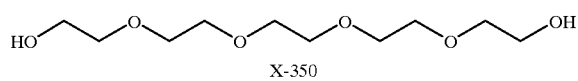
X-350
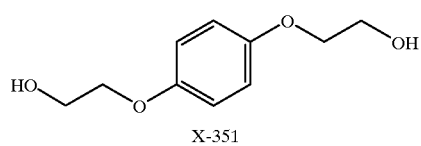
X-351
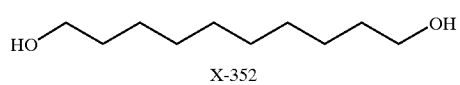
X-352
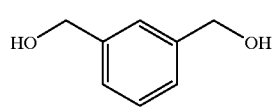
X-353
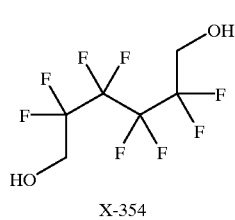
X-354
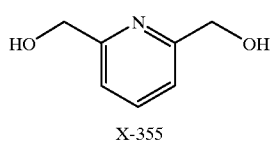
X-355

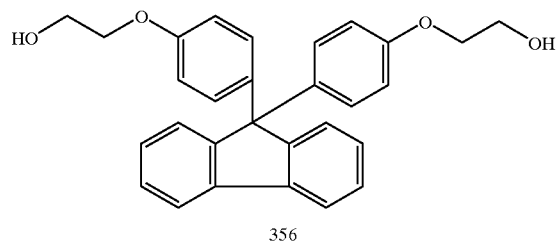
356
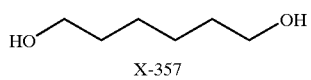
X-357
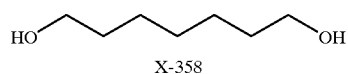
X-358
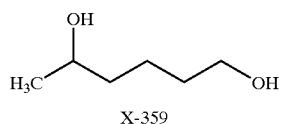
X-359
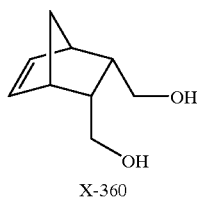
X-360
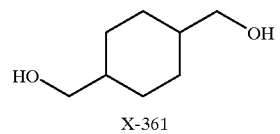
X-361
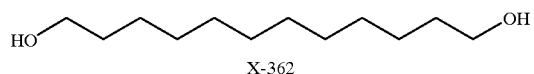
X-362
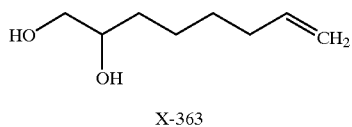
X-363
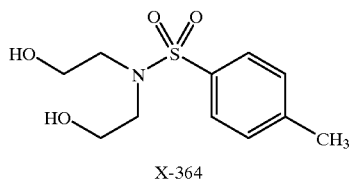
X-364
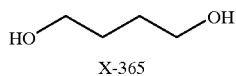
X-365

-continued
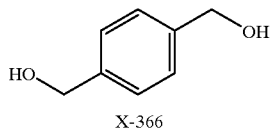
X-366
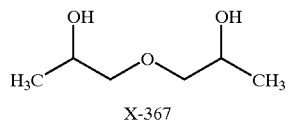
X-367
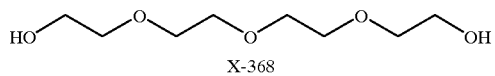
X-368
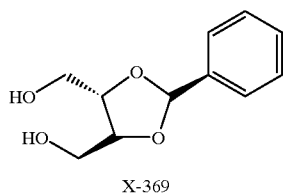
X-369
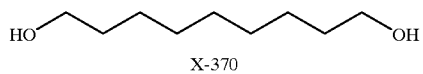
X-370
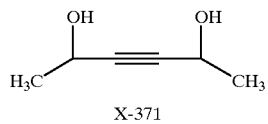
X-371
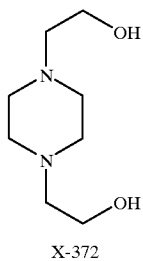
X-372
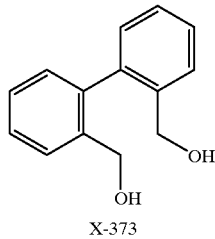
X-373

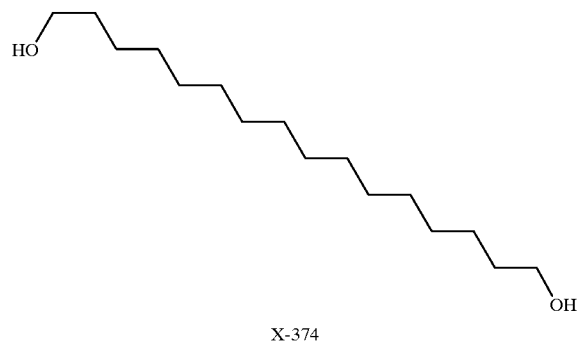
X-374
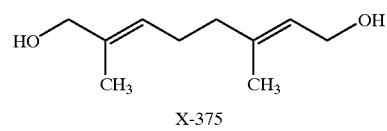
X-375
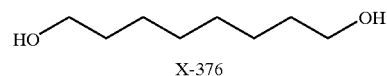
X-376
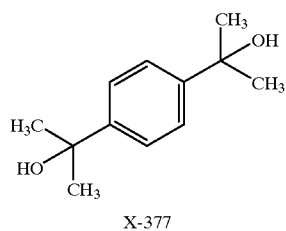
X-377
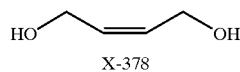
X-378
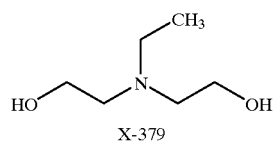
X-379
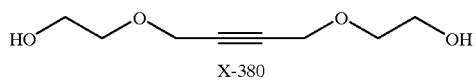
X-380
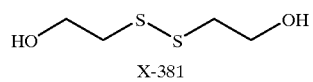
X-381
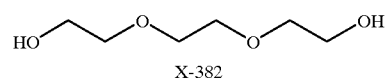
X-382
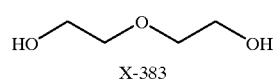
X-383
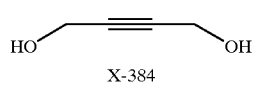
X-384

-continued
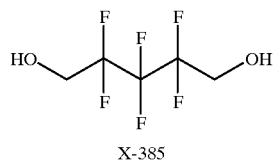
X-385
Dithiols
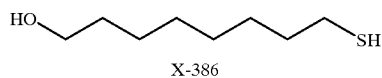
X-386
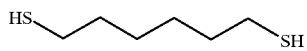
X-387
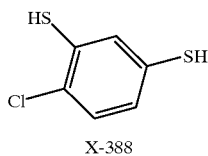
X-388
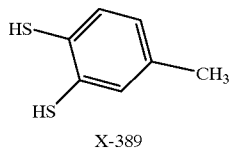
X-389
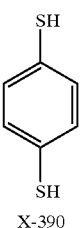
X-390
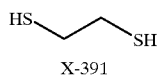
X-391
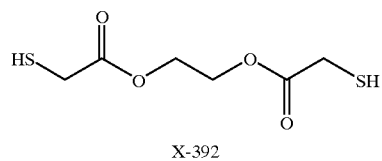
X-392
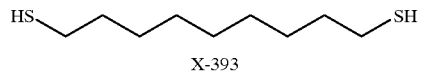
X-393
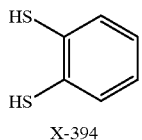
X-394

-continued
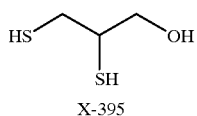
X-395
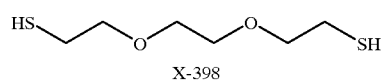
X-396
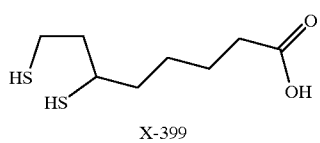
X-397
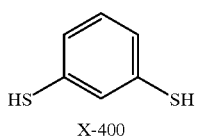
X-398
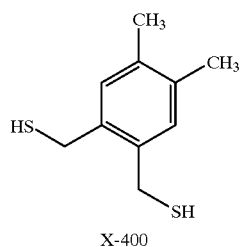
X-399
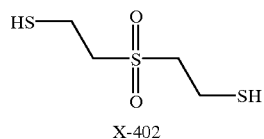
X-400
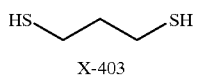
X-400
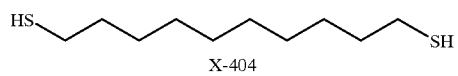
X-402
HS⏜⏜SH
X-403
HS⏜⏜⏜⏜⏜SH
X-404

-continued
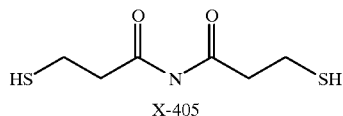
X-405
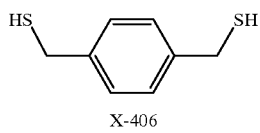
X-406
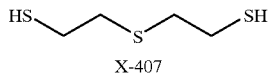
X-407
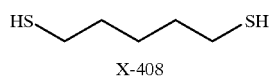
X-408
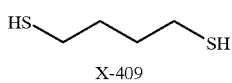
X-409
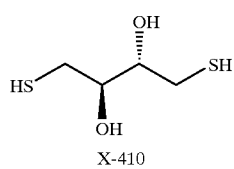
X-410
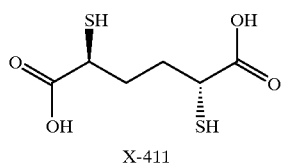
X-411
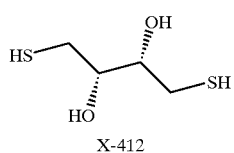
X-412
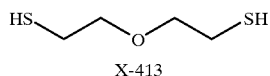
X-413
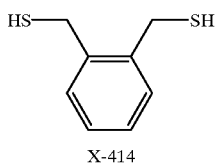
X-414
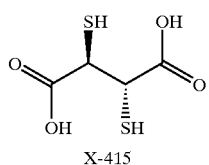
X-415

-continued

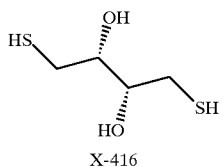

X-416

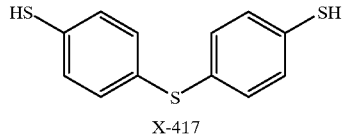

X-417

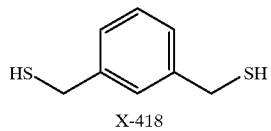

X-418

Representative ligands for use in this invention include, by way of example, ligands of formula IA–IE and IIA–IIE as defined herein.

Combinations of ligands (L) and linkers (X) per this invention include, by way example only, homo- and heterodimers wherein a first ligand is selected from formula IA through IE above and the second ligand and linker is selected from the following:

| | | | | | |
|---|---|---|---|---|---|
| IA/X-1- | IA/X-2- | IA/X-3- | IA/X-4- | IA/X-5- | IA/X-6- |
| IA/X-7- | IA/X-8- | IA/X-9- | IA/X-10- | IA/X-11- | IA/X-12- |
| IA/X-13- | IA/X-14- | IA/X-15- | IA/X-16- | 1A/X-17- | IA/X-18- |
| IA/X-19- | IA/X-20- | IA/X-21 - | IA/X-22- | IA/X-23- | IA/X-24- |
| IA/X-25- | IA/X-26- | IA/X-27- | IA/X-28- | IA/X-29- | IA/X-30- |
| IA/X-31- | IA/X-32- | IA/X-33- | IA/X-34- | IA/X-35- | IA/X-36- |
| IA/X-37- | IA/X-38- | IA/X-39- | IA/X-40- | IA/X-41- | IA/X-42- |
| IA/X-43- | IA/X-44- | IA/X-45- | IA/X-46- | IA/X-47- | IA/X-48- |
| IA/X-49- | IA/X-50- | IA/X-51- | IA/X-52- | IA/X-53- | IA/X-54- |
| IA/X-55- | IA/X-56- | IA/X-57- | IA/X-58- | IA/X-59- | IA/X-60- |
| IA/X-61- | IA/X-62- | IA/X-63- | IA/X-64- | IA/X-65- | IA/X-66- |
| IA/X-67- | IA/X-68- | IA/X-69- | IA/X-70- | IA/X-71- | IA/X-72- |
| IA/X-73- | IA/X-74- | IA/X-75- | IA/X-76- | IA/X-77- | IA/X-78- |
| IA/X-79- | IA/X-80- | IA/X-81- | IA/X-82- | IA/X-83- | IA/X-84- |
| IA/X-85- | IA/X-86- | IA/X-87- | IA/X-88- | IA/X-89- | IA/X-90- |
| IA/X-91- | IA/X-92- | IA/X-93- | IA/X-94- | IA/X-95- | IA/X-96- |
| IA/X-97- | IA/X-98- | IA/X-99- | IA/X-100- | IA/X-101- | IA/X-102- |
| IA/X-103- | IA/X-104- | IA/X-105- | IA/X-106- | IA/X-107- | IA/X-108- |
| IA/X-109- | IA/X-110- | IA/X-111- | IA/X-112- | IA/X-113- | IA/X-114- |
| IA/X-115- | IA/X-116- | IA/X-117- | IA/X-118- | IA/X-119- | IA/X-120- |
| IA/X-121- | IA/X-122- | IA/X-123- | IA/X-124- | IA/X-125- | IA/X-126- |
| IA/X-127- | IA/X-128- | IA/X-129- | IA/X-130- | IA/X-131- | IA/X-132- |
| IA/X-133- | IA/X-134- | IA/X-135- | IA/X-136- | IA/X-137- | IA/X-138- |
| IA/X-139- | IA/X-140- | IA/X-141- | IA/X-142- | IA/X-143- | IA/X-144- |
| IA/X-145- | IA/X-146- | IA/X-147- | IA/X-148- | IA/X-149- | IA/X-150- |
| IA/X-151- | IA/X-152- | IA/X-153- | IA/X-154- | IA/X-155- | IA/X-156- |
| IA/X-157- | IA/X-158- | IA/X-159- | IA/X-160- | IA/X-161- | IA/X-162- |
| IA/X-163- | IA/X-164- | IA/X-165- | IA/X-166- | IA/X-167- | IA/X-168- |
| IA/X-169- | IA/X-170- | IA/X-171- | IA/X-172- | | |
| IA/X-173- | IA/X-174- | IA/X-175- | IA/X-176- | IA/X-177- | IA/X-178- |
| IA/X-179- | IA/X-180- | IA/X-181- | IA/X-182- | IA/X-183- | IA/X-184- |
| IA/X-185- | IA/X-186- | IA/X-187- | IA/X-188- | IA/X-189- | IA/X-190- |
| IA/X-191- | IA/X-192- | IA/X-193- | IA/X-194- | IA/X-195- | IA/X-196- |
| IA/X-197- | IA/X-198- | IA/X-199- | IA/X-200- | IA/X-201- | IA/X-202- |
| IA/X-203- | IA/X-204- | IA/X-205- | IA/X-206- | IA/X-207- | IA/X-208- |
| IA/X-209- | IA/X-210- | IA/X-211- | IA/X-212- | IA/X-213- | IA/X-214- |
| IA/X-215- | IA/X-216- | IA/X-217- | IA/X-218- | IA/X-219- | IA/X-220- |
| IA/X-221- | IA/X-222- | IA/X-223- | IA/X-224- | IA/X-225- | IA/X-226- |
| IA/X-227- | IA/X-228- | IA/X-229- | IA/X-230- | IA/X-231- | IA/X-232- |

-continued

| | | | | | |
|---|---|---|---|---|---|
| IA/X-233- | IA/X-234- | IA/X-235- | IA/X-236- | IA/X-237- | IA/X-238- |
| IA/X-239- | IA/X-240- | IA/X-241- | IA/X-242- | IA/X-243- | IA/X-244- |
| IA/X-245- | IA/X-246- | IA/X-247- | IA/X-248- | IA/X-249- | IA/X-250- |
| IA/X-251- | IA/X-252- | IA/X-253- | IA/X-254- | IA/X-255- | IA/X-256- |
| IA/X-257- | IA/X-258- | IA/X-259- | IA/X-260- | IA/X-261- | IA/X-262- |
| IA/X-263- | IA/X-264- | IA/X-265- | IA/X-266- | IA/X-267- | IA/X-268- |
| IA/X-269- | IA/X-270- | IA/X-271- | IA/X-272- | IA/X-273- | IA/X-274- |
| IA/X-275- | IA/X-276- | IA/X-277- | IA/X-278- | IA/X-279- | IA/X-280- |
| IA/X-281- | IA/X-282- | IA/X-283- | IA/X-284- | IA/X-285- | IA/X-286- |
| IA/X-287- | IA/X-288- | IA/X-289- | IA/X-290- | IA/X-291- | IA/X-292- |
| IA/X-293- | IA/X-294- | IA/X-295- | IA/X-296- | IA/X-297- | IA/X-298- |
| IA/X-299- | IA/X-300- | IA/X-301- | IA/X-302- | IA/X-303- | IA/X-304- |
| IA/X-305- | IA/X-306- | IA/X-307- | IA/X-308- | IA/X-309- | IA/X-310- |
| IA/X-311- | IA/X-312- | IA/X-313- | IA/X-314- | IA/X-315- | IA/X-316- |
| IA/X-317- | IA/X-318- | IA/X-319- | IA/X-320- | IA/X-321- | IA/X-322- |
| IA/X-323- | IA/X-324- | IA/X-325- | IA/X-326- | IA/X-327- | IA/X-328- |
| IA/X-329- | IA/X-330- | IA/X-331- | IA/X-332- | IA/X-333- | IA/X-334- |
| IA/X-335- | IA/X-336- | IA/X-337- | IA/X-338- | IA/X-339- | IA/X-340- |
| IA/X-341- | IA/X-342- | IA/X-343- | IA/X-344- | IA/X-345- | IA/X-346- |
| IA/X-347- | IA/X-348- | IA/X-349- | IA/X-350- | IA/X-351- | IA/X-352- |
| IA/X-353- | IA/X-354- | IA/X-355- | IA/X-356- | IA/X-357- | IA/X-358- |
| IA/X-359- | IA/X-360- | IA/X-361- | IA/X-362- | IA/X-363- | IA/X-364- |
| IA/X-365- | IA/X-366- | IA/X-367- | IA/X-368- | IA/X-369- | IA/X-370- |
| IA/X-371- | IA/X-372- | IA/X-373- | IA/X-374- | IA/X-375- | IA/X-376- |
| IA/X-377- | IA/X-378- | IA/X-379- | IA/X-380- | IA/X-381- | IA/X-382- |
| IA/X-383- | IA/X-384- | IA/X-385- | IA/X-386- | IA/X-387- | IA/X-388- |
| IA/X-389- | IA/X-390- | IA/X-391- | IA/X-392- | IA/X-393- | IA/X-394- |
| IA/X-395- | IA/X-396- | IA/X-397- | IA/X-398- | IA/X-399- | IA/X-400- |
| IA/X-401- | IA/X-402- | IA/X-403- | IA/X-404- | IA/X-405- | IA/X-406- |
| IA/X-407- | IA/X-408- | IA/X-409- | IA/X-410- | IA/X-411- | IA/X-412- |
| IA/X-413- | IA/X-414- | IA/X-415- | IA/X-416- | IA/X-417- | IA/X-418- |
| IB/X-1- | IB/X-2- | IB/X-3- | IB/X-4- | IB/X-5- | IB/X-6- |
| IB/X-7- | IB/X-8- | IB/X-9- | IB/X-10- | IB/X-11- | IB/X-12- |
| IB/X-13- | IB/X-14- | IB/X-15- | IB/X-16- | IB/X-17- | IB/X-18- |
| IB/X-19- | IB/X-20- | IB/X-21- | IB/X-22- | IB/X-23- | IB/X-24- |
| IB/X-25- | IB/X-26- | IB/X-27- | IB/X-28- | IB/X-29- | IB/X-30- |
| IB/X-31- | IB/X-32- | IB/X-33- | IB/X-34- | IB/X-35- | IB/X-36- |
| IB/X-37- | IB/X-38- | IB/X-39- | IB/X-40- | IB/X-41- | IB/X-42- |
| IB/X-43- | IB/X-44- | IB/X-45- | IB/X-46- | IB/X-47- | IB/X-48- |
| IB/X-49- | IB/X-50- | IB/X-51- | IB/X-52- | IB/X-53- | IB/X-54- |
| IB/X-55- | IB/X-56- | IB/X-57- | IB/X-58- | IB/X-59- | IB/X-60- |
| IB/X-61- | IB/X-62- | IB/X-63- | IB/X-64- | IB/X-65- | IB/X-66- |
| IB/X-67- | IB/X-68- | IB/X-69- | IB/X-70- | IB/X-71- | IB/X-72- |
| IB/X-73- | IB/X-74- | IB/X-75- | IB/X-76- | IB/X-77- | IB/X-78- |
| IB/X-79- | IB/X-80- | IB/X-81- | IB/X-82- | IB/X-83- | IB/X-84- |
| IB/X-85- | IB/X-86- | IB/X-87- | IB/X-88- | IB/X-89- | IB/X-90- |
| IB/X-91- | IB/X-92- | IB/X-93- | IB/X-94- | IB/X-95- | IB/X-96- |
| IB/X-97- | IB/X-98- | IB/X-99- | IB/X-100- | IB/X-101- | IB/X-102- |
| IB/X-103- | IB/X-104- | IB/X-105- | IB/X-106- | IB/X-107- | IB/X-108- |

| | | | | | |
|---|---|---|---|---|---|
| IB/X-109- | IB/X-110- | IB/X-111- | IB/X-112- | IB/X-113- | IB/X-114- |
| IB/X-115- | IB/X-116- | IB/X-117- | IB/X-118- | IB/X-119- | IB/X-120- |
| IB/X-121- | IB/X-122- | IB/X-123- | IB/X-124- | IB/X-125- | IB/X-126- |
| IB/X-127- | IB/X-128- | IB/X-129- | IB/X-130- | IB/X-131- | IB/X-132- |
| IB/X-133- | IB/X-134- | IB/X-135- | IB/X-136- | IB/X-137- | IB/X-138- |
| IB/X-139- | IB/X-140- | IB/X-141- | IB/X-142- | IB/X-143- | IB/X-144- |
| IB/X-145- | IB/X-146- | IB/X-147- | IB/X-148- | IB/X-149- | IB/X-150- |
| IB/X-151- | IB/X-152- | IB/X-153- | IB/X-154- | IB/X-155- | IB/X-156- |
| IB/X-157- | IB/X-158- | IB/X-159- | IB/X-160- | IB/X-161- | IB/X-162- |
| IB/X-163- | IB/X-164- | IB/X-165- | IB/X-166- | IB/X-167- | IB/X-168- |
| IB/X-169- | IB/X-170- | IB/X-171- | IB/X-172- | | |
| IB/X-173- | IB/X-174- | IB/X-175- | IB/X-176- | IB/X-177- | IB/X-178- |
| IB/X-179- | IB/X-180- | IB/X-181- | IB/X-182- | IB/X-183- | IB/X-184- |
| IB/X-185- | IB/X-186- | IB/X-187- | IB/X-188- | IB/X-189- | IB/X-190- |
| IB/X-191- | IB/X-192- | IB/X-193- | IB/X-194- | IB/X-195- | IB/X-196- |
| IB/X-197- | IB/X-198- | IB/X-199- | IB/X-200- | IB/X-201- | IB/X-202- |
| IB/X-203- | IB/X-204- | IB/X-205- | IB/X-206- | IB/X-207- | IB/X-208- |
| IB/X-209- | IB/X-210- | IB/X-211- | IB/X-212- | IB/X-213- | IB/X-214- |
| IB/X-215- | IB/X-216- | IB/X-217- | IB/X-218- | IB/X-219- | IB/X-220- |
| IB/X-221- | IB/X-222- | IB/X-223- | IB/X-224- | IB/X-225- | IB/X-226- |
| IB/X-227- | IB/X-228- | IB/X-229- | IB/X-230- | IB/X-231- | IB/X-232- |
| IB/X-233- | IB/X-234- | IB/X-235- | IB/X-236- | IB/X-237- | IB/X-238- |
| IB/X-239- | IB/X-240- | IB/X-241- | IB/X-242- | IB/X-243- | IB/X-244- |
| IB/X-245- | IB/X-246- | IB/X-247- | IB/X-248- | IB/X-249- | IB/X-250- |
| IB/X-251- | IB/X-252- | IB/X-253- | IB/X-254- | IB/X-255- | IB/X-256- |
| IB/X-257- | IB/X-258- | IB/X-259- | IB/X-260- | IB/X-261- | IB/X-262- |
| IB/X-263- | IB/X-264- | IB/X-265- | IB/X-266- | IB/X-267- | IB/X-268- |
| IB/X-269- | IB/X-270- | IB/X-271- | IB/X-272- | IB/X-273- | IB/X-274- |
| IB/X-275- | IB/X-276- | IB/X-277- | IB/X-278- | IB/X-279- | IB/X-280- |
| IB/X-281- | IB/X-282- | IB/X-283- | IB/X-284- | IB/X-285- | IB/X-286- |
| IB/X-287- | IB/X-288- | IB/X-289- | IB/X-290- | IB/X-291- | IB/X-292- |
| IB/X-293- | IB/X-294- | IB/X-295- | IB/X-296- | IB/X-297- | IB/X-298- |
| IB/X-299- | IB/X-300- | IB/X-301- | IB/X-302- | IB/X-303- | IB/X-304- |
| IB/X-305- | IB/X-306- | IB/X-307- | IB/X-308- | IB/X-309- | IB/X-310- |
| IB/X-311- | IB/X-312- | IB/X-313- | IB/X-314- | IB/X-315- | IB/X-316- |
| IB/X-317- | IB/X-318- | IB/X-319- | IB/X-320- | IB/X-321- | IB/X-322- |
| IB/X-323- | IB/X-324- | IB/X-325- | IB/X-326- | IB/X-327- | IB/X-328- |
| IB/X-329- | IB/X-330- | IB/X-331- | IB/X-332- | IB/X-333- | IB/X-334- |
| IB/X-335- | IB/X-336- | IB/X-337- | IB/X-338- | IB/X-339- | IB/X-340- |
| IB/X-341- | IB/X-342- | IB/X-343- | IB/X-344- | IB/X-345- | IB/X-346- |
| IB/X-347- | IB/X-348- | IB/X-349- | IB/X-350- | IB/X-351- | IB/X-352- |
| IB/X-353- | IB/X-354- | IB/X-355- | IB/X-356- | IB/X-357- | IB/X-358- |
| IB/X-359- | IB/X-360- | IB/X-361- | IB/X-362- | IB/X-363- | IB/X-364- |
| IB/X-365- | IB/X-366- | IB/X-367- | IB/X-368- | IB/X-369- | IB/X-370- |
| IB/X-371- | IB/X-372- | IB/X-373- | IB/X-374- | IB/X-375- | IB/X-376- |
| IB/X-377- | IB/X-378- | IB/X-379- | IB/X-380- | IB/X-381- | IB/X-382- |
| IB/X-383- | IB/X-384- | IB/X-385- | IB/X-386- | IB/X-387- | IB/X-388- |
| IB/X-389- | IB/X-390- | IB/X-391- | IB/X-392- | IB/X-393- | IB/X-394- |
| IB/X-395- | IB/X-396- | IB/X-397- | IB/X-398- | IB/X-399- | IB/X-400- |
| IB/X-401- | IB/X-402- | IB/X-403- | IB/X-404- | IB/X-405- | IB/X-406- |
| IB/X-407- | IB/X-408- | IB/X-409- | IB/X-410- | IB/X-411- | IB/X-412- |
| IB/X-413- | IB/X-414- | IB/X-415- | IB/X-416- | IB/X-417- | IB/X-418- |
| IC/X-1- | IC/X-2- | IC/X-3- | IC/X-4- | IC/X-5- | IC/X-6- |
| IC/X-7- | IC/X-8- | IC/X-9- | IC/X-10- | IC/X-11- | IC/X-12- |
| IC/X-13- | IC/X-14- | IC/X-15- | IC/X-16- | IC/X-17- | IC/X-18- |
| IC/X-19- | IC/X-20- | IC/X-21- | IC/X-22- | IC/X-23- | IC/X-24- |
| IC/X-25- | IC/X-26- | IC/X-27- | IC/X-28- | IC/X-29- | IC/X-30- |
| IC/X-31- | IC/X-32- | IC/X-33- | IC/X-34- | IC/X-35- | IC/X-36- |
| IC/X-37- | IC/X-38- | IC/X-39- | IC/X-40- | IC/X-41- | IC/X-42- |
| IC/X-43- | IC/X-44- | IC/X-45- | IC/X-46- | IC/X-47- | IC/X-48- |
| IC/X-49- | IC/X-50- | IC/X-51- | IC/X-52- | IC/X-53- | IC/X-54- |
| IC/X-55- | IC/X-56- | IC/X-57- | IC/X-58- | IC/X-59- | IC/X-60- |
| IC/X-61- | IC/X-62- | IC/X-63- | IC/X-64- | IC/X-65- | IC/X-66- |
| IC/X-67- | IC/X-68- | IC/X-69- | IC/X-70- | IC/X-71- | IC/X-72- |
| IC/X-73- | IC/X-74- | IC/X-75- | IC/X-76- | IC/X-77- | IC/X-78- |
| IC/X-79- | IC/X-80- | IC/X-81- | IC/X-82- | IC/X-83- | IC/X-84- |
| IC/X-85- | IC/X-86- | IC/X-87- | IC/X-88- | IC/X-89- | IC/X-90- |
| IC/X-91- | IC/X-92- | IC/X-93- | IC/X-94- | IC/X-95- | IC/X-96- |
| IC/X-97- | IC/X-98- | IC/X-99- | IC/X-100- | IC/X-101- | IC/X-102- |
| IC/X-103- | IC/X-104- | IC/X-105- | IC/X-106- | IC/X-107- | IC/X-108- |
| IC/X-109- | IC/X-110- | IC/X-111- | IC/X-112- | IC/X-113- | IC/X-114- |
| IC/X-115- | IC/X-116- | IC/X-117- | IC/X-118- | IC/X-119- | IC/X-120- |
| IC/X-121- | IC/X-122- | IC/X-123- | IC/X-124- | IC/X-125- | IC/X-126- |
| IC/X-127- | IC/X-128- | IC/X-129- | IC/X-130- | IC/X-131- | IC/X-132- |
| IC/X-133- | IC/X-134- | IC/X-135- | IC/X-136- | IC/X-137- | IC/X-138- |
| IC/X-139- | IC/X-140- | IC/X-141- | IC/X-142- | IC/X-143- | IC/X-144- |
| IC/X-145- | IC/X-146- | IC/X-147- | IC/X-148- | IC/X-149- | IC/X-150- |
| IC/X-151- | IC/X-152- | IC/X-153- | IC/X-154- | IC/X-155- | IC/X-156- |
| IC/X-157- | IC/X-158- | IC/X-159- | IC/X-160- | IC/X-161- | IC/X-162- |
| IC/X-163- | IC/X-164- | IC/X-165- | IC/X-166- | IC/X-167- | IC/X-168- |
| IC/X-169- | IC/X-170- | IC/X-171- | IC/X-172- | | |
| IC/X-173- | IC/X-174- | IC/X-175- | IC/X-176- | IC/X-177- | IC/X-178- |
| IC/X-179- | IC/X-180- | IC/X-181- | IC/X-182- | IC/X-183- | IC/X-184- |
| IC/X-185- | IC/X-186- | IC/X-187- | IC/X-188- | IC/X-189- | IC/X-190- |
| IC/X-191- | IC/X-192- | IC/X-193- | IC/X-194- | IC/X-195- | IC/X-196- |
| IC/X-197- | IC/X-198- | IC/X-199- | IC/X-200- | IC/X-201- | IC/X-202- |
| IC/X-203- | IC/X-204- | IC/X-205- | IC/X-206- | IC/X-207- | IC/X-208- |
| IC/X-209- | IC/X-210- | IC/X-211- | IC/X-212- | IC/X-213- | IC/X-214- |
| IC/X-215- | IC/X-216- | IC/X-217- | IC/X-218- | IC/X-219- | IC/X-220- |
| IC/X-221- | IC/X-222- | IC/X-223- | IC/X-224- | IC/X-225- | IC/X-226- |
| IC/X-227- | IC/X-228- | IC/X-229- | IC/X-230- | IC/X-231- | IC/X-232- |
| IC/X-233- | IC/X-234- | IC/X-235- | IC/X-236- | IC/X-237- | IC/X-238- |
| IC/X-239- | IC/X-240- | IC/X-241- | IC/X-242- | IC/X-243- | IC/X-244- |
| IC/X-245- | IC/X-246- | IC/X-247- | IC/X-248- | IC/X-249- | IC/X-250- |
| IC/X-251- | IC/X-252- | IC/X-253- | IC/X-254- | IC/X-255- | IC/X-256- |
| IC/X-257- | IC/X-258- | IC/X-259- | IC/X-260- | IC/X-261- | IC/X-262- |
| IC/X-263- | IC/X-264- | IC/X-265- | IC/X-266- | IC/X-267- | IC/X-268- |
| IC/X-269- | IC/X-270- | IC/X-271- | IC/X-272- | IC/X-273- | IC/X-274- |
| IC/X-275- | IC/X-276- | IC/X-277- | IC/X-278- | IC/X-279- | IC/X-280- |
| IC/X-281- | IC/X-282- | IC/X-283- | IC/X-284- | IC/X-285- | IC/X-286- |
| IC/X-287- | IC/X-288- | IC/X-289- | IC/X-290- | IC/X-291- | IC/X-292- |
| IC/X-293- | IC/X-294- | IC/X-295- | IC/X-296- | IC/X-297- | IC/X-298- |
| IC/X-299- | IC/X-300- | IC/X-301- | IC/X-302- | IC/X-303- | IC/X-304- |
| IC/X-305- | IC/X-306- | IC/X-307- | IC/X-308- | IC/X-309- | IC/X-310- |
| IC/X-311- | IC/X-312- | IC/X-313- | IC/X-314- | IC/X-315- | IC/X-316- |
| IC/X-317- | IC/X-318- | IC/X-319- | IC/X-320- | IC/X-321- | IC/X-322- |
| IC/X-323- | IC/X-324- | IC/X-325- | IC/X-326- | IC/X-327- | IC/X-328- |
| IC/X-329- | IC/X-330- | IC/X-331- | IC/X-332- | IC/X-333- | IC/X-334- |
| IC/X-335- | IC/X-336- | IC/X-337- | IC/X-338- | IC/X-339- | IC/X-340- |
| IC/X-341- | IC/X-342- | IC/X-343- | IC/X-344- | IC/X-345- | IC/X-346- |
| IC/X-347- | IC/X-348- | IC/X-349- | IC/X-350- | IC/X-351- | IC/X-352- |
| IC/X-353- | IC/X-354- | IC/X-355- | IC/X-356- | IC/X-357- | IC/X-358- |
| IC/X-359- | IC/X-360- | IC/X-361- | IC/X-362- | IC/X-363- | IC/X-364- |
| IC/X-365- | IC/X-366- | IC/X-367- | IC/X-368- | IC/X-369- | IC/X-370- |
| IC/X-371- | IC/X-372- | IC/X-373- | IC/X-374- | IC/X-375- | IC/X-376- |
| IC/X-377- | IC/X-378- | IC/X-379- | IC/X-380- | IC/X-381- | IC/X-382- |
| IC/X-383- | IC/X-384- | IC/X-385- | IC/X-386- | IC/X-387- | IC/X-388- |
| IC/X-389- | IC/X-390- | IC/X-391- | IC/X-392- | IC/X-393- | IC/X-394- |
| IC/X-395- | IC/X-396- | IC/X-397- | IC/X-398- | IC/X-399- | IC/X-400- |
| IC/X-401- | IC/X-402- | IC/X-403- | IC/X-404- | IC/X-405- | IC/X-406- |
| IC/X-407- | IC/X-408- | IC/X-409- | IC/X-410- | IC/X-411- | IC/X-412- |
| IC/X-413- | IC/X-414- | IC/X-415- | IC/X-416- | IC/X-417- | IC/X-418- |
| ID/X-1- | ID/X-2- | ID/X-3- | ID/X-4- | ID/X-5- | ID/X-6- |
| ID/X-7- | ID/X-8- | ID/X-9- | ID/X-10- | ID/X-11- | ID/X-12- |
| ID/X-13- | ID/X-14- | ID/X-15- | ID/X-16- | ID/X-17- | ID/X-18- |
| ID/X-19- | ID/X-20- | ID/X-21- | ID/X-22- | ID/X-23- | ID/X-24- |
| ID/X-25- | ID/X-26- | ID/X-27- | ID/X-28- | ID/X-29- | ID/X-30- |
| ID/X-31- | ID/X-32- | ID/X-33- | ID/X-34- | ID/X-35- | ID/X-36- |
| ID/X-37- | ID/X-38- | ID/X-39- | ID/X-40- | ID/X-41- | ID/X-42- |
| ID/X-43- | ID/X-44- | ID/X-45- | ID/X-46- | ID/X-47- | ID/X-48- |
| ID/X-49- | ID/X-50- | ID/X-51- | ID/X-52- | ID/X-53- | ID/X-54- |
| ID/X-55- | ID/X-56- | ID/X-57- | ID/X-58- | ID/X-59- | ID/X-60- |
| ID/X-61- | ID/X-62- | ID/X-63- | ID/X-64- | ID/X-65- | ID/X-66- |
| ID/X-67- | ID/X-68- | ID/X-69- | ID/X-70- | ID/X-71- | ID/X-72- |
| ID/X-73- | ID/X-74- | ID/X-75- | ID/X-76- | ID/X-77- | ID/X-78- |
| ID/X-79- | ID/X-80- | ID/X-81- | ID/X-82- | ID/X-83- | ID/X-84- |
| ID/X-85- | ID/X-86- | ID/X-87- | ID/X-88- | ID/X-89- | ID/X-90- |
| ID/X-91- | ID/X-92- | ID/X-93- | ID/X-94- | ID/X-95- | ID/X-96- |
| ID/X-97- | ID/X-98- | ID/X-99- | ID/X-100- | ID/X-101- | ID/X-102- |
| ID/X-103- | ID/X-104- | ID/X-105- | ID/X-106- | ID/X-107- | ID/X-108- |
| ID/X-109- | ID/X-110- | ID/X-111- | ID/X-112- | ID/X-113- | ID/X-114- |
| ID/X-115- | ID/X-116- | ID/X-117- | ID/X-118- | ID/X-119- | ID/X-120- |
| ID/X-121- | ID/X-122- | ID/X-123- | ID/X-124- | ID/X-125- | ID/X-126- |
| ID/X-127- | ID/X-128- | ID/X-129- | ID/X-130- | ID/X-131- | ID/X-132- |
| ID/X-133- | ID/X-134- | ID/X-135- | ID/X-136- | ID/X-137- | ID/X-138- |
| ID/X-139- | ID/X-140- | ID/X-141- | ID/X-142- | ID/X-143- | ID/X-144- |
| ID/X-145- | ID/X-146- | ID/X-147- | ID/X-148- | ID/X-149- | ID/X-150- |
| ID/X-151- | ID/X-152- | ID/X-153- | ID/X-154- | ID/X-155- | ID/X-156- |
| ID/X-157- | ID/X-158- | ID/X-159- | ID/X-160- | ID/X-161- | ID/X-162- |
| ID/X-163- | ID/X-164- | ID/X-165- | ID/X-166- | ID/X-167- | ID/X-168- |
| ID/X-169- | ID/X-170- | ID/X-171- | ID/X-172- | | |
| ID/X-173- | ID/X-174- | ID/X-175- | ID/X-176- | ID/X-177- | ID/X-178- |
| ID/X-179- | ID/X-180- | ID/X-181- | ID/X-182- | ID/X-183- | ID/X-184- |
| ID/X-185- | ID/X-186- | ID/X-187- | ID/X-188- | ID/X-189- | ID/X-190- |
| ID/X-191- | ID/X-192- | ID/X-193- | ID/X-194- | ID/X-195- | ID/X-196- |
| ID/X-197- | ID/X-198- | ID/X-199- | ID/X-200- | ID/X-201- | ID/X-202- |
| ID/X-203- | ID/X-204- | ID/X-205- | ID/X-206- | ID/X-207- | ID/X-208- |
| ID/X-209- | ID/X-210- | ID/X-211- | ID/X-212- | ID/X-213- | ID/X-214- |

| | | | | | |
|---|---|---|---|---|---|
| ID/X-215- | ID/X-216- | ID/X-217- | ID/X-218- | ID/X-219- | ID/X-220- |
| ID/X-221- | ID/X-222- | ID/X-223- | ID/X-224- | ID/X-225- | ID/X-226- |
| ID/X-227- | ID/X-228- | ID/X-229- | ID/X-230- | ID/X-231- | ID/X-232- |
| ID/X-233- | ID/X-234- | ID/X-235- | ID/X-236- | ID/X-237- | ID/X-238- |
| ID/X-239- | ID/X-240- | ID/X-241- | ID/X-242- | ID/X-243- | ID/X-244- |
| ID/X-245- | ID/X-246- | ID/X-247- | ID/X-248- | ID/X-249- | ID/X-250- |
| ID/X-251- | ID/X-252- | ID/X-253- | ID/X-254- | ID/X-255- | ID/X-256- |
| ID/X-257- | ID/X-258- | ID/X-259- | ID/X-260- | ID/X-261- | ID/X-262- |
| ID/X-263- | ID/X-264- | ID/X-265- | ID/X-266- | ID/X-267- | ID/X-268- |
| ID/X-269- | ID/X-270- | ID/X-271- | ID/X-272- | ID/X-273- | ID/X-274- |
| ID/X-275- | ID/X-276- | ID/X-277- | ID/X-278- | ID/X-279- | ID/X-280- |
| ID/X-281- | ID/X-282- | ID/X-283- | ID/X-284- | ID/X-285- | ID/X-286- |
| ID/X-287- | ID/X-288- | ID/X-289- | ID/X-290- | ID/X-291- | ID/X-292- |
| ID/X-293- | ID/X-294- | ID/X-295- | ID/X-296- | ID/X-297- | ID/X-298- |
| ID/X-299- | ID/X-300- | ID/X-301- | ID/X-302- | ID/X-303- | ID/X-304- |
| ID/X-305- | ID/X-306- | ID/X-307- | ID/X-308- | ID/X-309- | ID/X-310- |
| ID/X-311- | ID/X-312- | ID/X-313- | ID/X-314- | ID/X-315- | ID/X-316- |
| ID/X-317- | ID/X-318- | ID/X-319- | ID/X-320- | ID/X-321- | ID/X-322- |
| ID/X-323- | ID/X-324- | ID/X-325- | ID/X-326- | ID/X-327- | ID/X-328- |
| ID/X-329- | ID/X-330- | ID/X-331- | ID/X-332- | ID/X-333- | ID/X-334- |
| ID/X-335- | ID/X-336- | ID/X-337- | ID/X-338- | ID/X-339- | ID/X-340- |
| ID/X-341- | ID/X-342- | ID/X-343- | ID/X-344- | ID/X-345- | ID/X-346- |
| ID/X-347- | ID/X-348- | ID/X-349- | ID/X-350- | ID/X-351- | ID/X-352- |
| ID/X-353- | ID/X-354- | ID/X-355- | ID/X-356- | ID/X-357- | ID/X-358- |
| ID/X-359- | ID/X-360- | ID/X-361- | ID/X-362- | ID/X-363- | ID/X-364- |
| ID/X-365- | ID/X-366- | ID/X-367- | ID/X-368- | ID/X-369- | ID/X-370- |
| ID/X-371- | ID/X-372- | ID/X-373- | ID/X-374- | ID/X-375- | ID/X-376- |
| ID/X-377- | ID/X-378- | ID/X-379- | ID/X-380- | ID/X-381- | ID/X-382- |
| ID/X-383- | ID/X-384- | ID/X-385- | ID/X-386- | ID/X-387- | ID/X-388- |
| ID/X-389- | ID/X-390- | ID/X-391- | ID/X-392- | ID/X-393- | ID/X-394- |
| ID/X-395- | ID/X-396- | ID/X-397- | ID/X-398- | ID/X-399- | ID/X-400- |
| ID/X-401- | ID/X-402- | ID/X-403- | ID/X-404- | ID/X-405- | ID/X-406- |
| ID/X-407- | ID/X-408- | ID/X-409- | ID/X-410- | ID/X-411- | ID/X-412- |
| ID/X-413- | ID/X-414- | ID/X-415- | ID/X-416- | ID/X-417- | ID/X-418- |
| IE/X-1- | IE/X-2- | IE/X-3- | IE/X-4- | IE/X-5- | IE/X-6- |
| IE/X-7- | IE/X-8- | IE/X-9- | IE/X-10- | IE/X-11- | IE/X-12- |
| IE/X-13- | IE/X-14- | IE/X-15- | IE/X-16- | IE/X-17- | IE/X-18- |
| IE/X-19- | IE/X-20- | IE/X-21- | IE/X-22- | IE/X-23- | IE/X-24- |
| IE/X-25- | IE/X-26- | IE/X-27- | IE/X-28- | IE/X-29- | IE/X-30- |
| IE/X-31- | IE/X-32- | IE/X-33- | IE/X-34- | IE/X-35- | 1E/X-36- |
| IE/X-37- | IE/X-38- | IE/X-39- | IE/X-40- | IE/X-41- | IE/X-42- |
| IE/X-43- | IE/X-44- | IE/X-45- | IE/X-46- | IE/X-47- | IE/X-48- |
| IE/X-49- | IE/X-50- | IE/X-51- | IE/X-52- | IE/X-53- | IE/X-54- |
| IE/X-55- | IE/X-56- | IE/X-57- | IE/X-58- | IE/X-59- | IE/X-60- |
| IE/X-61- | IE/X-62- | IE/X-63- | IE/X-64- | IE/X-65- | IE/X-66- |
| IE/X-67- | IE/X-68- | IE/X-69- | IE/X-70- | IE/X-71- | IE/X-72- |
| IE/X-73- | IE/X-74- | IE/X-75- | IE/X-76- | IE/X-77- | IE/X-78- |
| IE/X-79- | IE/X-80- | IE/X-81- | IE/X-82- | IE/X-83- | IE/X-84- |
| IE/X-85- | IE/X-86- | IE/X-87- | IE/X-88- | IE/X-89- | IE/X-90- |
| IE/X-91- | IE/X-92- | IE/X-93- | IE/X-94- | IE/X-95- | IE/X-96- |
| IE/X-97- | IE/X-98- | IE/X-99- | IE/X-100- | IE/X-101- | IE/X-102- |
| IE/X-103- | IE/X-104- | IE/X-105- | IE/X-106- | IE/X-107- | IE/X-108- |
| IE/X-109- | IE/X-110- | IE/X-111- | IE/X-112- | IE/X-113- | IE/X-114- |
| IE/X-115- | IE/X-116- | IE/X-117- | IE/X-118- | IE/X-119- | IE/X-120- |
| IE/X-121- | IE/X-122- | IE/X-123- | IE/X-124- | IE/X-125- | IE/X-126- |
| IE/X-127- | IE/X-128- | IE/X-129- | IE/X-130- | IE/X-131- | IE/X-132- |
| IE/X-133- | IE/X-134- | IE/X-135- | IE/X-136- | IE/X-137- | IE/X-138- |
| IE/X-139- | IE/X-140- | IE/X-141- | IE/X-142- | IE/X-143- | IE/X-144- |
| IE/X-145- | IE/X-146- | IE/X-147- | IE/X-148- | IE/X-149- | IE/X-150- |
| IE/X-151- | IE/X-152- | IE/X-153- | IE/X-154- | IE/X-155- | IE/X-156- |
| IE/X-157- | IE/X-158- | IE/X-159- | IE/X-160- | IE/X-161- | IE/X-162- |
| IE/X-163- | IE/X-164- | IE/X-165- | IE/X-166- | IE/X-167- | IE/X-168- |
| IE/X-169- | IE/X-170- | IE/X-171- | IE/X-172- | | |
| IE/X-173- | IE/X-174- | IE/X-175- | IE/X-176- | IE/X-177- | IE/X-178- |
| IE/X-179- | IE/X-180- | IE/X-181- | IE/X-182- | IE/X-183- | IE/X-184- |
| IE/X-185- | IE/X-186- | IE/X-187- | IE/X-188- | IE/X-189- | IE/X-190- |
| IE/X-191- | IE/X-192- | IE/X-193- | IE/X-194- | IE/X-195- | IE/X-196- |
| IE/X-197- | IE/X-198- | IE/X-199- | IE/X-200- | IE/X-201- | IE/X-202- |
| IE/X-203- | IE/X-204- | IE/X-205- | IE/X-206- | IE/X-207- | IE/X-208- |
| IE/X-209- | IE/X-210- | IE/X-211- | IE/X-212- | IE/X-213- | IE/X-214- |
| IE/X-215- | IE/X-216- | IE/X-217- | IE/X-218- | IE/X-219- | IE/X-220- |
| IE/X-221- | IE/X-222- | IE/X-223- | IE/X-224- | IE/X-225- | IE/X-226- |
| IE/X-227- | IE/X-228- | IE/X-229- | IE/X-230- | IE/X-231- | IE/X-232- |
| IE/X-233- | IE/X-234- | IE/X-235- | IE/X-236- | IE/X-237- | IE/X-238- |
| IE/X-239- | IE/X-240- | IE/X-241- | IE/X-242- | IE/X-243- | IE/X-244- |
| IE/X-245- | IE/X-246- | IE/X-247- | IE/X-248- | IE/X-249- | IE/X-250- |
| IE/X-251- | IE/X-252- | IE/X-253- | IE/X-254- | IE/X-255- | IE/X-256- |
| IE/X-257- | IE/X-258- | IE/X-259- | IE/X-260- | IE/X-261- | IE/X-262- |
| IE/X-263- | IE/X-264- | IE/X-265- | IE/X-266- | IE/X-267- | IE/X-268- |
| IE/X-269- | IE/X-270- | IE/X-271- | IE/X-272- | IE/X-273- | IE/X-274- |
| IE/X-275- | IE/X-276- | IE/X-277- | IE/X-278- | IE/X-279- | IE/X-280- |
| IE/X-281- | IE/X-282- | IE/X-283- | IE/X-284- | IE/X-285- | IE/X-286- |
| IE/X-287- | IE/X-288- | IE/X-289- | IE/X-290- | IE/X-291- | IE/X-292- |
| IE/X-293- | IE/X-294- | IE/X-295- | IE/X-296- | IE/X-297- | IE/X-298- |
| IE/X-299- | IE/X-300- | IE/X-301- | IE/X-302- | IE/X-303- | IE/X-304- |
| IE/X-305- | IE/X-306- | IE/X-307- | IE/X-308- | IE/X-309- | IE/X-310- |
| IE/X-311- | IE/X-312- | IE/X-313- | IE/X-314- | IE/X-315- | IE/X-316- |
| IE/X-317- | IE/X-318- | IE/X-319- | IE/X-320- | IE/X-321- | IE/X-322- |
| IE/X-323- | IE/X-324- | IE/X-325- | IE/X-326- | IE/X-327- | IE/X-328- |
| IE/X-329- | IE/X-330- | IE/X-331- | IE/X-332- | IE/X-333- | IE/X-334- |
| IE/X-335- | IE/X-336- | IE/X-337- | IE/X-338- | IE/X-339- | IE/X-340- |
| IE/X-341- | IE/X-342- | IE/X-343- | IE/X-344- | IE/X-345- | IE/X-346- |
| IE/X-347- | IE/X-348- | IE/X-349- | IE/X-350- | IE/X-351- | IE/X-352- |
| IE/X-353- | IE/X-354- | IE/X-355- | IE/X-356- | IE/X-357- | IE/X-358- |
| IE/X-359- | IE/X-360- | IE/X-361- | IE/X-362- | IE/X-363- | IE/X-364- |
| IE/X-365- | IE/X-366- | IE/X-367- | IE/X-368- | IE/X-369- | IE/X-370- |
| IE/X-371- | IE/X-372- | IE/X-373- | IE/X-374- | IE/X-375- | IE/X-376- |
| IE/X-377- | IE/X-378- | IE/X-379- | IE/X-380- | IE/X-381- | IE/X-382- |
| IE/X-383- | IE/X-384- | IE/X-385- | IE/X-386- | IE/X-387- | IE/X-388- |
| IE/X-389- | IE/X-390- | IE/X-391- | IE/X-392- | IE/X-393- | IE/X-394- |
| IE/X-395- | IE/X-396- | IE/X-397- | IE/X-398- | IE/X-399- | IE/X-400- |
| IE/X-401- | IE/X-402- | IE/X-403- | IE/X-404- | IE/X-405- | IE/X-406- |
| IE/X-407- | IE/X-408- | IE/X-409- | IE/X-410- | IE/X-411- | IE/X-412- |
| IE/X-413- | IE/X-414- | IE/X-415- | IE/X-416- | IE/X-417- | IE/X-418- | provided that when the first ligand has formula IA or IB, where $R^1$ or $R^2$ is a covalent bond linking the first ligand to the linker, then a second ligand does not have formula ID or IE, where $R^8$ or $R^9$ are a covalent bond linking the second ligand to the linker.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, Mace Publishing Company, Philadelphia, Pa., 17th ed. (1985).

Utility

The multibinding compounds of this invention inhibit microsomal triglyceride transferase protein (MTP), a protein which mediates the transfer of lipids during the assembly of lipoproteins and related biomolecules. Accordingly, the multibinding compounds and pharmaceutical compositions of this invention are useful for lowering serum lipid, cholesterol and/or triglyceride levels, and for preventing and treating disorders associated with atherosclerosis, hyperlipemia, hyperlipidemia, hyperlipoproteinemia, hypercholestrolemia, hypertriglyceridemia, pancreatitis, diabetes and/or obesity and the like.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like. In therapeutic applications, compositions are administered to a patient already suffering from, for example, hypertriglyceridemia or hypercholestrolemia in an amount sufficient to at least partially reduce the patient's triglyceride or cholesterol levels. Amounts effective for this use will depend on the judgment of the attending clinician depending upon factors such as the degree or severity of the disorder in the patient, the age, weight and general condition of the patient, and the like. The pharmaceutical compositions of this invention may contain more than one compound of the present invention.

As noted above, the compounds administered to a patient are in the form of pharmaceutical compositions described above which can be administered by a variety of routes including oral, rectal, transdermal, subcutaneous, intravenous, intramuscular, etc. These compounds are effective as both injectable and oral deliverable pharmaceutical compositions. Such compositions are prepared in a manner well known in the pharmaceutical art and comprise at least one active compound.

The multibinding compounds of this invention can also be administered in the form of pro-drugs, i.e., as derivatives which are converted into a biologically active compound in vivo. Such pro-drugs will typically include compounds in which, for example, a carboxylic acid group, a hydroxyl group or a thiol group is converted to a biologically liable group, such as an ester, lactone or thioester group which will hydrolyze in vivo to reinstate the respective group.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Å | = Angstroms |
| cm | = centimeter |
| DCC | = dicyclohexylcarbodiimide |
| DMF | = N,N-dimethylformamide |
| DMSO | = dimethylsulfoxide |
| EDTA | = ethylenediaminetetraacetic acid |
| g | = gram |
| HPLC | = high performance liquid chromatography |
| MEM | = minimal essential medium |
| mg | = milligram |
| MIC | = minimum inhibitory concentration |
| min | = minute |
| mL | = milliliter |
| mm | = millimeter |
| mmol | = millimol |
| N | = normal |
| THF | = tetrahydrofuran |
| μL | = microliters |
| μm | = microns |

Example A

Preparation of Synthon A

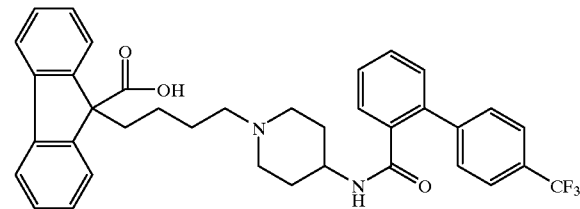

Synthon A is prepared by alkylation of Synthon F with [1-bromobutyl]-9H-fluorene-9-carboxylic acid, the preparation of which is described as part of Example 11 in U.S. Pat. No. 5,712,279. A solution of Synthon F hydrochloride (18.0 g, 49 mmol) in 100 mL dimethylformamide is stirred under argon at room temperature and treated with potassium carbonate (12.6 g, 49 mmol) followed by [1-bromobutyl]-9H-fluorene-9-carboxylic acid (16.9 g, 49 mmol). The reaction is heated to 50° C. for 24 h. After cooling, the reaction is filtered to remove potassium carbonate, and the filter cake is rinsed with ethyl acetate. The solvents are removed in vacuo to afford a solid from which Synthon A is obtained as an off-white solid after recrystallization from ethanol (24.1 g, 38.7 mmol, 79%).

Example B

Preparation of Synthon B

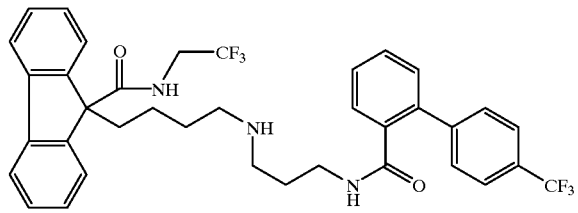

Synthon B is prepared from [1-bromobutyl]-N-(2,2,2-trifluoroethyl)-9H-fluorene-9-carboxamide (Example 11 in U.S. Pat. No. 5,712,279), 1,3-diaminopropane, and commercially available Synthon G.

The acid chloride derivative of Synthon G is generated as described in Example 10 of U.S. Pat. No. 5,712,279. To a slurry of Synthon G (50.0 g, 190 mmol) in 500 mL methylene chloride is added oxalyl chloride (28.7 mL, 330 mmol) followed by five drops of dimethylformamide. The reaction bubbles vigorously and is stirred at room temperature under argon for 2 h. At this time all solid has dissolved and gas evolution has ceased. The solvent is removed in vacuo, and the residue is dissolved in 400 mL methylene chloride. This solution is then added dropwise to a solution of 1,3-diaminopropane (31.7 mL, 380 mmol) and triethylamine (65.4 mL, 470 mmol) in 300 mL methylene chloride cooled in an ice/brine bath. After the addition is complete, a lot of solid has precipitated from the reaction. Additional methylene chloride (200 mL) is added and the reaction is stirred at room temperature under argon for 18 h. The reaction is then diluted with 600 mL methylene chloride and washed twice with saturated sodium bicarbonate solution, once with brine, and once with 1N potassium hydroxide. The organic layer is dried over sodium sulfate, and the solvent is removed in vacuo to give a white solid. This solid is recrystallized from hot ethanol and washed with heptane to afford 3"-(aminopropyl) 4'-(trifluoromethyl)-2-biphenylcarboxamide (45.8 g, 142 mmol, 75%) as a white solid.

To a stirred solution of [1-bromobutyl]-N-(2,2,2-trifluoroethyl)-9H-fluorene-9-carboxamide (29.5 g, 69.2 mmol) in 100 mL dimethylformamide under argon is added anhydrous potassium carbonate (9.55 g, 69.2 mmol) followed by 3"-(aminopropyl)-4'-(trifluoromethyl)-2-biphenylcarboxamide (22.3 g, 69.2 mmol). The reaction mixture is then heated to 50° C. and stirred under argon for 24 h. After cooling, the reaction is filterred to remove potassium carbonate, and the filter cake is rinsed with ethyl acetate. The filtrate is partitioned between 20% heptane in ethyl acetate and water. The organic layer is washed five times with water and once with brine. The organic layer is then dried over sodium sulfate and the solvent is removed in vacuo to give a beige solid. This solid is recrystallized from 300 mL 25% ethyl acetate in heptane to provide Synthon B as an off-white solid (36.5 g, 54.7 mmol, 79%).

Example C

Preparation of Synthon C

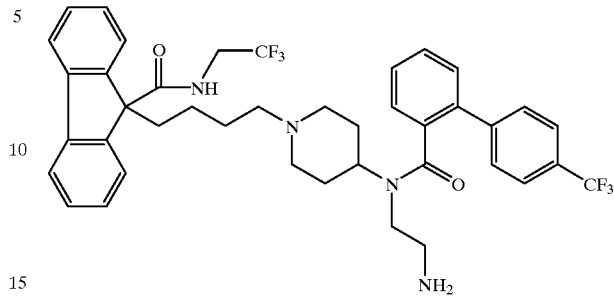

Synthon C is prepared from [1-bromobutyl]-N-(2,2,2-trifluoroethyl)-9H-fluorene-9-carboxamide (Example 11 in U.S. Pat. No. 5,712,279), tert-butyl N-(2-aminoethyl) carbamate, 1-benzyl-4-piperidone, and commercially available Synthon G.

Potassium hydroxide pellets (16 g, 0.25 mole) are added to a stirred solution of tert-butyl N-(2-aminoethyl)carbamate (160 g, 1.00 mole) in 1 L of methanol. Once the pellets are completely dissolved, 1-benzyl-4-piperidone (185 mL, 1.00 mole) is added in one portion and the resulting suspension is stirred under reflux for 1 h. The reaction is then cooled in an ice bath and treated dropwise with sodium cyanoborohydride (22.0 g, 0.35 mole) in 250 mL methanol. This mixture is allowed to warm to room temperature and is then refluxed for 1 h. After cooling to room temperature, the mixture is treated with potassium hydroxide pellets (60 g, 1.5 mole) and stirred until the pellets are completely dissolved. The reaction mixture is suction filtered and then concentrated to 250 mL on a rotary evaporator. The residue is then diluted with 500 mL half-saturated brine and extracted with two 500 mL portions of diethyl ether. The combined organic layers are in turn extracted with two 500 mL portions of 2 N sodium hydrogen sulfate and then discarded. The combined aqueous extracts are adjusted to pH 10 by the addition of 6 M sodium hydroxide and then back-extracted with two 500 mL portions of ethyl acetate. The combined ethyl acetate extracts are extracted with 500 mL brine, dried over sodium sulfate, and dried to afford the crude 1-benzyl-4-[(2-aminoethylcarbamato)amino]-piperidine as an oil.

The acid chloride derivative of Synthon G is generated as described in Example 10 of U.S. Pat. No. 5,712,279. To a slurry of Synthon G (50.0 g, 190 mmol) in 500 mL methylene chloride is added oxalyl chloride (28.7 mL, 330 mmol) followed by five drops of dimethylformamide. The reaction bubbles vigorously and is stirred at room temperature under argon for 2 h. At this time all solid has dissolved and gas evolution has ceased. The solvent is removed in vacuo, and the residue is dissolved in 400 mL methylene chloride. This solution is then added dropwise to a solution of the crude 1-benzyl-4-[(2-aminoethylcarbamato)amino]-piperidine (63.3 g, 190 mmol) prepared in the previous step and triethylamine (65.4 mL, 470 mmol) in 300 mL methylene chloride cooled in an ice/brine bath. After the addition is complete, a lot of solid has precipitated from the reaction. Additional methylene chloride (200 mL) is added and the reaction is stirred at room temperature under argon for 18 h. The reaction is then diluted with 600 mL methylene chloride and washed twice with saturated sodium bicarbonate solution, once with brine, and once with 1N potassium hydroxide. The organic layer is dried over sodium sulfate, and the solvent is removed in vacuo to give a white solid. This solid is recrystallized from hot ethanol and washed with heptane to afford 1-benzyl4-[[4'-(trifluoromethyl)[1,1'-biphenyl]-2-yl]carbonyl](2-aminoethylcarbamato)amino]-piperidine (74.8 g, 142 mmol, 75%) as a white solid.

A solution of 1-benzyl-4-[[4'-(trifluoromethyl)[1,1'-biphenyl]-2-yl]carbonyl](2-aminoethylcarbamato)amino]-piperidine (52.5 g, 100 mmol) in a mixture of 200 mL ethanol plus 10 mL glacial acetic acid is treated with 10% palladium on activated carbon (2.6 g) and then subjected to hydrogenation on a Parr apparatus (initial pressure 40 psi) for 19 h. The reaction is then filtered through Celite and the filtrate is concentrated to dryness. The residue is dissolved in 500 mL chloroform and washed once with 100 mL 1 N potassium hydroxide and three times with 100 mL brine. The aqueous layers are combined and back-exctracted with three 80 mL portions of chloroform. The combined organic extracts are then dried over sodium sulfate and evaporated to afford 4-[[4'-(trifluoromethyl)[1,1'-biphenyl]-2-yl]carbonyl](2-aminoethylcarbamato)amino]-1-piperidine (39.2 g, 90 mmol, 90%) as a white solid.

To a stirred solution of [1-bromobutyl]-N-(2,2,2-trifluoroethyl)-9H-fluorene-9-carboxamide (29.5 g, 69.2 mmol) in 100 mL dimethylformamide under argon is added anhydrous potassium carbonate (9.55 g, 69.2 mmol) followed by 4-[[4'-(trifluoromethyl)[1,1'-biphenyl]-2-yl]carbonyl](2-aminoethylcarbamato)amino]-1-piperidine prepared in the previous step (30.1 g, 69.2 mmol). The reaction mixture is then heated to 50° C. and stirred under argon for 24 h. After cooling, the reaction is filterred to remove potassium carbonate, and the filter cake is rinsed with ethyl acetate. The filtrate is partitioned between 20% heptane in ethyl acetate and water. The organic layer is washed five times with water and once with brine. The organic layer is then dried over sodium sulfate and the solvent is removed in vacuo to give a beige solid. This solid is recrystallized from 300 mL 25% ethyl acetate in heptane to provide 9-[4-[4-[[[4'-(trifluoromethyl)[1,1'-biphenyl]-2-yl]carbonyl](2-aminoethylcarbamato)amino]-1-piperidinyl]butyl]-N-(2,2,2-trifluoroethyl)-9H-fluorene-9-carboxamide, the Boc-protected form of Synthon C (40.5 g, 52 mmol, 75%) as a white solid.

To a solution of 9-[4-[4-[[[4'-(trifluoromethyl)[1,1'-biphenyl]-2-yl]carbonyl](2-aminoethylcarbamato)amino]-1-piperidinyl]butyl]-N-(2,2,2-trifluoroethyl)-9H-fluorene-9-carboxamide (30.0 g, 38.5 mmol) in 100 mL dioxane was added 75 mL 4 N HCl in dioxane (300 mmol). The reaction was stirred at room temperature for 4 h, then concentrated in vacuo to afford 9-[4-[4-[[[4'-(trifluoromethyl)[1,1'-biphenyl]-2-yl]carbonyl]amino]-1-piperidinyl]butyl]-N-(2,2,2-trifluoroethyl)-9H-fluorene-9-carboxamide (27.8 g, 37 mmol, 96%)) as the white solid dihydrochloride.

Example D

Preparation of Synthon D

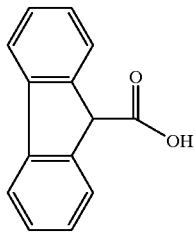

Synthon D is commercially available, for example, from Aldrich Chemical Company, Milwaukee, Wis. 53201 USA.

Example E

Preparation of Synthon E

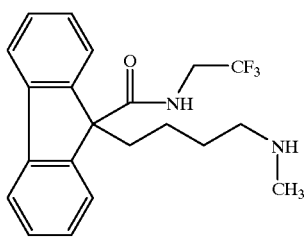

Synthon E is prepared from [1-bromobutyl]-N-(2,2,2-trifluoroethyl)-9H-fluorene-9-carboxamide (Example 11 in U.S. Pat. No. 5,712,279) and methylamine. [1-bromobutyl]-N-(2,2,2-trifluoroethyl)-9H-fluorene-9-carboxamide (29.5 g, 69.2 mmol), methylamine hydrochloride (5.06 g, 75.0 mmol), and anhydrous potassium carbonate (23.0 g, 166 mmol) are placed in a glass pressure vessel. Dimethylformamide (100 mL) is added, and the vessel is then sealed and heated at 50° C. for 48 h, cooled and concentrated to dryness, and taken up in 500 mL methylene chloride. The solution is washed with three 80 mL portions of saturated sodium bicarbonate solution and then two 80 mL portions of brine, followed by drying over magnesium sulfate and evaporation of solvent. The crude is fractionated by flash chromatography on 600 g silica gel, loading the mixture in methylene chloride and then eluting with a step gradient of 2% to 3% methanol in methylene chloride (4 L total solvent volume). Fractions containing pure compound are combined and evaporated to yield Synthon E (22.5 g, 59.5 mmol, 86%) as a white foamy gum.

Example F

Preparation of Synthon F

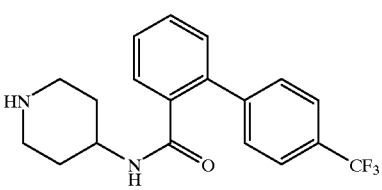

The preparation of Synthon F as the dihydrochloride salt is described as part of Example 10 in U.S. Pat. No. 5,712,279.

Example G

Preparation of Synthon G

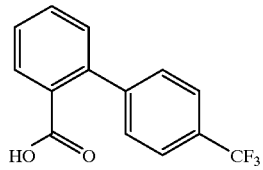

Synthon G is commercially available, for example, from Aldrich Chemical Company, Milwaukee, Wis. 53201 USA.

Example H

Preparation of Synthon H

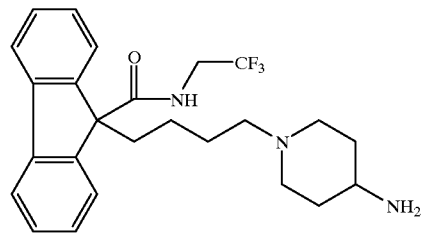

The preparation of Synthon H as the dihydrochloride salt is described as part of Example 11 in U.S. Pat. No. 5,712,279.

Example I

Preparation of Synthon I

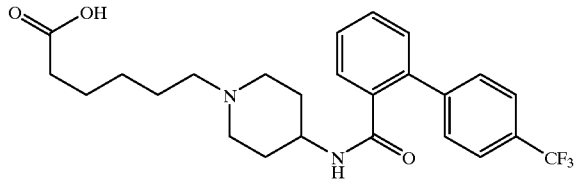

Synthon I is prepared by alkylation of Synthon F with 6-bromohexanoic acid. A solution of Synthon F hydrochloride (18.0 g, 49 mmol) in 100 mL dimethylformamide is stirred under argon at room temperature and treated with potassium carbonate (12.6 g, 49 mmol) followed by 6-bromohexanoic acid (9.6 g, 49 mmol). The reaction is heated to 50° C. for 24 h. After cooling, the reaction is filtered to remove potassium carbonate, and the filter cake is rinsed with ethyl acetate. The solvents are removed in vacuo to afford a solid from which Synthon I can be obtained as an off-white solid after recrystallization from ethyl acetate (18.6 g, 38.7 mmol, 79%).

Example 1

Synthesis of

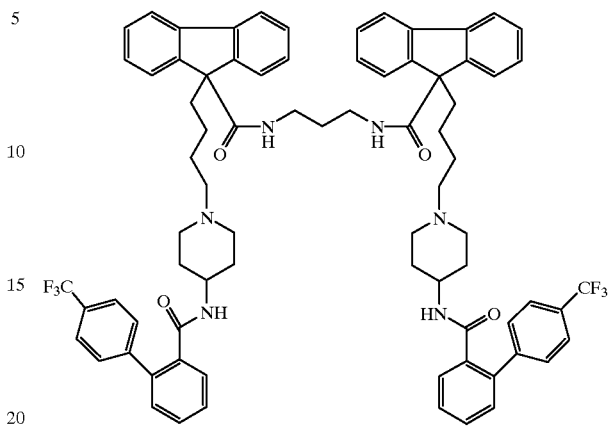

A solution of 100 mmols of Synthon A in 200 mL of THF under $N_2$ is treated at room temperature with 100 mmols of trifluoroacetic anhydride and stirred for 1 hr. To the resultant mixture is added a solution of 50 mmols of 1,3-diaminopropane and 200 mmols of triethylamine in 200 mL of THF. The temperature is raised to 60° C. and the reaction followed by TLC. When the reaction is essentially complete by TLC, the solvent is removed in vacuo and the residue partitioned between ethyl acetate and water. The organic layer is washed with water, dried over sodium sulfate, filtered and the solvent removed. The final product is purified by crystallization or chromatography.

Using this procedure, other compounds of formula I may be prepared by employing alternative diamine linker molecules and analogs of Synthon A.

Example 2

Synthesis of

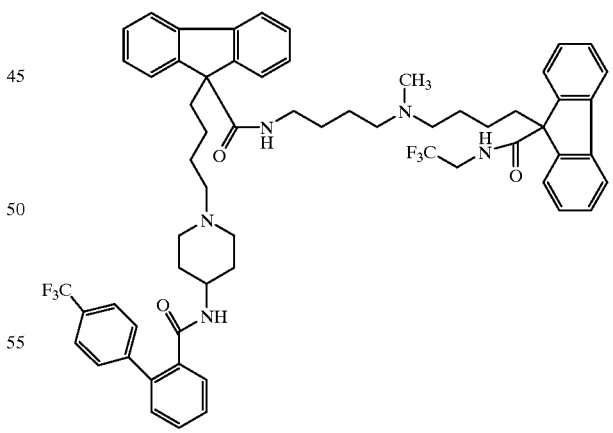

A mixture of 100 mmols of phthalic anhydride and 120 mmols of 1-amino-4-butanol in 200 mL of toluene is refluxed with azeotropic removal of water. The reaction is followed by TLC and when judged complete, is cooled and washed with 1N HCl and water and dried over sodium sulfate. To this solution is added 100 mmols of triethylamine followed by 100 mmols of methanesulfonyl chloride with cooling. After 1 hr., the mixture is washed with water, dried over sodium sulfate and the solvent removed in vacuo. The resulting phthalimide mesylate is dissolved in 100 mL of DMF and 100 mmols of Synthon E, 100 mmols of potassium carbonate and 50 mmols of potassium iodide are added. The mixture is maintained at 60° C. under $N_2$ for 24 hrs. then diluted with water. The product is washed with water and purified if necessary. The phthalimide is removed by refluxing a solution of the above material in 100 mL of ethanol with 120 mnmols of hydrazine hydrate (TLC). When complete, the reaction is filtered and the solvent removed. The residue is purified as required.

A solution of 100 mmols of Synthon A in 100 mL of THF is treated at room temperature with 100 mmols of trifluoroacetic anhydride and after 1 hr the resulting solution is added to a solution of the above amine in 100 mL of THF with 200 mmols of triethylamine. The reaction is followed by TLC and when judged complete, the solvent is removed and the residue partitioned between ethyl acetate and water. The organic phase is repeatedly washed with water, dried over sodium sulfate, filtered and the solvent removed. The final product is purified by crystallization or chromatography.

In a similar manner, other compounds of formula I may be prepared by using alternative amino-alcohol linker molecules and analogs of the Synthons.

Example 3

Synthesis of

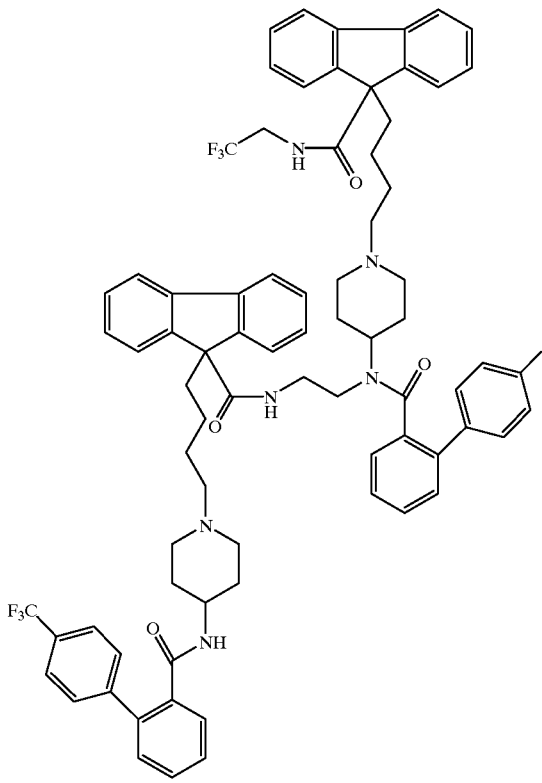

A solution of 100 mmols of Synthon A in 200 mL of THF under $N_2$ is treated at room temperature with 100 mmols of trifluoroacetic anhydride and stirred for 1 hr. To the resultant solution is added a mixture of 100 mmols Synthon C and 200 mmols triethylamine in 100 mL THF. The temperature is raised to 60° C. and the reaction is followed by TLC. When is essentially complete by TLC, the solvent is removed in vacuo and the residue partitioned between ethyl acetate and water. The organic layer is washed with water, dried over sodium sulfate, filtered and the solvent removed. The final product is purified by crystallization or chromatography.

In a similar manner, other compounds of formula I may be prepared by using analogs of Synthon A or C.

Example 4

Synthesis of

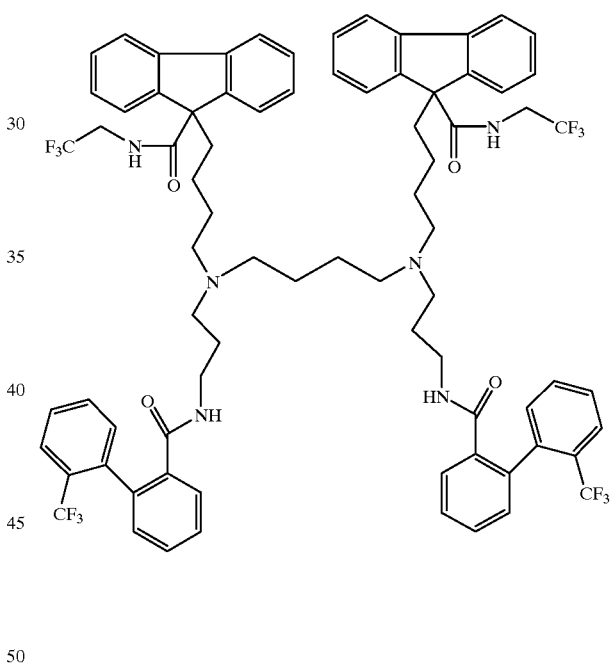

A mixture of 100 mmols of Synthon B in 100 mL of DMF with 50 mmols of 1,4-dibromobutane and 100 mmols of potassium carbonate is stirred under $N_2$ at 60° C. for 24 hr. The reaction is cooled and 500 mL of water added. The resultant final product is isolated, washed with water and purified by crystallization or chromatography.

In a similar manner, other compounds of formula I may be prepared by using alternative dihalo linker molecules and analogs of Synthon B.

Example 5

Synthesis of

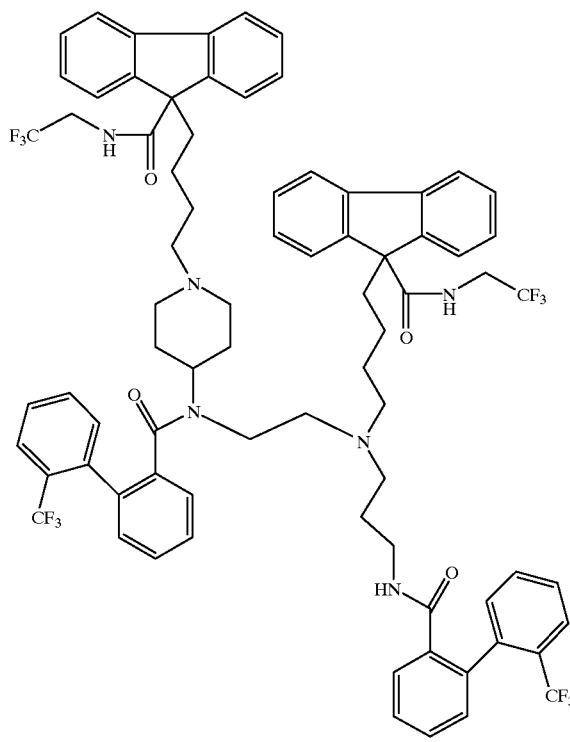

A solution of 100 mmols of Synthon C in 100 mL of THF is treated with 100 mmols of trifluoroacetic anhydride and 100 mmols of triethylamine. After 1 hr., the solvent is removed in vacuo and the residue partitioned between ethyl acetate and water. The organic layer is washed with water, dried over sodium sulfate, filtered and the solvent removed to afford the crude trifluoroacetamide.

A solution of 100 mmols of Synthon G in 200 mL methylene chloride is treated with 150 mmols of oxalyl chloride and a few drops of DMF. After 2 hrs., the solvent is removed and the residue is dissolved in 100 mL of methylene chloride and added to a mixture of 100 mmols of 3-bromopropylamine hydrobromide and 250 mmols of triethylamine in 100 mL of methylene chloride. After 1 hr., the solvent is removed in vacuo and the residue partitioned between ethyl acetate and water. The organic layer is washed with water, dried over sodium sulfate, filtered and the solvent removed to afford the crude bromopropylamide which is purified by chromatography or crystallization as necessary.

A solution of the above crude trifluoroacetamide in 200 mL of THF is cooled under $N_2$ to $-78°$ C. and 100 mL of 1N LDA in THF is added. The temperature is raised to $-20°$ C. and a solution of the above brompropylamide in 100 mL of THF is added. The temperature is slowly raised as required and the reaction followed by TLC. When the reaction is essentially complete by TLC, 150 mL of 1N NaOH solution is added and the temperature is raised to 60° C. until the trifluoraoacteamide is removed (TLC). The solvent is removed in vacao and the residue partitioned between ethyl acetate and water. The organic layer is washed with water, dried over sodium sulfate, filtered and the solvent removed. The product is purified by crystallization or chromatography to afford Intermediate A.

A solution of 50 rnmols of Intermediate A in 50 mL of DMF with 50 mmols of Synthon J and 50 mmols of potassium carbonate is maintained at 60° C. for 24 hrs. The reaction is cooled and 500 mL of water added. The resultant final product is isolated, washed with water and purified by crystallization or chromatography.

In a similar manner, other compounds of formula I may be prepared by using other halo-amine linkers and analogs of the Synthons.

Example 6

Synthesis of

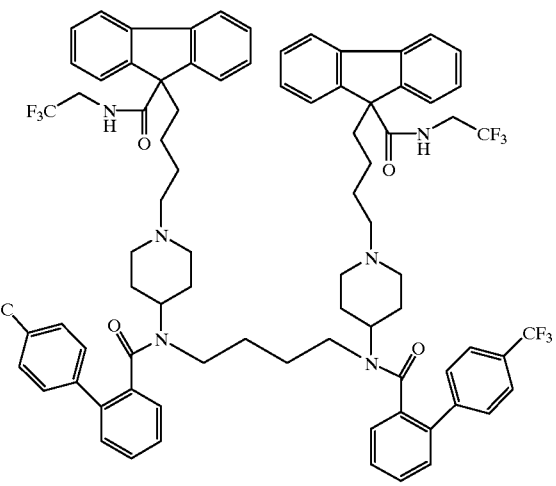

A solution of 100 mmols of Synthon H in 100 mL of ethyl acetate is treated with 100 mmols of trifluoroacetic anhydride. After 1 hr., the reaction is made basic with $NaHCO_3$ and washed with water, dried over sodium sulfate, filtered and the solvent removed to afford crude trifluoroacetamide. This material is dissolved in 100 mL of THF and the solution cooled to $-78°$ C. Following addition of 100 mL of 1N LDA in THF the temperature is raised to $-20°$ C. and 50 mmols of 1,4-dibromobutane is added. The temperature is slowly raised as required and the reaction followed by TLC. When the reaction is essentially complete by TLC, 150 mL of 1N NaOH solution is added and the temperature is raised to 60° C. until the trifluoraoacteamide is removed (TLC). The solvent is removed in vacuo and the residue partitioned between ethyl acetate and water. The organic layer is washed with water, dried over sodium sulfate, filtered and the solvent removed. The product is purified by crystallization or chromatography to afford Intermediate B.

A solution of 100 mmols of Synthon G in 200 mL of methylene chloride is treated with 150 mmols of oxalyl chloride and a few drops of DMF. After 2 hrs., the solvent is removed and the residue is dissolved in 200 mL of methylene chloride and added to a solution of intermediate 2 in 100 mL of methylene chloride with 150 mmols of triethylamine. After 1 hr., the solvent is removed in vacuo and the residue partitioned between ethyl acetate and water. The organic layer is washed with water, dried over sodium sulfate, filtered and the solvent removed to afford the final product which may be purified by crystallization or chromatography.

In a similar manner, other compounds of formula I may be prepared by using alternative dihalo linker molecules and analogs of the Synthons.

Example 7

Synthesis of

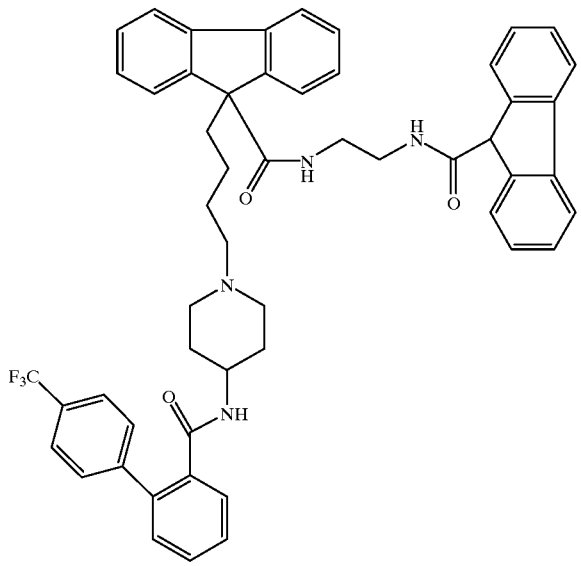

A solution of 100 mmols of Synthon D in methylene chloride is treated with 150 mmols of oxalyl chloride and a few drops of DMF. After 2 hrs. the solvent is removed and the residue dissolved in 200 mL methylene chloride and added slowly to an excess of neat 1,3-diaminopropane and 100 mmols of triethylamine in 200 mL of methylene chloride. After 1 hr. the solvent is removed and the residue stirred with water which is discarded. The remaining material is partitioned between ethyl acetate and 1N HCl. The aqueous phase is thoroughly extracted with ethyl acetate to remove any bis-amide and then made basic. This aqueous mixture is extracted with ethyl acetate which is dried over sodium sulfate, filtered and the solvent removed. The crude amino amide is purified by crystallization or chromatography.

A solution of 100 mmols of Synthon A in 100 mL of THF is treated with 100 mmols of trifluoroacetic anhydride. After 1 hr. this solution is added to a solution of the above amide and 200 mmols of triethylamine in 200 mL of THF. After 1 hr., the solvent is removed in vacuo and the residue partitioned between ethyl acetate and water. The organic layer is washed with water, dried over sodium sulfate, filtered and the solvent removed to afford the final product which may be purified by crystallization or chromatography.

In a similar manner, other compounds of formula I may be prepared by using alternative diamino linker molecules and analogs of the Synthons.

Example 8

Synthesis of

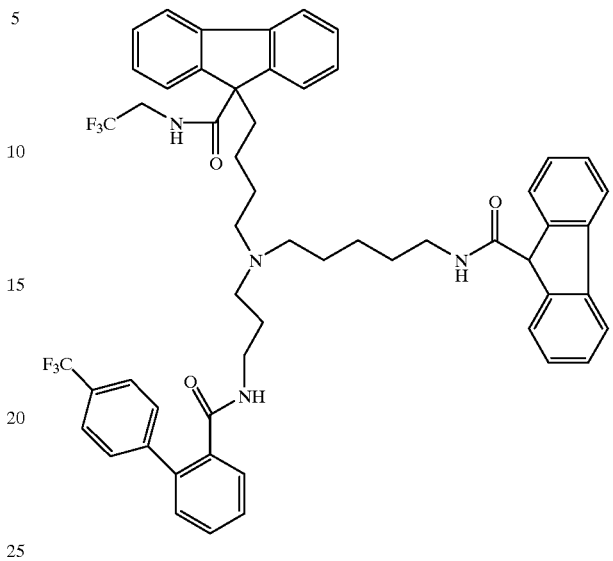

A solution of 100 mmols of Synthon D in 200 mL methylene chloride is treated with 150 mmols of oxalyl chloride and a few drops of DMF. After 2 hrs., the solvent is removed and the residue is dissolved in 200 mL of methylene chloride and added to 100 mmols of 5-aminopentanol and 120 mmols of triethylamine. After 1 hr., the solvent is removed in vacuo and the residue partitioned between ethyl acetate and water. The organic layer is washed with 1N HCl followed by water, dried over sodium sulfate, filtered and the solvent removed to afford crude hydroxyamide. This material is dissolved in 100 mL of THF with 100 mmols of triethylamine, and 100 mmols of methanesulfonyl chloride added. After 1 hr., the solvent is removed in vacuo and the residue partitioned between ethyl acetate and water. The organic layer is washed with water, dried over sodium sulfate, filtered and the solvent removed to afford Intermediate C.

A solution of 100 mmols of Intermediate C, 100 mmols of Synthon B, 100 mmols of potassium carbonate and 50 mmols of potassium iodide in 100 mL of DMF is kept at 60° C. under $N_2$ for 24 hrs. The mixture is cooled and 500 mL of water is added and the product is isolated and washed with water. The final product is purified by crystallization or chromatography.

In a similar manner, other compounds of formula I may be prepared by using alternative amino alcohol linker molecules and analogs of the Synthons.

Example 9

Synthesis of

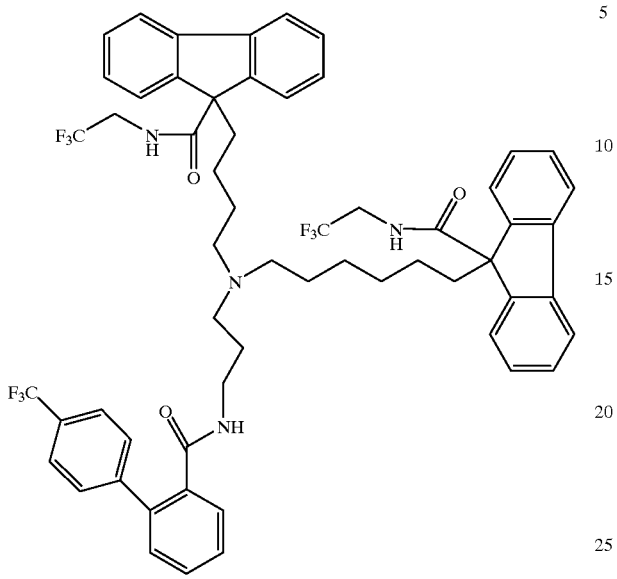

A solution of 100 mmols of 6-bromo-1-hexanol and 120 mL of freshly distilled dihydropyran in 150 mL of anhyd. ether is treated with 1 drop of $POCl_3$. After 1 hr. the mixture is washed with sat. $NaHCO_3$, dried over sodium sulfate, filtered and the solvent removed. The residue is dissolved in 100 mL of DMF and 100 mmol of Synthon E and 100 mmols of potassium carbonate is added. The mixture is kept a 60° C. under $N_2$ for 24 hrs. then cooled and partitioned between ethyl acetate and water. The organic phase is repeatedly washed with water and 50 mL of trifluoroacetic acid added. When TLC indicates that THP removal is complete, the solution is washed with water then sat. $NaHCO_3$ until basic, dried over sodium sulfate and filtered. To this solution is added 100 mmols of methanesulfonyl chloride in 200 mL of ethyl acetate. After 1 hr. the reaction mixture is made basic with sat. $NaHCO_3$ and the organic phase washed with water, dried over sodium sulfate, filtered and the solvent removed to afford the mesylate Intermediate D.

A mixture of 100 mmols of Intermediate D, 100 mmols of Synthon B, 100 mmols of potassium carbonate and 50 mmols of sodium iodide in 100 mL of DMF is kept at 60° C. under $N_2$ for 24 hrs. The mixture is cooled and 500 mL of water is added. The material is isolated and washed with water. The final product is purified by crystallization or chromatography.

In a similar manner, other compounds of formula I may be prepared by using alternative halo alcohol linker molecules and analogs of the Synthons.

Example 10

Synthesis of

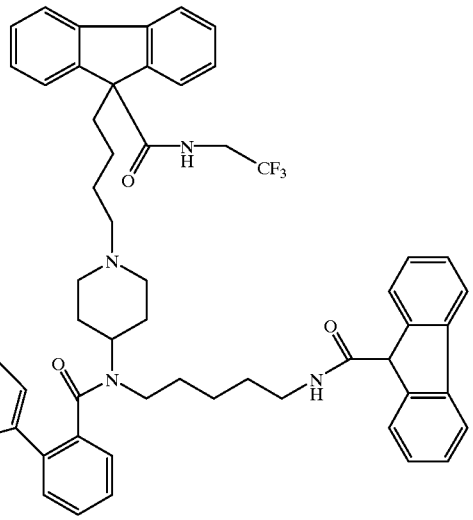

A solution of 100 nimols of Synthon H in 100 mL of ethyl acetate is treated with 100 mmols of trifluoroacetic anhydride. After 1 hr., the reaction is made basic with $NaHCO_3$ and washed with water, dried over sodium sulfate, filtered and the solvent removed. The residue is dissolved in 100 mL of THF and cooled under $N_2$ to −78° C. After addition of 100 mL of a 1N LDA/THF solution, the temperature is raised to −20° C. and 100 mmols of Intermediate C added. The temperature is raised as required and the reaction followed by TLC. When judged complete, 100 mL of 1N NaOH solution is added and the reaction warmed to remove the trifluoroacetamide. After removal of the solvent, extractive workup with ethyl acetate/water affords Intermediate E.

A solution of 100 mmols of Synthon G in 100 mL of THF is treated with 100 mL of trifluoroacetic anhydride. After 1 hr., the resultant solution is added to a solution of 100 mmols of Intermediate E and 200 mmols of triethylamine in 100 mL of THF. The temperature is warmed as required and when TLC indicates that the coupling is complete the solvent is removed and the residue is partitioned between water and ethyl acetate. The organic phase is washed with water, dried over sodium sulfate, filtered and the solvent removed. The final product is purified by crystallization or chromatography.

In a similar manner, other compounds of formula I may be prepared by using alternative amino alcohol linker molecules and analogs of the Synthons.

Example 11

Synthesis of

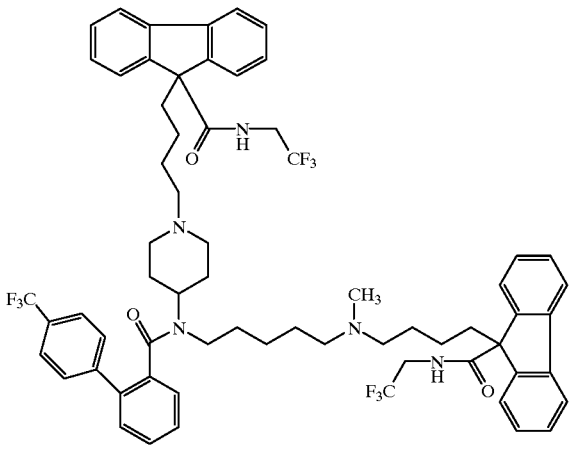

A solution of 100 mmols of Synthon H in 100 mL of ethyl acetate is treated with 100 mmols of trifluoroacetic anhydride. After 1 hr., the reaction is made basic with NaHCO$_3$ and washed with water, dried over sodium sulfate, filtered and the solvent removed. The residue is dissolved in 100 mL of THF and cooled under N$_2$ to −78° C. After addition of 100 mL of a 1N LDA/THF solution, the temperature is raised to −20° C. and 100 mmols of Intermediate D added. The temperature is raised as required and the reaction followed by TLC. When judged complete, 100 mL of 1N NaOH solution is added and the reaction warmed to remove the trifluoroacetamide. After removal of the solvent, extractive workup with ethyl acetate/water afforded Intermediate F.

A solution of 100 mmols of Synthon G in 100 mL of THF is treated with 100 mL of trifluoroacetic anhydride. After 1 hr., the resultant solution is added to a solution of 100 mmols of Intermediate F and 200 mmols of triethylamine in 100 mL of THF. The temperature is warmed as required and when TLC indicates that the coupling is complete the solvent is removed and the residue is partitioned between water and ethyl acetate. The organic phase washed with water, dried over sodium sulfate, filtered and the solvent moved. The final product is purified by crystallization or chromatography.

In a similar manner, other compounds of formula I may be prepared by sing alternative bromo alcohol linker molecules and analogs of the Synthons.

Example 12

Synthesis of

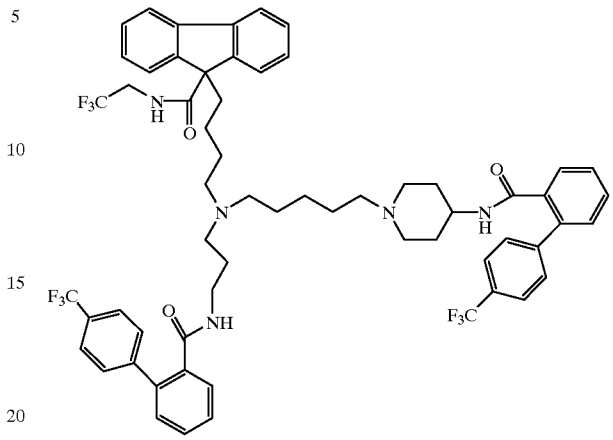

A solution of 100 mmols of 6-bromo-1-hexanol and 120 mL of freshly distilled dihydropyran in 150 mL of anhyd. ether is treated with 1 drop of POCl$_3$. After 1 hr., the mixture is washed with sat. NaHCO$_3$, dried over sodium sulfate, filtered and the solvent removed. The residue is dissolved in 100 mL of DMF and 100 mmol of Synthon F and 100 mmols of potassium carbonate added The mixture is kept a 60° C. under N$_2$ for 24 hrs. then cooled and partitioned between ethyl acetate and water. The organic phase is repeatedly washed with water and 50 mL of trifluoroacetic acid added. When TLC indicates that THP removal is complete, the solution is washed with water then sat. NaHCO$_3$ until basic, dried over sodium sulfate and filtered. To this solution is added 100 mmols of methanesulfonyl chloride in 200 mL of ethyl acetate. After 1 hr., the reaction mixture is made basic with sat. NaHCO$_3$ and the organic phase washed with water, dried over sodium sulfate, filtered and the solvent removed to afford the mesylate Intermediate G.

A mixture of 100 mmols of Intermediate G, 100 mmols of Synthon B, 100mmols of potassium carbonate and 50 mmols of sodium iodide in 100 mL of DMF is kept at 60° C. under N$_2$ for 24 hrs. The mixture is cooled and 500 mL of water added. The material is isolated and washed with water. The final product is purified by crystallization or chromatography.

In a similar manner, other compounds of formula I may be prepared by using alternative bromo alcohol linker molecules and analogs of the Synthons.

Example 13

Synthesis of

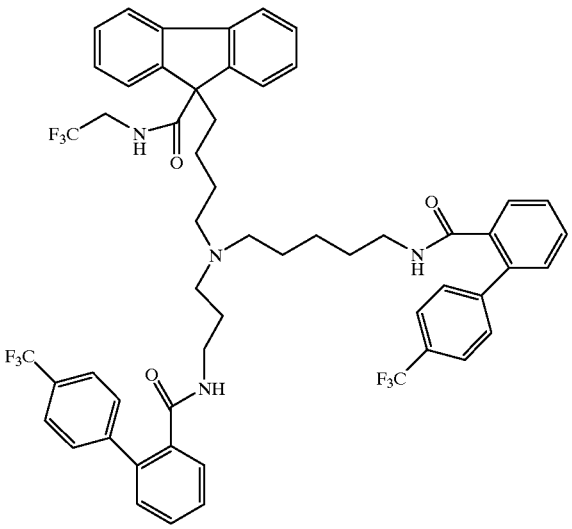

A solution of 100 mmols of Synthon G in 200 mL methylene chloride is treated with 150 mmols of oxalyl chloride and a few drops of DMF. After 2 hrs., the solvent is removed and the residue is dissolved in 200 mL of methylene chloride and added to 100 mmols of 5-aminopentanol and 120 mmols of triethylamine. After 1 hr., the solvent is removed in vacuo and the residue partitioned between ethyl acetate and water. The organic layer is washed with 1N HCl followed by water, dried over sodium sulfate, filtered and the solvent removed to afford crude hydroxyamide. This material is dissolved in 100 mL of THF with 100 mmols of triethylamine, and 100 mmols of methanesulfonyl chloride added. After 1 hr., the solvent is removed in vacuo and the residue partitioned between ethyl acetate and water. The organic layer is washed with water, dried over sodium sulfate, filtered and the solvent removed to afford Intermediate H.

A solution of 100 mmols of Intermediate H, 100 mmols of Synthon B, 100 mmols of potassium carbonate and 50 mmols of potassium iodide in 100 mL of DMF is kept at 60° C. under $N_2$ for 24 hrs. The mixture is cooled and 500 mL of water is added and the product is isolated and washed with water. The final product is purified by crystallization or chromatography.

In a similar manner, other compounds of formula I may be prepared by using alternative amino alcohol linker molecules and analogs of the Synthons.

Example 14

Synthesis of

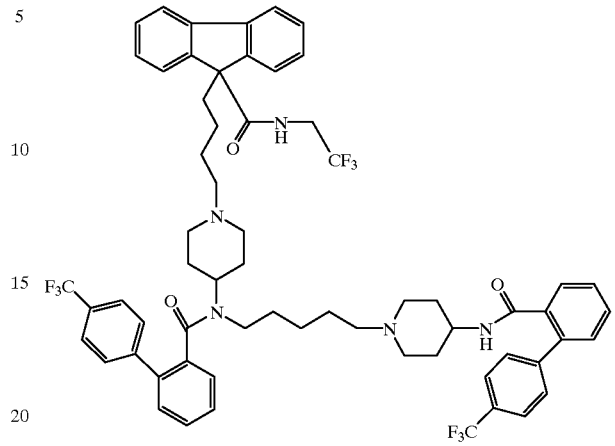

A solution of 100 mmols of Synthon H in 100 mL of ethyl acetate is treated with 100 mmols of trifluoroacetic anhydride. After 1 hr., the reaction is made basic with $NaHCO_3$ and washed with water, dried over sodium sulfate, filtered and the solvent removed. The residue is dissolved in 100 mL of THF and cooled under $N_2$ to −78° C. After addition of 100 mL of a 1N LDA/THF solution, the temperature is raised to −20° C. and 100 mmols of Intermediate G added. The temperature is raised as required and the reaction followed by TLC. When judged complete, 100 mL of 1N NaOH solution is added and the reaction warmed to remove the trifluoroacetamide. After removal of the solvent, extractive workup with ethyl acetate/water afforded Intermediate I.

A solution of 100 mmols of Synthon G in 100 mL of THF is treated with 100 mL of trifluoroacetic anhydride. After 1 hr., the resultant solution is added to a solution of 100 mmols of Intermediate I and 200 mmols of triethylamine in 100 mL of THF. The temperature is warmed as required and when TLC indicates that the coupling is complete the solvent is removed and the residue is partitioned between water and ethyl acetate. The organic phase is washed with water, dried over sodium sulfate, filtered and the solvent removed. The final product is purified by crystallization or chromatography.

In a similar manner, other compounds of formula I may be prepared by using alternative bromo alcohol linker molecules and analogs of the Synthons.

Example 15

Synthesis of

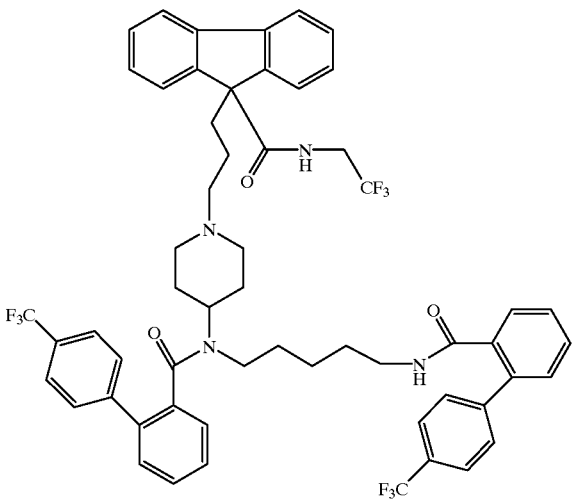

A solution of 100 mmols of Synthon H in 100 mL of ethyl acetate is treated with 100 mmols of trifluoroacetic anhydride. After 1 hr., the reaction is made basic with NaHCO$_3$ and washed with water, dried over sodium sulfate, filtered and the solvent removed. The residue is dissolved in 100 mL of THF and cooled under N$_2$ to −78° C. After addition of 100 mL of a 1N LDA/THF solution, the temperature is raised to −20° C. and 100 mmols of Intermediate H added. The temperature is raised as required and the reaction followed by TLC. When judged complete, 100 mL of 1N NaOH solution is added and the reaction warmed to remove the trifluoroacetamide. After removal of the solvent, extractive workup with ethyl acetate/water afforded Intermediate J.

A solution of 100 mmols of Synthon G in 100 mL of THF is treated with 100 mL of trifluoroacetic anhydride. After 1 hr., the resultant solution is added to a solution of 100 mmols of Intermediate E and 200 mmols of triethylamine in 100 mL of THF. The temperature is warmed as required and when TLC indicates that the coupling is complete the solvent is removed and the residue is partitioned between water and ethyl acetate. The organic phase is washed with water, dried over sodium sulfate, filtered and the solvent removed. The final product is purified by crystallization or chromatography.

In a similar manner, other compounds of formula I may be prepared by using alternative amino alcohol linker molecules and analogs of the Synthons.

Example 16

Synthesis of

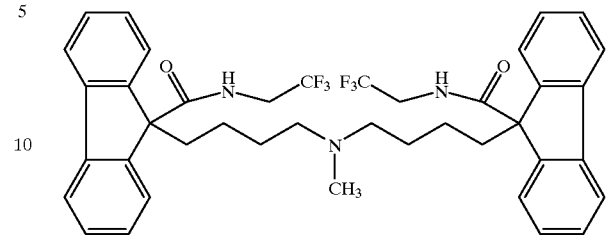

A mixture of 100 mmols of Synthon E and 100 mmols of Synthon J in 100 mL of DMF with 100 mmols of potassium carbonate is kept at 60° C. under N$_2$ for 24 hrs. The reaction is cooled and 500 mL of water added. The final product is isolated, washed with water and purified by crystallization or chromatography.

Example 17

Synthesis of

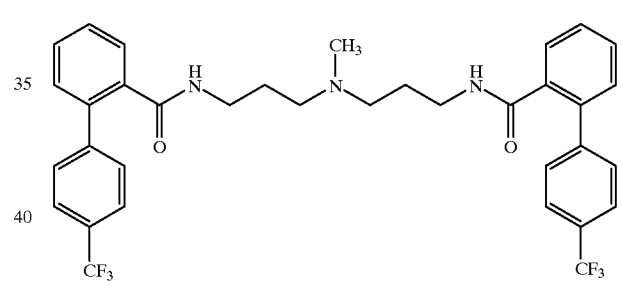

A solution of 100 mmols of Synthon G in 100 mL of THF is treated with 100 mmols of trifluoroacetic anhydride at room temperature. After 1 hr., this solution is added to a solution of 50 mmols of 3,3'-diamino-N-methyldipropylamine and 200 mmols of triethylamine in 100 mnL of THF. The temperature is raised as necessary and the reaction followed by TLC. When the reaction is judged to be complete by TLC, the solvent is removed and the residue partitioned between ethyl acetate and water. The organic layer is washed repeatedly with water, dried over sodium sulfate, filtered and the solvent removed. The final product is purified by crystallization or chromatography.

In a similar manner, other compounds of formula I may be prepared by using alternative diamino linker molecules and analogs of the Synthons.

Example 18

Synthesis of

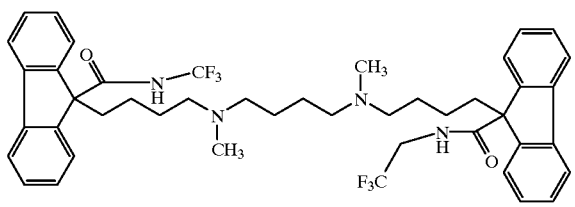

A mixture of 100 mmols of Synthon E and 50 mmols of 1,4-dibromobutane in 100 mL of DMF with 100 mmols of potassium carbonate is kept at 60° C. under $N_2$ for 24 hrs. The reaction is cooled and 500 mL of water added. The final product is isolated, washed with water and purified by crystallization or chromatography.

In a similar manner, other compounds of formula I may be prepared by using alternative dihalo linker molecules and analogs of the Synthons.

Example 19

Synthesis of

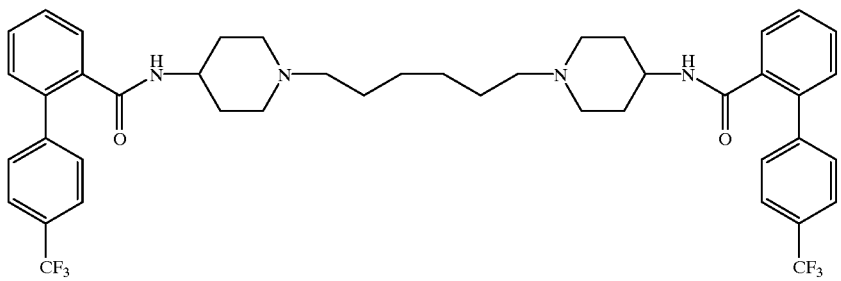

A mixture of 100 mmols of Synthon F and 50 mmols of 1,6-dibromohexane in 100 mL of DMF with 100 mmols of potassium carbonate is kept at 60° C. under $N_2$ for 24 hrs. The reaction is cooled and 500 mL of water added. The final product is isolated, washed with water and purified by crystallization or chromatography.

In a similar manner, other compounds of formula I may be prepared by using alternative dihalo linker molecules and analogs of the Synthons.

Example 20

Synthesis of

A solution of 50 mmols of glutaryl dichloride in 100 mL of ethyl acetate is added to a solution of 100 mmols of Synthon H and 100 mmols of triethylamine in 100 mL of ethyl acetate. After 1 hr., the solution is thoroughly washed with water, dried over sodium sulfate, filtered and the solvent removed. The resulting final product is purified by chromatography or crystallization.

In a similar manner, other compounds of formula I may be prepared by using alternative diacid chloride linker molecules and analogs of the Synthons.

Example 21

Synthesis of

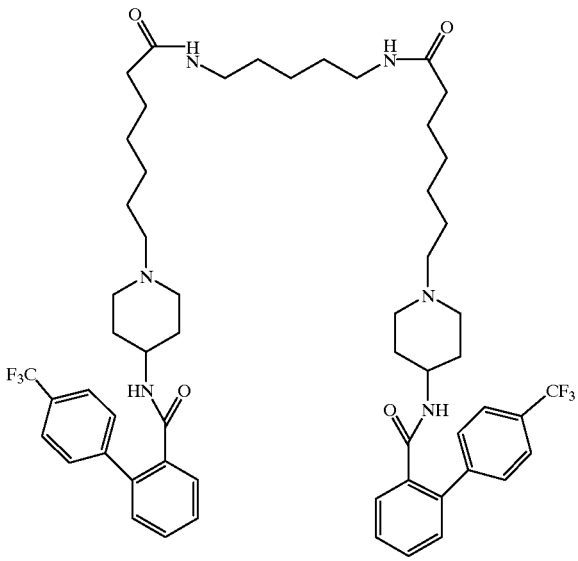

A solution of 100 mmols of Synthon I in 100 mL of THF is treated with 100 mmols of trifluoroacetic anhydride at room temperature. After 1 hr., the reaction mixture is added to a solution of 50 mmols of 1,5-diaminopentane in 100 mL of THF with 200 mmols of triethylamine. The reaction is followed by TLC and when judged to be complete, the solvent is removed and the residue partitioned between water and ethyl acetate. The organic phase is washed with water, dried over sodium sulfate, filtered and the solvent removed. The final product is purified by crystallization or chromatography.

In a similar manner, other compounds of formula I may be prepared by using alternative diamino linker molecules and analogs of the Synthons.

Bioassay Example 1

Inhibition of Triglyceride Transfer

MTP activity is routinely determined by measuring the rate of transfer of radiolabeled triglyceride from donor small unilamellar vesicles (SUV) to acceptor SUV. In this bioassay, the inhibition of radiolabled triglyceride transfer between donor and acceptor vesicles is determined using the procedure described in J. R. Wetterau et al., *Biochim. Biophys. Acta* 1997, 1345, 136–150.

A typical transfer reaction mixture contains donor vesicles (40 mmol egg phosphatidyl choline, 0.25 mol % radiolabeled triglyceride ($[^{14}C]$triolein), and 7.5 mol % cardiolipin), acceptor vesicles (240 mmol egg phosphatidyl choline and 0.25% unlabeled triglyceride) and 5 mg bovine serum albumin in a total of 0.9 mL buffer. The negative charge in the donor vesicles due to the presence of cardiolipin facilitates the separation of donor and acceptor membranes. Following a transfer reaction, a DEAE-cellulose suspension is added to selectively bind the negatively charged donor vesicles. The DEAE-cellulose and bound donor membranes are then pelleted by low speed centrifugation. The acceptor SUV concentration in the assay mixture is kept in excess over that of the donor SUV to minimize back transfer from acceptor to donor vesicles. First-order kinetics are used to quantify total lipid transfer. This corrects for the dilution of labeled lipid in the donor vesicles as the transfer reaction proceeds. The transfer activity is generally expressed as a percent of the donor lipid transferred per unit of time.

Bioassay Example 2

Inhibition of Lipoprotein Secretion by HepG2 Cells

In this bioassy, the inhibition of lipoprotein secretion by cultured human hepatoma cells (HepG2) is determined using the procedure described in H. Jamil et al., *Proc. Natl. Acad. Sci. U.S.A.* 1996, 93, 11991–11995.

HepG2 cells are seeded at a density of approximately 50% confluency in 48-well plates and allowed to grow for 48 h before treatment. At this time, the medium is replaced with fresh medium containing 0.5% DMSO and a range of concentrations of the inhibitor. After a 16 h incubation under standard cell culture conditions, the medium is diluted with fresh tissue culture medium 30-fold for an apoB ELISA, and 60-fold for an apoAI ELISA. A sandwich ELISA is used to measure apoB in the media. A similar assay is used to quantitate apoAI. For the apoAI assay, the primary and secondary antibodies are a monoclonal anti-human apoAI (1:500 dilution) and a goat anti-human apoAI polyclonal antibody (1:500). The concentration of the respective proteins is measured against a 2-fold dilution standard curve from 1.25–40 ng/mL of the purified proteins. In this range of concentrations, both assays show a linear response. Each inhibitor concentration is tested in duplicate cultures, and apoB and apoAI are measured by ELISA in each culture in triplicate.

Bioassay Example 3

Inhibition of Triglyceride Secretion in Rats

In this bioassay, the inhibition of triglyceride secretion in fasted and fed rats is determined using the procedure described in J. R. Wetterau et al., *Nature* 1998, 282, 751–754.

Sprague-Dawley rats (~200 g each, four per treatment group) are adapted to a reversed diurnal light cycle for two weeks. Before the experiment, the rats either are fasted or have free access to food for 18 hours. The animals are dosed with a test compound one hour before receiving an intravenous injection of Triton WR1339 (250 mg/kg), which prevents the catabolism of triglyceride-rich lipoproteins produced during the course of the experiment. The triglyceride secretion rate is determined by calculating the amount of triglyceride that is accumulated in plasma during the 2.5 hours after the Triton injection. The standard assay is linear for at least 5 hours after the Triton injection. Plasma triglyceride levels are determined with a Roche Cobas blood chemistry autoanalyzer.

Bioassay Example 4

Diminution of Serum Cholesterol Levels in Hamsters

In this bioassay, the diminution of serum cholesterol levels in hamsters is determined using the procedure described in J. R. Wetterau et al., *Nature* 1998, 282, 751–754.

Male Golden Syrian hamsters (~140 g each, four per treatment group) are adapted to and maintained on a reverse diurnal light cycle. They are dosed once a day with a test compound and are allowed free access to a standard hamster diet. After seven days of treatment, hamsters are fasted for 18 hours, after which plasma lipid levels (triglycerides and cholesterol) and chemistries are determined with a Roche Cobas blood chemistry autoanalyzer. Hamster lipoprotein fractions (VLDL, LDL, HDL) are quantitated after the precipitation of apoB-containing lipoproteins with phosphotungstate and magnesium chloride.

Bioassay Example 5

Amelioration of Hyperlipidemia in WHHL Rabbits

In this bioassay, the amelioration of hyperlipidemia in Watanabe-heritable hyperlipidemic (WHHL) rabbits is determined using the procedure described in J. R. Wetterau et al., Nature 1998, 282, 751–754.

Five WHHL rabbits are treated with a test compound for 14 days. Plasma lipid levels (triglycerides and cholesterol) and chemistries are determined with a Roche Cobas blood chemistry autoanalyzer 18 hours after the last dose.

What is claimed is:

1. A compound of formula II:

II wherein each L' is a ligand independently selected from the group consisting of:

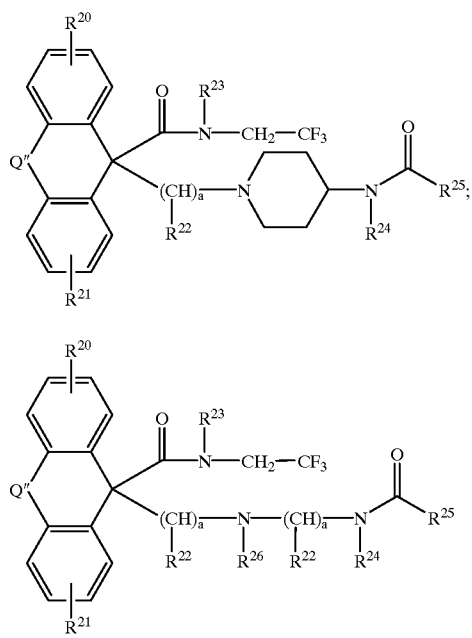

wherein
each $R^{20}$ and $R^{21}$ is independently selected from the group consisting of hydrogen and halo;
each $R^{22}$ is independently selected from the group consisting of hydrogen, alkyl and halo;
each $R^{23}$ is independently selected from the group consisting of hydrogen and a covalent bond linking the ligand to the linker;
each $R^{24}$ is independently selected from the group consisting of hydrogen and a covalent bond linking the ligand to the linker;
each $R^{25}$ is independently selected from the group consisting of aryl, heteroaryl, heterocyclic, cycloalkyl, substituted cycloalkyl and a covalent bond linking the ligand to the linker;
each $R^{26}$ is independently selected from the group consisting of hydrogen, alkyl and a covalent bond linking the ligand to the linker;
each Q" is independently selected from the group consisting of a covalent bond, —O— and —S—;
each a is independently an integer of from 2 to 6;
X' is a linker represented by the formula:

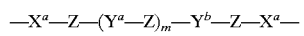

wherein
m is an integer of from 0 to 20;
$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;
$Y^a$ and $Y^b$ at each separate occurrence are selected from the group consisting of —C(O)NR'—, —NR'C(O)—, —NR'C(O)NR', —C(=NR')—NR', —NR'—C(=NR')—, —NR'—C(O)—O—, —N=C($X^a$)—NR'—, —P(O)(OR')—O—, —S(O)$_n$CR'R"—, —S(O)$_n$—NR'—, —S—S— and a covalent bond; where n is 0, 1 or 2; and
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
and pharmaceutically-acceptable salts or pro-drugs thereof;
provided that in each ligand only one of $R^{23}$, $R^{24}$, $R^{25}$ and $R^{26}$ is a covalent bond linking the ligand to the linker.

2. The compound of claim 1, wherein each $R^{25}$ group is independently selected from the group consisting of aryl, heteroaryl, heterocyclic, cycloalkyl and substituted cycloalkyl.

3. The compound of claim 2, wherein $R^{25}$ is an aryl group.

4. The compound of claim 3, wherein the aryl group is substituted with from 1 to 4 substituents and one of the substituents is attached in the ortho position to the —C(O)— group.

5. The compound of claim 4, wherein each $R^{25}$ is a 2-(4'-trifluoromethylphenyl)phenyl group.

6. A pharmaceutical composition comprising a pharmaceutically acceptable carrier and an effective amount of a multibinding compound of formula II:

II wherein each L' is a ligand independently selected from the group consisting of:

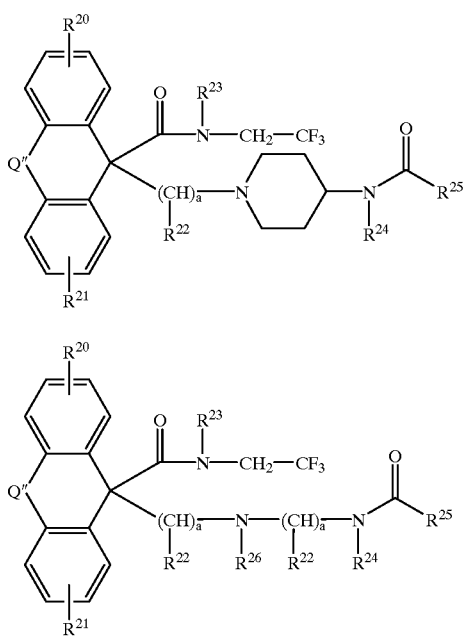

wherein each $R^{20}$ and $R^{21}$ is independently selected from the group consisting of hydrogen and halo;

each $R^{22}$ is independently selected from the group consisting of hydrogen, alkyl and halo;

each $R^{23}$ is independently selected from the group consisting of hydrogen and a covalent bond linking the ligand to the linker;

each $R^{24}$ is independently selected from the group consisting of hydrogen and a covalent bond linking the ligand to the linker;

each $R^{25}$ is independently selected from the group consisting of aryl, heteroaryl, heterocyclic, cycloalkyl, substituted cycloalkyl and a covalent bond linking the ligand to the linker;

each $R^{26}$ is independently selected from the group consisting of hydrogen, alkyl and a covalent bond linking the ligand to the linker;

each Q" is independently selected from the group consisting of a covalent bond, —O— and —S—;

each a is independently an integer of from 2 to 6;

X' is a linker represented by the formula:

$$—X^a—Z—(Y^a—Z)_m—Y^b—Z—X^a—$$

wherein m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of —C(O)NR'—, —NR'C(O)—, —NR'C(O)NR', —C(=NR')—NR', —NR'—C(=NR')—, —NR'—C(O)—O—, —N=C($X^a$)—NR'—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts or pro-drugs thereof;

provided that in each ligand only one of $R^{23}$, $R^{24}$, $R^{25}$, and $R^{26}$ is a covalent bond linking the ligand to the linker.

7. The pharmaceutical composition of claim 6, wherein each $R^{25}$ group is independently selected from the group consisting of aryl, heteroaryl, heterocyclic, cycloalkyl and substituted cycloalkyl.

8. The pharmaceutical composition of claim 7, wherein $R^{25}$ is aryl.

9. The pharmaceutical composition of claim 8, wherein the aryl group is substituted with from 1 to 4 substituents and one of the substituents is attached in the ortho position to the —C(O)— group.

10. The pharmaceutical composition of claim 9, wherein each $R^{25}$ is a 2-(4'-trifluoromethylphenyl)phenyl group.

* * * * *